US008969295B2

(12) United States Patent
Sur et al.

(10) Patent No.: US 8,969,295 B2
(45) Date of Patent: Mar. 3, 2015

(54) IDENTIFYING AND MODULATING MOLECULAR PATHWAYS THAT MEDIATE NERVOUS SYSTEM PLASTICITY

(75) Inventors: Mriganka Sur, Cambridge, MA (US); Daniela Tropea, Cambridge, MA (US); Gabriel Kreiman, West Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1069 days.

(21) Appl. No.: 12/297,189

(22) PCT Filed: Apr. 12, 2007

(86) PCT No.: PCT/US2007/009172
§ 371 (c)(1),
(2), (4) Date: Aug. 11, 2009

(87) PCT Pub. No.: WO2007/120847
PCT Pub. Date: Oct. 25, 2007

(65) Prior Publication Data
US 2009/0297573 A1 Dec. 3, 2009

Related U.S. Application Data

(60) Provisional application No. 60/792,275, filed on Apr. 14, 2006.

(51) Int. Cl.
*A61K 38/30* (2006.01)
*A61K 38/49* (2006.01)
*A61K 38/21* (2006.01)

(52) U.S. Cl.
CPC ............... *A61K 38/30* (2013.01); *A61K 38/217* (2013.01); *A61K 38/49* (2013.01)
USPC ........................... 514/8.6; 514/14.2; 514/17.5

(58) Field of Classification Search
None
See application file for complete search history.

(56) References Cited

U.S. PATENT DOCUMENTS

| 4,272,398 A | 6/1981 | Jaffe et al. |
| 4,346,709 A | 8/1982 | Schmitt et al. |
| 4,692,147 A | 9/1987 | Duggan |
| 4,766,075 A | 8/1988 | Goeddel et al. |
| 4,853,330 A | 8/1989 | Goeddel et al. |
| 5,108,901 A | 4/1992 | Anderson et al. |
| 5,185,259 A | 2/1993 | Goeddel et al. |
| 5,262,170 A | 11/1993 | Anderson et al. |
| 5,330,768 A | 7/1994 | Park et al. |
| 5,385,732 A | 1/1995 | Anderson et al. |
| 5,411,871 A | 5/1995 | Anderson et al. |
| 5,520,911 A | 5/1996 | Anderson et al. |
| 5,520,913 A | 5/1996 | Anderson et al. |
| 5,587,159 A | 12/1996 | Goeddel et al. |
| 5,612,029 A | 3/1997 | Bennett et al. |
| 5,616,486 A | 4/1997 | Anderson et al. |
| 5,626,862 A | 5/1997 | Brem et al. |
| 5,651,986 A | 7/1997 | Brem et al. |
| 5,714,372 A | 2/1998 | Vehar et al. |
| 5,728,565 A | 3/1998 | Goeddel et al. |
| 5,728,566 A | 3/1998 | Goeddel et al. |
| 5,753,486 A | 5/1998 | Goeddel et al. |
| 5,770,426 A | 6/1998 | Anderson et al. |
| 5,797,898 A | 8/1998 | Santini et al. |
| 5,846,565 A | 12/1998 | Brem et al. |
| 5,861,373 A * | 1/1999 | Gluckman et al. ............. 514/8.6 |
| 5,869,314 A | 2/1999 | Goeddel et al. |
| 6,129,761 A | 10/2000 | Hubbell |

(Continued)

FOREIGN PATENT DOCUMENTS

| WO | WO 97/39028 | 10/1997 |
| WO | WO 00/47130 | 8/2000 |

(Continued)

OTHER PUBLICATIONS

Chen J et al. Statins induce angiogenesis, neurogenesis, and synaptogenesis after stroke. Ann Neurol. 2003; 53:743-751.*
Paukku K & Silvennoinen O. STATs as critical mediators of signal transduction and transcription: lessons learned from STAT5. Cytokine Growth Fact Rev. 2004; 435-455.*
Yadav A et a. JAK/STAT3 pathway is involved in survival of neurons in response to insulin-like growth factor and negatively regulated by suppressor of cytokine signaling-3. J Biol Chem, 2005; 280(36):31830-31840.*
Bunn RC et al. Early developmental changes in IGF-I, IGF-II, IGF binding protein-1, and IGF binding protein-3 concentration in the cerebrospinal fluid of children. Pediatric Res. 2005; 58(1):89-93.*
Riikonen R et al. Cerebrospinal fluid insulin-like growth factors IGF-1 and IGF-2 in infantile autism. Dev Med Child Neurol. 2006; 48:751-755.*
Steiner T & Hacke W. Combination therapy with neuroprotectants and thrombolytics in acute ischaemic stroke. Eur. Neurol. 1998; 40(1):1-8.*
Tsai S-J. The possible role of tissue-type plasminogen activator and the plasminogen system in the pathogenesis of major depression. Med Hypotheses, 2006; 66:319-322.*

(Continued)

*Primary Examiner* — Kimberly A Ballard
(74) *Attorney, Agent, or Firm* — Wolf, Greenfield & Sacks, P.C.

(57) ABSTRACT

The present invention provides methods for identifying genes and pathways involved in plasticity. The invention applies some of these methods to identify genes that are differentially regulated in at least a portion of the nervous system of an individual subjected to conditions known to result in altered nervous system plasticity, i.e., dark rearing (DR) or monocular deprivation (MD). The genes are targets for pharmacological agents that modify plasticity. The invention also identifies biological pathways that are enriched in genes that are differentially regulated under conditions known to result in altered nervous system plasticity. The present invention further provides methods and compositions for modifying plasticity in the nervous system of a subject. The invention includes a method for modifying plasticity in the nervous system of a subject comprising administering a plasticity-modifying agent to the subject, wherein the plasticity-enhancing agent modulates a gene or pathway that is differentially regulated in developmental conditions that alter nervous system plasticity (e.g., DR or MD). The methods and compositions may be administered to a subject suffering from damage to the nervous system or from a neuropsychiatric disorder in order to enhance recovery, reorganization, or function of the nervous system. The methods optionally include administering a proteolysis-enhancing agent to the subject.

9 Claims, 7 Drawing Sheets

(56) References Cited

U.S. PATENT DOCUMENTS

| | | | |
|---|---|---|---|
| 6,153,211 | A | 11/2000 | Hubbell et al. |
| 6,261,837 | B1 | 7/2001 | Levinson et al. |
| 6,263,237 | B1 | 7/2001 | Rise |
| 6,284,247 | B1 | 9/2001 | Goeddel et al. |
| 6,503,947 | B1 * | 1/2003 | Lipton et al. ............... 514/575 |
| 6,514,937 | B1 * | 2/2003 | Mascarenhas ............ 514/8.5 |
| 6,808,522 | B2 | 10/2004 | Richards et al. |
| 6,858,229 | B1 | 2/2005 | Hubbell et al. |
| 2002/0072784 | A1 | 6/2002 | Sheppard, Jr. et al. |
| 2002/0160471 | A1 | 10/2002 | Kisiday et al. |
| 2003/0108923 | A1 | 6/2003 | Tuschl et al. |
| 2003/0219431 | A1 * | 11/2003 | Petti et al. ............... 424/94.64 |
| 2003/0236244 | A1 | 12/2003 | Ledford |
| 2004/0097504 | A1 | 5/2004 | Bethiel et al. |
| 2004/0166140 | A1 | 8/2004 | Santini, Jr. et al. |
| 2004/0176385 | A1 | 9/2004 | Nuss et al. |
| 2004/0209799 | A1 | 10/2004 | Vasios |
| 2004/0259248 | A1 | 12/2004 | Tuschl et al. |
| 2005/0026278 | A1 | 2/2005 | Tuschl et al. |
| 2005/0148574 | A1 | 7/2005 | Aronov et al. |
| 2005/0149000 | A1 | 7/2005 | Santini et al. |
| 2005/0234513 | A1 | 10/2005 | Alexander et al. |
| 2005/0272682 | A1 | 12/2005 | Evers et al. |
| 2006/0104969 | A1 | 5/2006 | Oray et al. |
| 2009/0099077 | A1 | 4/2009 | Sur et al. |
| 2010/0298304 | A1 | 11/2010 | Page et al. |

FOREIGN PATENT DOCUMENTS

| | | |
|---|---|---|
| WO | WO 01/58476 | 8/2001 |
| WO | WO-2006/023530 A2 | 3/2006 |

OTHER PUBLICATIONS

Ito M et al. (2006) Involvement of tissue plasminogen activator-plasmin system in depolarization-evoked dopamine release in the nucleus accumbens of mice. Mol. Pharmacol. 70(5):1720-1725.*
Abdelhaleem, M. "Do Human RNA Helicases Have a Role in Cancer?". Biochim Biophys Acta 1704, 37-46 (2004).
Akil, H., et al. "The Future of Psychiatric Research: Genomes and Neural Circuits". Science. Mar. 26, 2010;327(5973):1580-1.
Al-Anazi A, Bernstein M (2000). Modified stereotactic insertion of the Ommaya reservoir. J Neurosurg, 92:1050-1052.
Angelucci, A. et al. "Modifiability of neocortical connections and function during development". In: "The Mutable Brain", J.H. Kaas, ed, Harwood Academic Publishers, pp. 351-392, 2000.
Aniruddha Das "Cortical Maps: Where Theory Meets Experiments". Neuron 47: 168-171, 2005.
Ashburner, M., et al. "On Ontologies for Biologists: The Gene Ontology—Untangling the Web". Novartis Found Symp 247, 66-80, discussion 80-3, 84-90, 244-52 (2002).
Asselbergs, et al., (1995) J. Biotechnol., 42(3):221-233.
Banerjee A. et al. "Rett syndrome: genes, synapses, circuits and therapeutics." Front. Psychiatry Mar. 2012; 3:34.
Barnes, P., et al. "Proteolysis of proBDNF is a Key Regulator in the Formation of Memory". PLoS One. Sep. 24, 2008;3(9):e3248.
Basso, DM, et al., (1995). A sensitive and reliable locomotor rating scale for open field testing in rats. J. Neurotrauma, 12(1):1-21.
Basso, DM., et al. (1996). Graded histological and locomotor outcomes after spinal cord contusion using the NYU weight-drop device versus transection. Exp. Neurol., 139(2): 244-256.
Bear, M.F., Kleinschmidt, A., Gu, Q.A. & Singer, W. Disruption of experience-dependent synaptic modifications in striate cortex by infusion of an NMDA receptor antagonist. J Neurosci 10, 909-25 (1990).
Benevento, L.A., et al. "Gamma-Aminobutyric Acid and Somatostatin Immunoreactivity in the Visual Cortex of Normal and Dark-Reared Rats". Brain Res 689, 172-82 (1995).
Benita et al. (1984) J. Pharm. Sci. 73:1721-1724.
Bentley, et al. "Pharmcological Treatment of Ischemic Stroke". Pharmacol Therap. Dec. 2005, vol. 108, No. 3, pp. 334-352.

Berardi, N., et al. "Molecular Basis of Plasticity in the Visual Cortex". Trends Neurosci 26, 369-378 (2003).
Berry, M., et al., (2001) Gene therapy for central nervous system repair, Curr. Opin. Mol. Ther. 3: 338-49.
Bizik, J., et al. (1990) Cell Regul.; 1(12): 895-905.
Blair, L.A. & Marshall, J. IGF1 modulates N and L calcium channels in a PI 3-kinase-dependent manner. Neuron 19, 421-9 (1997).
Blue, M. E., and Parnavelas, J. G. (1983). The formation and maturation of synapses in the visual cortex of the rat. II. Quantitative analysis. J Neurocytol 12, 697-712.
Bondy, C.A. & Cheng, C.M. Insulin-like growth factor-1 promotes neuronal glucose utilization during brain development and repair processes. Int Rev Neurobiol 51, 189-217 (2002).
Bondy, C.A. & Cheng, C.M. Signaling by insulin-like growth factor 1 in brain. Eur J Pharmacol 490, 25-31 (2004).
Brody EN, Gold L. (2000) J Biotechnol., 74(1):5-13.
Brummelkamp, T.R., et al. (2002) A system for stable expression of short interfering RNAs in mammalian cells. Science 296:550-553.
Bunge, MB and Pearse, DD (2003) J Rehabil Res Dev. 40(4 Suppl 1):55-62.
Burns, A. & Zaudig, M., Mild cognitive impairment in older people. The Lancet 360, 1963-1965 (2002).
Chen et al. "Statins Induce Angiogenesis, Neurogenesis, and Synaptogenesis After Stroke". Ann Neurol. Jun. 2003, vol. 53, No. 6, pp. 743-751, especially abstract.
Corriveau, R.A., Huh, G.S. & Shatz, C.J. Regulation of class I MHC gene expression in the developing and mature CNS by neural activity. Neuron 21, 505-20 (1998).
Cotten and Birnstiel, (1989) EMBO J. 8:3861-3866.
Crair, M.C., et al. "The Role of Visual Experience in the Development of Columns in Cat Visual Cortex". Science 279, 566-70 (1998).
Cramer SC et al. "Harnessing neuroplasticity for clinical applications" Brain (2011) 134(6): 1591-1609 first published online Apr. 10, 2011 doi:10.1093/brain/awr039.
Cramer, S., et al. (1997) A functional MRI study of subjects recovered from hemiparetic stroke, Stroke, 28: 2518-2527.
Cronin, B. et al. "Hierarchical Bayesian modeling and Markov chain Monte Carlo sampling for tuning curve analysis". J Neurophysiol. Jan. 2010; 103(1):591-602.
Crowley, J.C., et al. "Early Development of Ocular Dominance Columns". Science 290, 1321-4 (2000).
Das, A., "Cortical Maps: Where Theory Meets Experiments", Neuron. 47:(2):168-171 (2005).
Dang W, Daviau T, Brem H. Morphological characterization of polyanhydride biodegradable implant gliadel during in vitro and in vivo erosion using scanning electron microscopy. Pharm Res, 13:683-91 (1996).
De Felipe, J., Marco, P., Fairen, A., and Jones, E. G. (1997). Inhibitory synaptogenesis in mouse somatosensory cortex. Cereb Cortex 7, 619-634.
DeVivo, M.J., Epidemiology of traumatic spinal cord injury, in Kischblum, S., Campagnolo, D.I., DeLlisa, J.A. (eds.) Spinal Cord Medicine, 2002. Lippincott Williams & Wilkins, Philadelphia, pp. 69-81.
Dityatev, A., and Schachner, M., Extracellular matrix molecules and synaptic plasticity. Nat Rev Neurosci 4, 456-468.
Dluzniewska, J., et al. "A Strong Neurorotective Effect of the Autonomous C-Terminal Peptide of IGF-1 Ec (MGF) in Brain Ischemia". The Faseb Jour. Sep. 2005, vol. 19, No. 11, pp. 1-21, especially abstract.
Dölen, G., et al. "Correction of Fragile X Syndrome in Mice". Neuron. Dec. 20, 2007;56(6):955-62.
Dragoi V. "Image Structure at the Center of Gaze during Free Viewing". Journal of Cognitive Neuroscience 18:737-748, 2006.
Dragoi, V. et al. "Adaptation-induced plasticity of orientation tuning in primary visual cortex". Neuron 28:287-298, 2000.
Dragoi, V. et al. "Contributions of ascending thalamic and local intracortical connections to visual cortical function". "Virtual Lesions: Understanding perception and behavior with reversible deactivactivation techniques", S. Lomber and R. Galuske, eds., Oxford University Press, pp. 41-60, 2002.

(56) References Cited

OTHER PUBLICATIONS

Dragoi, V. et al. "Dynamic properties of recurrent inhibition in primary visual cortex: Contrast and orientation dependence of contextual effects". J. Neurophysiol. 83: 1019-1030, 2000.

Dragoi, V. et al. "Dynamics of neuronal selectivity in primate visual cortex underlying local feature discrimination". Nature Neuroscience . 5: 883-891, 2002.

Dragoi, V. et al. "Foci of orientation plasticity in visual cortex". Nature 411: 80-86, 2001.

Dragoi, V. et al. "Plasticity of orientation processing in adult visual cortex". "The Visual Neurosciences", L.M. Chalupa and J.S. Werner,eds., MIT Press, 1654-1664, 2003.

Dragoi, V. et al. "Response plasticity in primary visual cortex and its role in vision and visuomotor behavior: Bottom up and top-down influences of orientation processing in adult visual cortex." IETE Journal of Research 49: 77-85, 2003.

Dragoi, V. et al. "Stability of cortical responses and the statistics of natural scenes". Neuron 32: 1181-1192, 2001.

Callaway, Edward M., "Orientation tuning—a crooked path to the straight and narrow". Neuron 5:783-785, 2002.

Elbashir, SM, et al., (2001) Duplexes of 21-nucleotide RNAs mediate RNA interference in cultured mammalian cells. Nature. 24;411(6836):494-8.

Ellsworth, C.A. et al. "Ephrin-A2 and -A5 influence patterning of normal and novel retinal projections to the thalamus: Conserved mapping mechanisms in visual and auditory thalamic targets". The Journal of Comparative Neurology 488: 140-151, 2005.

Elokdah H, et al. (2004) Tiplaxtinin, a novel, orally efficacious inhibitor of plasminogen activator inhibitor-1: design, synthesis, and preclinical characterization. J Med Chem. 47(14):3491-4.

Emptage, N., Bliss, T. V., and Fine, A. (1999). Single synaptic events evoke NMDA receptor-mediated release of calcium from internal stores in hippocampal dendritic spines. Neuron 22, 115-124.

Engert, F., and Bonhoeffer, T. (1999). Dendritic spine changes associated with hippocampal long-term synaptic plasticity. Nature 399, 66-70.

Fagiolini, M., and Hensch, T. K. (2000). Inhibitory threshold for critical-period activation in primary visual cortex. Nature 404, 183-186.

Fagiolini, M., et al. "Functional Postnatal Development of the Rat Primary Visual Cortex and the Role of Visual Experience: Dark Rearing and Monocular Deprivation". Vision Res 34, 709-20 (1994).

Fagiolini, M., Fritschy, J. M., Low, K., Mohler, H., Rudolph, U., and Hensch, T. K. (2004). Specific GABAA circuits for visual cortical plasticity. Science 303, 1681-1683.

Farley B.F. et al. "Alteration of Visual Input Results in a Coordinated Reorganization of Multiple Visual Cortex Maps" The Journal of Neuroscience 27:10299-10310, 2007.

Fawcett, JW and Asher, RA (1999)The glial scar and central nervous system repair. Brain Res Bull. 49(6):377-91.

Feng, G., Mellor, R. H., Bernstein, M., Keller-Peck, C., Nguyen, Q. T., Wallace, M., Nerbonne, J. M., Lichtman, J. W., and Sanes, J. R. (2000). Imaging neuronal subsets in transgenic mice expressing multiple spectral variants of GFP. Neuron 28, 41-51.

Fischer, M., Kaech, S., Knutti, D., and Matus, A. (1998). Rapid actin-based plasticity in dendritic spines. Neuron 20, 847-854.

Fischer, M., Kaech, S., Wagner, U., Brinkhaus, H., and Matus, A. (2000). Glutamate receptors regulate actin-based plasticity in dendritic spines. Nat Neurosci 3, 887-894.

Fiumelli, H., Jabaudon, D., Magistretti, P. J., and Martin, J. L. (1999). BDNF stimulates expression, activity and release of tissue-type plasminogen activator in mouse cortical neurons. Eur J Neurosci 11, 1639-1646.

Fleming AB, Saltzman WM (2002). Pharmacokinetics of the carmustine implant. Clin Pharmackinet, 41:403-19.

Fukazawa, Y., Saitoh, Y., Ozawa, F., Ohta, Y., Mizuno, K., and Inokuchi, K. (2003). Hippocampal LTP Is Accompanied by Enhanced F-Actin Content within the Dendritic Spine that Is Essential for Late LTP Maintenance In Vivo. Neuron 38, 447-460.

Furlan, M., et al., (1996) Spontaneous neurological recovery after stroke and the fate of the ischemic penumbra, Ann. Neurol., 40:216-226.

Gale K, Kerasidis H, Wrathall JR (1985) Spinal cord contusion in the rat: behavioral analysis of functional neurological impairment. Exp. Neurol 88:123-134.

Galicich JH, Guido LJ (1974). Ommaya device in carcinomatous and leukemic meningitis. Surgical experience in 45 cases. Surg Clin North Am 54:915-922.

Ge, T., et al., (2005) Cloning of thrombolytic enzyme (lumbrokinase) from earthworm and its expression in the yeast *Pichia pastoris*. Protein Expr Purif. Jul. 2005;42(1):20-8.

George, P. et al. Fabrication and biocompatibility of polypyrrole implants suitable for neural prosthetics. Biomaterials 26: 3511-3519, 2005.

Gils, A., et al. (2002) Characterization and comparative evaluation of a novel PAI-1 inhibitor. Thromb Haemost. 88(1):137-43.

Goldman S., Stem and progenitor cell-based therapy of the human central nervous system. Nat Biotechnol. 23(7):862-71 (2005).

Gordon, J. A., and Stryker, M. P. (1996). Experience-dependent plasticity of binocular responses in the primary visual cortex of the mouse. Journal of Neuroscience 16, 3274-3286.

Gorlin et al. Imaging prior information in the brain. PNAS 109(20):7935-7940 (2012).

Gray, E., Electron microscopy of synaptic contacts on dendritic spines of the cerebral cortex. Nature 183, 1592-1593 (1959).

Guan, J., Bennet, L., Gluckman, P.D. & Gunn, A.J. Insulin-like growth factor-1 and post-ischemic brain injury. Prog Neurobiol 70, 443-62 (2003).

Guo, JT, et al., "PROSPECT-PSPP: an automatic computational pipeline for protein structure prediction". Nucleic Acids Res. 32 (Web Server issue): W522-5, Jul. 1, 2004).

Gupta, YK and Briyal, S., (2004) Animal models of cerebral ischemia for evaluation of drugs. Indian J Physiol Pharmacol. 48(4):379-94.

Hall, A. (1998). Rho GTPases and the actin cytoskeleton. Science 279, 509-514. Han, S.-O., R.I. Mahato, Y.K. Sung, and S.W. Kim. (2000) Development of Biomaterials for gene therapy. Mol. Therapy 2:302-317.

Han, S. et al., "Development of Biomaterials for Gene Therapy" Molecular Therapy, 2:(4):302-317 (2000).

Harenberg, (1998), Med. Res. Rev., 18:1-20.

Heinemann U., et al., (2001); Curr Opin Biotechnol.12(4):348-54.

Hennan JK (2005) Evaluation of PAI-039 [{1-Benzyl-5-[4-(trifluoromethoxy)phenyl]-1H-indo1-3-yl}(oxo)acetic Acid], a Novel Plasminogen Activator Inhibitor-1 Inhibitor, in a Canine Model of Coronary Artery Thrombosis. Pharmacol Exp Ther. 314(2):710-6.

Hensch, T.K. & Stryker, M.P. Columnar architecture sculpted by GABA circuits in developing cat visual cortex. Science 303, 1678-81 (2004).

Hensch, T.K. "Critical Period Regulation". Annu Rev Neurosci 27, 549-579 (2004).

Hensch, T.K. et al. Local GABA circuit control of experience-dependent plasticity in developing visual cortex. Science 282, 1504-8 (1998).

Hering, H., and Sheng, M., Dendritic spines: structure, dynamics and regulation. Nat Rev Neurosci 2, 880-888 (2001).

Heynen, A. J., Yoon, B. J., Liu, C. H., Chung, H. J., Huganir, R. L., and Bear, M. F. (2003). Molecular mechanism for loss of visual cortical responsiveness following brief monocular deprivation. Nat Neurosci 6, 854-862.

Higgins DL and Bennett WF, (1990) Tissue Plasminogen Activator: The Biochemistry and Pharmacology of Variants Produced by Mutagenesis. Annual Review of Pharmacology and Toxicology vol. 30: 91-121.

Hohnke, C.D. et al. "Activity-dependent patterning of retinogeniculate axons proceeds with a constant contribution from AMPA and NMDA receptors". J. Neuroscience 20: 8051-8060, 2000.

Hohnke, C.D. et al. "Neural activity and the development of brain circuits". In: Encyclopedia of Life Sciences, London: Nature Publishing Group, vol. 13, pp. 19-27, 2001.

(56) References Cited

OTHER PUBLICATIONS

Horng, S. et al. "Patterning and Plasticity of Maps in the Mammalian Visual Pathway". In "The Cognitive Neurosciences, 4th Edition," ed. M.S. Gazzaniga, MIT Press, pp. 91-107, 2009.
Horng, S.et al. "Differential gene expression in the developing lateral geniculate nucleus and medial geniculate nucleus reveals novel roles for Zic4 and Foxp2 in visual and auditory pathway development". Journal of Neuroscience 29(43): 13672-13683, 2009.
Horng, S.H. et al. "Visual activity and cortical rewiring: activity-dependent plasticity of cortical networks". Progress in Brain Research 157:3-11, 2006.
Huang, Z.J. et al. BDNF regulates the maturation of inhibition and the critical period of plasticity in mouse visual cortex. Cell 98, 739-55 (1999).
Hubel, D. H., and Wiesel, T. N. (1970). The period of susceptibility to the physiological effects of unilateral eye closure in kittens. J Physiol 206, 419-436.
International Preliminary Report on Patentability for PCT/US2007/009172, issued on Nov. 27, 2008 (8 pages).
International Search Report for PCT/US2007/009172, mailed on Oct. 8, 2008 (6 pages).
Iwadate, H., Sugisaki, T., Kudo, M. & Kizuki, K. Actions of insulin-like growth factor binding protein-5 (IGFBP-5) are potentially regulated by tissue kallikrein in rat brains. Life Sci 73, 3149-58 (2003).
Jarosiewicz B. et al. "Functional Biases in Visual Cortex Neurons with Identified Projections to Higher Cortical Targets". Current Biology Feb. 21, 2012; 22: 269-277.
Jin, D.Z. et al. "Tilt after effect and adaptation-induced changes in orientation tuning in visual cortex". Journal of Neurophysiology 94:4038-4050, 2005.
Justicia, C., Gabriel, C. & Planas, A.M. Activation of the JAK/STAT pathway following transient focal cerebral ischemia: signaling through Jak1 and Stat3 in astrocytes. Glia 30, 253-70 (2000).
Kalkman, H.O., et al. "The Role of the Phosphatidylinositide 3-Kinase-Protein Kinase B Pathway in Schizophrenia". Pharmacol Ther. Apr. 2006;110(1):117-34. Epub Jan. 23, 2006.
Kanematsu, A., et al., Collagenous matrices as release carriers of exogenous growth factors. Biomaterials. 25(18):4513-20 (2004).
Kesslak JP, Keirstead HS. (2003) Assessment of behavior in animal models of spinal cord injury. J Spinal Cord Med. 26(4):323-8.
Kirkwood, A., et al. "Experience-Dependent Modification of Synaptic Plasticity in Visual Cortex". Nature 381, 526-8 (1996).
Krueger K, Busch E. Protocol of a thromboembolic stroke model in the rat: review of the experimental procedure and comparison of models. Invest Radiol. 2002. 37(11):600-8.
Krystosek, A., and Seeds, N. W. (1981). Plasminogen activator release at the neuronal growth cone. Science 213, 1532-1534.
Lachance, P.E., et al. "Microarray Analysis of Developmental Plasticity in Monkey Primary Visual Cortex". J Neurochem 88, 1455-69 (2004).
Larner TJ (1994). Treatment of cancer-related pain: when orally administered medications fail. Mayo Clin Proc, 69:473-80.
Laske, DW, et al., 1997 Nat. Med. Tumor regression with regional distribution of the targeted toxin TF-CRM107 in patients with malignant brain tumors.3(12):1362-8.
Laurino, L. et al. PI3K activation by IGF1 is essential for the regulation of membrane expansion at the nerve growth cone. J Cell Sci 118, 3653-62 (2005).
Leamey C.A. et al. "Differential Gene Expression between Sensory Neocortical Areas: Potential Roles for Ten_m3 and Bcl6 in Patterning Visual and Somatosensory Pathways". Cerebral Cortex 2008.
Leamey C.A. et al. "Ten_m3 Regulates Eye-Specific Patterning in the Mammalian Visual Pathway and is Required for Binocular Vision". PLoS Biology 5:2077-2092, 2007.
Leamey, C. et al. "Development and plasticity of cortical areas and networks". Nature Reviews Neurosci. 2:251-262, 2001.
Leamey, C. et al. "Disruption of retinogeniculate pattern formation by inhibition of soluble guanylyl cyclase". J. Neuroscience 21(11): 3871-3880, 2001.
Leamey, C.A. et al. "Intrinsic patterning and experience-dependent mechanisms that generate eye-specific projections and binocular circuits in the visual pathway". Current Opinion in Neurobiology 19:181-187. 2009.
Leamey, C.A. et al. "The role of calcineurin in activity dependent pattern formation in the dorsal lateral geniculate nucleus of the ferret". Journal of Neurobiology 56: 153-162, 2003.
Leamey, C.A. et al. "The thalamus: A new proposal". Neuron 34: 507-508, 2002.
Lendvai, B., Stern, E. A., Chen, B., and Svoboda, K. (2000). Experience-dependent plasticity of dendritic spines in the developing rat barrel cortex in vivo. Nature 404, 876-881.
Lewis, D.A. et al. Cortical parvalbumin interneurons and cognitive dysfunction in schizophrenia.Trends Neurosci. Jan. 2012;35(1):57-67. Epub Dec. 6, 2011.
Liang, A., et al., (2005) Characterization of a small molecule PAI-1 inhibitor, ZK4044. Thromb Res. 115(4):341-50. Epub Nov. 13, 2004.
Liou, J.C., Tsai, F.Z. & Ho, S.Y. Potentiation of quantal secretion by insulin-like growth factor-1 at developing motoneurons in *Xenopus* cell culture. J Physiol 553, 719-28 (2003).
Lodovichi, C., Berardi, N., Pizzorusso, T. & Maffei, L. Effects of neurotrophins on cortical plasticity: same or different? J Neurosci 20, 2155-65 (2000).
Lund, J.S., et al. "Local Circuit Neurons of Developing and Mature Macaque Prefrontal Cortex: Golgi and Immunocytochemical Characteristics". J Comp Neurol 328, 282-312 (1993).
Lyckman A.W. et al. "Gene expression patterns in visual cortex during the critical period: synaptic stabilization and reversal by visual deprivation". Proc Natl Acad Sci U S A. 105(27):9409-14. 2008.
Lyckman, A. et al. "Enhanced plasticity of retinothalamic projections in an ephrin-A2/A5 double mutant". J. Neuroscience 21(19): 7684-7690, 2001.
Lyckman, A. et al. "The role of afferent activity in the development of cortical specification". "Results and Problems in Cell Differentiation, vol. 39 ", C. Hohmann, ed., Springer-Verlag, pp. 139-156, 2002.
Lyckman, A.W. et al. "Normal eye-specific patterning of retinal inputs to murine subcortical visual nuclei in the absence of brain-derived neurotrophic factor". Visual Neuroscience 22:27-36, 2005.
Machado M, Salcman M, Kaplan RS, Montgomery E (1985). Expanded role of the cerebrospinal fluid reservoir in neuroongocology: indications, causes of revision, and complications. Neurosurgery 17:600-603.
Maffei, L., Berardi, N., Domenici, L., Parisi, V. & Pizzorusso, T. Nerve growth factor (NGF) prevents the shift in ocular dominance distribution of visual cortical neurons in monocularly deprived rats. J Neurosci 12, 4651-62 (1992).
Majewska A. et al. "Plasticity and specificity of cortical processing networks". Trends in Neuroscience 29:323-329, 2006.
Majewska, A. et al. "Motility of dendritic spines in visual cortex in vivo: changes during the critical period and effects of visual deprivation." Proceedings of the National Academy of Sciences 100: 16024-16029, 2003.
Majewska, A., Brown, E., Ross, J., and Yuste, R. (2000a). Mechanisms of calcium decay kinetics in hippocampal spines: role of spine calcium pumps and calcium diffusion through the spine neck in biochemical compartmentalization. J Neurosci 20, 1722-1734.
Majewska, A., Tashiro, A., and Yuste, R. (2000b). Regulation of spine calcium dynamics by rapid spine motility. J Neurosci 20, 8262-8268.
Maletic-Savatic, M., Malinow, R., and Svoboda, K. (1999). Rapid dendritic morphogenesis in CA1 hippocampal dendrites induced by synaptic activity. Science 283, 1923-1927.
Malik WQ et al. "Denoising Two-Photon Calcium Imaging Data". PLoS One 2011 6(6):e20490. doi:10.1371/journal.pone.0020490.
Malik, W. et al. "A Statistical Model for Multiphoton Calcium Imaging of the Brain". 31st Annual International Conference of the IEEE EMBS, Minneapolis, Minnesota, USA, Sep. 2-6, 2009.
Mao R. et al. "Influence of a Subtype of Inhibitory Interneuron on Stimulus-Specific Responses in Visual Cortex". Cereb Cortex. Jun. 24, 2011. PMID: 21666125.
Mao, R. et al. "Reduced conditioned fear response in mice that lack /Dlx1/ and show subtype-specific loss of interneurons". Journal of Neurodevelopmental Disorders 1:224-236. 2009.

(56) References Cited

OTHER PUBLICATIONS

Mariño, J. et al. "Invariant computations in local cortical networks with balanced excitation and inhibition". Nature Neuroscience 8: 194-201, 2005.
Marino, J., Schummers et al. "Combinacion de nuevas tecnicas electrofisiologicas y de imagen en el estudio" de la funcion de la coteza visual primaria. Revisitia de Nuerologica 36: 944-950, 2003 (English Abstract Only).
Martinez-Arizala A. (2003) Methods to measure sensory function in humans versus animals. J Rehabil Res Dev. 40(4 Suppl 1):35-9.
Mataga N, Mizuguchi Y, Hensch TK (2004) Experience-dependent pruning of dendritic spines in visual cortex by tissue plasminogen activator. Neuron 44:1031-1041.
Mathiowitz and Langer (1987) J. Controlled Release 5:13-22.
Mathiowitz et al. (1987) Reactive Polymers 6:275-283.
Mathiowitz et al. (1988) J. Appl. Polymer Sci. 35:755-774.
Mathiowitz et al. (1990) Scanning Microscopy 4:329-340.
Mathiowitz et al. (1992) J. Appl. Polymer Sci., 45:125-134.
McCurry CL et al. "Loss of Arc renders the visual cortex impervious to the effects of sensory experience or deprivation". Nat Neurosci. Apr. 2010;13(4):450-7.
McGee, A.W., Yang, Y., Fischer, Q.S., Daw, N.W. & Strittmatter, S.M. Experience-driven plasticity of visual cortex limited by myelin and Nogo receptor. Science 309, 2222-6 (2005).
McKinney, R. A., Capogna, M., Dürr, R., and Gähwiler, B. H. (1999). Miniature synaptic events maintain dendritic spines via AMPA receptor activation. Nature Neuroscience 2, 44-49.
McManus, M.T., and P.A. Sharp. (2002) Gene silencing in mammals by short interfering RNAs. Nature Rev. Genetics. 3:737-747.
Mellios N, Sur M., "The emerging role of microRNAs in schizophrenia and autism spectrum disorders". Front. Psychiatry Apr.; 3:39 (2012).
Mellios N. et al. "miR-132, an experience-dependent microRNA, is essential for visual cortex plasticity". Nature Neuroscience 2011. doi:10.1038/nn.2909.
Merlin S et al. "Deletion of Ten-m3 Induces the Formation of Eye Dominance Domains in Mouse Visual Cortex". Cerebral Cortex 2012; doi:10.1093/cercor/bhs030.
Milwidsky, et al. (1991), Thrombo. Haemostat., 65:389-393.
Mower AF et al. "Experience-dependent regulation of CaMKII activity within single visual cortex synapses in vivo". Proc Natl Acad Sci U S A. Dec. 12, 2011.
Muller, C. M., and Griesinger, C. B. (1998). Tissue plasminogen activator mediates reverse occlusion plasticity in visual cortex. Nat Neurosci 1, 47-53.
Murray, K.D., et al. "N-Methyl-D-Aspartate Receptor Dependent Transcriptional Regulation of Two Calcium/Calmodulin-Dependent Protein Kinase Type II Isoforms in Rodent Cerebral Cortex". Neuroscience 122, 404-20 (2003).
Neville, H.et al. "Introduction to Plasticity". In "The Cognitive Neurosciences, 4th Edition," ed. M.S. Gazzaniga, MIT Press, pp. 89-91, 2009.
Newton J.R. et al. "Developmental studies on rewiring the brain: What they tell us about brain evolution". In: Evolution of Nervous Systems, ed. J.H. Kaas, Academic Press, Oxford, vol. 3, pp. 103-112, 2007.
Newton J.R. et al. "Reprogramming cortex: the consequences of cross-modal plasticity during development". In: Reprogramming the Cerebral Cortex, ed., S. Lomber and J. Eggermont, Oxford University Press, pp. 349-360, 2006.
Newton, J.R et al. "Plasticity of cerebral cortex in development". Encyclopedia of Neuroscience, 2004.
Newton, J.R. et al. "Acceleration of visually cued conditioned fear through the auditory pathway". Nature Neuroscience 7: 968-973, 2004.
Newton, J.R. et al. "Rewiring cortex functional visual plasticity in the auditory cortex during development". In "Plasticity of the central auditory system and processing of complex acoustic signals" ed., J. Syka and M.M. Merzenich, 2004.

Nishiyama M, et al., (2003) Cyclic AMP/GMP-dependent modulation of Ca2+ channels sets the polarity of nerve growth-cone turning. Nature. 423(6943):990-5.
Noble LJ, Wrathall JR (1985) Spinal cord contusion in the rat: morphometric analyses of alterations in the spinal cord. Exp Neurol 88:135-149.
Noble LJ, Wrathall JR (1989a) Correlative analysis of lesion development and functional status after graded spinal cord contusive injuries in the rat. Exp Neurol 103:34-40.
Noble LJ, Wrathall JR (1989b) Distribution and time course of protein extravasation in the spinal cord after contusive injury. Brain Res 482:57-66.
Obata, S., Obata, J., Das, A. & Gilbert, C.D. Molecular correlates of topographic reorganization in primary visual cortex following retinal lesions. Cereb Cortex 9, 238-48 (1999).
Obbens EAMT, Leavents ME, Beal JW, Lee YY (1985). Ommaya reservoirs in 387 cancer patients: a 15-year experience. Neurology 35:1274-1278.
Olson, C. R., and Freeman, R. D. (1975). Progressive changes in kitten striate cortex during monocular vision. J Neurophysiol 38, 26-32.
Ommaya AK, Punjab MB (1963). Subcutaneous reservoir and pump for sterile access to ventricular cerebrospinal fluid. Lancet, 2:983-984.
Oray S. et al. "Effects of Synaptic Activity on Dendritic Spine Motility of Developing Cortical Layer V Pyramidal Neurons". Cerebral Cortex 16:730-741, 2006.
Oray, S. et al. "Dendritic spine dynamics are regulated by monocular deprivation and extracellular matrix degradation". Neuron 44: 1021-1030, 2004.
Ossipow, V., et al. "Gene Expression Analysis of the Critical Period in the Visual Cortex". Mol Cell Neurosci 27, 70-83 (2004).
Paez, J. and Sellers, W., Cancer Treat Res. 115:145-67 (2003).
Page D.T. et al. "Haploinsufficiency for Pten and Serotonin transporter cooperatively influences brain size and social behavior". Proc Natl Acad Sci U S A. 106:1989-1994. 2009.
Page DT et al. "Computerized assessment of social approach behavior in mouse". Front Behav Neurosci. Nov. 30, 2009;3:48.
Paice JA, Penn RD, Shott S (1996). Intraspinal morphine for chronic pain: a retrospective, multicenter study. J Pain Symptom Manage, 11:71-80.
Panjabi M, Wrathall JR (1988) Biomechanical analysis of spinal cord injury and functional loss. Spine 13:1365-1370.
Papadopoulos, G.C., et al. "Postnatal Development of Somatostatin-Containing Neurons in the Visual Cortex of Normal and Dark-Reared Rats". Exp Brain Res 92, 473-8 (1993).
Parkinnen (1993), J. Biol. Chem. 268: 19726-19738.
Pennica, D. et al., "Cloning and expression of human tissue-type plasminogen activator cDNA in *E.coli*", Nature, 301:(5897):214-221 (1983).
Petersen, R.C., et al., (2001). Current Concepts in Mild Cognitive Impairment. Arch. Neurol. 58, 1985-1992.
Pizzorusso, T. et al. Reactivation of ocular dominance plasticity in the adult visual cortex. Science 298, 1248-51 (2002).
Porciatti, V., Pizzorusso, T. & Maffei, L. The visual physiology of the wild type mouse determined with pattern VEPs. Vision Res 39, 3071-81 (1999).
Prasad, S.S., et al. "Gene Expression Patterns During Enhanced Periods of Visual Cortex Plasticity". Neuroscience 111, 35-45 (2002).
Qian, Z., Gilbert, M. E., Colicos, M. A., Kandel, E. R., and Kuhl, D. (1993). Tissue-plasminogen activator is induced as an immediate-early gene during seizure, kindling and long-term potentiation. Nature 361, 453-457.
Raines A, Dretc.hen KL, Marx K, Wrathall JR (1988) Spinal cord contusion in the rat: somatosensory evoked potentials as a function of graded injury. J Neurotrauma 5:151-160.
Ramos BP, et al., Dysregulation of protein kinase a signaling in the aged prefrontal cortex: new strategy for treating age-related cognitive decline. Neuron, 40(4):835-45.
Rivadulla, C. et al. "Specific roles of NMDA and AMPA receptors in direction-selective and spatial phase-selective responses in visual cortex". J. Neuroscience 21: 1710-1719, 2001.

(56) References Cited

OTHER PUBLICATIONS

Roberts LJ, Finch PM, Goucke CR, Price LM (2001). Outcome of intrathecal opioids in chronic non-cancer pain. Eur J Pain, 5:353-61.
Roberts, E.B., Meredith, M.A. & Ramoa, A.S. Suppression of NMDA receptor function using antisense DNA block ocular dominance plasticity while preserving visual responses. J Neurophysiol 80, 1021-32 (1998).
Runyan CA et al. "Response Features of Parvalbumin-Expressing Interneurons Suggest Precise Roles for Subtypes of Inhibition in Visual Cortex". Neuron Sep. 9, 2010, 67(5):847-857.
Sakata, et al. (1999), Am. Heart J., 137:1094-1099.
Sali, A. and Blundell, TL, (1993) J. Mol. Biol., 234, 779-815.
Santini, JT, et al. (2000) Microchips as Controlled Drug-delivery Devices. Angewandte Chemie, International Edition, vol. 39, pp. 2396-2407.
Sawtell, N. B., Frenkel, M. Y., Philpot, B. D., Nakazawa, K., Tonegawa, S., and Bear, M. F. (2003). NMDA Receptor-Dependent Ocular Dominance Plasticity in Adult Visual Cortex. Neuron 38, 977-985.
Schlaug, G., et al. (1999) The ischemic penumbra: operationally defined by diffusion and perfusion MRI. Neurology. 53(7):1528-37.
Schmidt, C.E. et al., "Neural tissue engineering: strategies for repair and regeneration". Annu. Rev. Biomed. Eng. 5:293-347 (2003).
Schummers J. et al. "Dynamics of orientation tuning in cat V1 neurons depend on location within layers and orientation maps" Frontiers in Neuroscience 1:145-159, 2007.
Schummers J. et al. "Tuned responses of astrocytes and their influence on hemodynamic signals in the visual cortex". Science 320(5883):1638-43, 2008.
Schummers, J. et al. "Bottom-up and top-down dynamics in visual cortex". Progress in Brain Research 149:65-81, 2005.
Schummers, J. et al. "Cortical plasticity: Time for a change" Current Biology 12: R168-R170, 2002.
Schummers, J. et al. "Local networks in visual cortex and their influence on neuronal responses and dynamics". Journal of Physiology Paris 98:429-441, 2005.
Schummers, J. et al. Synaptic integration by V1 neurons depends on location within the orientation map. Neuron 36: 969-978, 2002.
Schwaiger, F.W. et al. Peripheral but not central axotomy induces changes in Janus kinases (JAK) and signal transducers and activators of transcription (STAT). Eur J Neurosci 12, 1165-76 (2000).
Seshadri, S., et al. "Disrupted-in-Schizophrenia-1 Expression is Regulated by Beta-Site Amyloid Precursor Protein Cleaving Enzyme-1-Neuregulin Cascade". Proc Natl Acad Sci U S A. Mar. 23, 2010;107(12):5622-7. Epub Mar. 8, 2010.
Seto, D. et al. Insulin-like growth factor-I inhibits endogenous acetylcholine release from the rat hippocampal formation: possible involvement of GABA in mediating the effects. Neuroscience 115, 603-12 (2002).
Sharma, J. et al. "Induction of visual orientation modules in auditory cortex." Nature 404:841-847, 2000.
Sharma, J. et al. "V1 neurons signal acquisition of an internal representation of stimulus location". Science 300: 1758-1763, 2003.
Sizonenko, S.V., Sirimanne, E.S., Williams, C.E. & Gluckman, P.D. Neuroprotective effects of the N-terminal tripeptide of IGF1, glycine-proline-glutamate, in the immature rat brain after hypoxic-ischemic injury. Brain Res 922, 42-50 (2001).
Somers, D. et al. "Orientation selectivity and its modulation by local and long-range connections in visual cortex". "The Cat Primary Visual Cortex", A. Peters and B. Payne, eds., Academic Press, pp. 471-520, 2002.
Star, E. N., Kwiatkowski, D. J., and Murthy, V. N. (2002). Rapid turnover of actin in dendritic spines and its regulation by activity. Nat Neurosci 5, 239-246.
Stevenson IH et al. "Sensory Adaptation and Short Term Plasticity as Bayesian Correction for a Changing Brain". PLoS One 2010 5(8): e12436. doi:10.1371/journal.pone.0012436.
Stimberg, M. "The operating regime of local computations in primary visual cortex". Cerebral Cortex (advanced access e-publication Feb. 16, 2009).
Sur M. et al. "The Emerging Nature of Nurture" Science 322:1636. 2008.
Sur, M. "Breathing life into biology". Nature 436:487, 2005.
Sur, M. "Cortical development: Transplantation and rewiring studies". In: International Encyclopedia of the Social and Behavioral Sciences 4: 2837-2842, 2001.
Sur, M. "Rewiring cortex: Cross-modal plasticity and its implications for cortical development and function". "Handbook of Multisensory Processing", B. Stein, ed., MIT Press, 2004.
Sur, M. et al. "Cognitive science: sensation, perception and learning". Editorial, special issue on cognitive science, IETE Journal of Research 49: 73-75, 2003.
Sur, M. et al. "Patterning and plasticity of the cerebral cortex". Science 310:805-810, 2005.
Swaminathan, N. "Mysterious Brain Cells Linked to Blood Flow" Scientific American Jul. 20, 2008.
Sweet-Cordero, A. et al. An oncogenic KRAS2 expression signature identified by cross-species gene-expression analysis. Nat Genet 37, 48-55 (2005).
Tagawa, Y., et al. "Multiple Periods of Functional Ocular Dominance plasticity in Mouse Visual Cortex". Nat Neurosci 8, 380-8 (2005).
Takenaga, M., et al., (2004) Optimum formulation for sustained-release insulin. Int J Pharm. 271(1-2):85-94.
Teng YD, Wrathall JR (1996) Evaluation of cardiorespiratory parameters in rats after spinal cord trauma and treatment with NBQX, an antagonist of excitatory amino acid receptors. Neurosci Lett 209:5-8.
Thiselton, D.L., et al. "AKT1 is Associated with Schizophrenia Across Multiple Symptom Dimensions in the Irish Study of High Density Schizophrenia Families". Biol Psychiatry. Mar. 1, 2008;63(5):449-57. Epub Sep. 6, 2007.
Thomas CK, Noga BR. (2003) Physiological methods to measure motor function in humans and animals with spinal cord injury. J Rehabil Res Dev. 40(4 Suppl 1):25-33.
Thomas, N., and Klibanov, A.M. (2003) Non-viral gene therapy: polycation-mediated DNA delivery. Appl. Microbiol. Biotechnol. 62:27-34.
Tonner, E. et al. Insulin-like growth factor binding protein-5 (IGFBP-5) potentially regulates programmed cell death and plasminogen activation in the mammary gland. Adv Exp Med Biol 480, 45-53 (2000).
Toombs CF. (2001) Alfimeprase: pharmacology of a novel fibrinolytic metalloproteinase for thrombolysis. Haemostasis. 31(3-6):141-7.
Tropea D. et al. "Molecular mechanisms of experience-dependent plasticity in visual cortex" Phil Trans R Soc B 364:341-355, 2009. Published online Oct. 31, 2008.
Tropea D. et al. "Structural Dynamics of Synapses in Vivo Correlate with Functional Changes during Experience-Dependent Plasticity in Visual Cortex". J. Neurosci. 2010 30: 11086-11095; doi:10.1523/JNEUROSCI.1661-10.2010.
Tropea D. et al. Experience-dependent plasticity in visual cortex: Dendritic spines and visual responsiveness Commun Integr Biol. Mar.-Apr. 2011; 4(2): 216-219. doi: 10.4161/cib.4.2.14505.
Tropea, D., Capsoni, S., Covaceuszach, S., Domenici, L. & Cattaneo, A. Rat visual cortical neurones express TrkA NGF receptor. Neuroreport 13, 1369-73 (2002).
Tropea, D., et al. "Partial Reversal of Rett Syndrome-Like Symptoms in MeCP2 Mutant Mice". Proc Natl Acad Sci U S A. Feb. 10, 2009;106(6):2029-34.
Tutak U, Doleys DM (1996). Intrathecal infusion systems for treatment of chronic low back and leg pain of noncancer origin. South Med J, 89:295-300.
Usman, et al., (1996) Curr. Opin. Struct. Biol., 1:527.
Vemuganti et al. "Gene Expression Analysis of Spontaneously Hypertensive Rat Cerebral Cortex Following Transient Focal Cerebral Ischemia". Jour Neurochem. Dec. 2002, vol. 83, No. 5, pp. 1072-1086, the entire article.
Von Melchner et al. "Visual behavior mediated by retinal projections directed to the auditory pathway". Nature 404:871-876, 2000.
Wang K.H. et al. "In Vivo Two-Photon Imaging Reveals a Role of Arc in Enhancing Orientation Specificity in Visual Cortex". Cell 126:389-402, 2006.

(56) References Cited

OTHER PUBLICATIONS

Wang, W.F., Kiyosawa, M., Ishiwata, K. & Mochizuki, M. Glucose metabolism in the visual structures of rat monocularly deprived by eyelid suture after postnatal eye opening. Jpn J Ophthalmol 49, 6-11 (2005).
Webb, A.A. et al.m "Behavioural analysis of the efficacy of treatments for injuries to the spinal cord in animals", Vet Rec. 155:(8):225-30 (2004).
Welberg, L. "Astrocytes: More than meets the eye" Nature Reviews Neuroscience 9, 586, 2008.
Weng, J. et al. "Autonomous mental development by robots and animals". Science 291: 599-600, 2001.
Werb, Z. (1997). ECM and cell surface proteolysis: regulating cellular ecology. Cell 91, 439-442.
White (1998), J. Am. Coll. Cardiol., 31: 487-496.
White, L.E., Coppola, D.M. & Fitzpatrick, D. The contribution of sensory experience to the maturation of orientation selectivity in ferret visual cortex. Nature 411, 1049-52 (2001).
Wiesel, T. N., and Hubel, D. H. (1963). Single-Cell Responses in Striate Cortex of Kittens Deprived of Vision in One Eye. J Neurophysiol 26, 1003-1017.
Wilson N.R. et al. "Synaptic Reorganization in Scaled Networks of Controlled Size". Journal of Neuroscience 27 (50):13581, 2007.
Wilson NR et al. "Determinants of Synaptic and Circuit Plasticity in the Cerebral Cortex". In: Cerebral Plasticity: New Perspectives (Chalupa LM, ed, The MIT Press, Cambridge, MA), pp. 75-88, 2011.
Wimmer K. et al. "Dependence of orientation tuning on recurrent excitation and inhibition in a network model of V1". In Advances in Neural Information Processing Systems 21. (D. Koller, D. Schuurmans, Y. Bengio, and L. Bottou, editors, MIT Press), pp. 1769-1776, 2009.
Winkemuller M, Winkemuller W (1996). Long-term effects of continuous intrathecal opioid treatment in chronic pain of nonmalignant etiology. J Neurosurg, 85:458-467.
Wishart D., (2005) Curr Pharm Biotechnol., 6(2):105-20.
Wolf, F., and Kirchhoff, F. "Imaging Astrocyte Activity" Science 320: 1597-1599, 2008.
Woo, et al. "Regulation of Cortical Interneurons by Neurotrophins: From Development to Cognitive Disorders". The Neuroscientist. 2006, vol. 12, No. 1, pp. 43-56, the entire article.
Wrathall JR, Pettegrew R, Harvey F (1985) Spinal cord contusion in the rat: production of graded, reproducible injury groups. Exp Neurol 88:108-122.
Written Opinion for PCT/US2007/009172, mailed on Oct. 8, 2008 (6 pages).
Wu MP, Tamada JA, Brem H, Langer R (1994). In vivo versus in vitro degradation of controlled release polymers for intracranial surgical therapy. J Biomed Mater Res, 28:387-95.
Xu, W., Nair, J.S., Malhotra, A. & Zhang, J.J. B cell antigen receptor signaling enhances IFN-gamma-induced Stat1 target gene expression through calcium mobilization and activation of multiple serine kinase pathways. J Interferon Cytokine Res 25, 113-24 (2005).
Xue, J., Li, G., Laabich, A. & Cooper, N.G. Visual-mediated regulation of retinal CaMKII and its GluR1 substrate is age-dependent. Brain Res Mol Brain Res 93, 95-104 (2001).
Yao, G.L., Kato, H., Khalil, M., Kiryu, S. & Kiyama, H. Selective upregulation of cytokine receptor subchain and their intracellular signalling molecules after peripheral nerve injury. Eur J Neurosci 9, 1047-54 (1997).
Yashiro, K., et al. "Ube3a is Required for Experience-Dependent Maturation of the Neocortex". Nat Neurosci. Jun. 2009;12(6):777-83. Epub May 10, 2009.
Ye, B., et al., (2004) Synthesis and biological evaluation of piperazine-based derivatives as inhibitors of plasminogen activator inhibitor-1 (PAI-1). Bioorg Med Chem Lett.14(3):761-5.
Yoshii, A., et al. "BDNF Induces Transport of PSD-95 to Dendrites Through PI3K-AKT Signaling After NMDA Receptor Activation". Nat Neurosci. Jun. 2007;10(6):702-11. Epub May 21, 2007.
Yu H. et al. "Rapid experience-dependent plasticity of synapse function and structure in ferret visual cortex in vivo". Proc Natl Acad Sci U S A. Dec. 12, 2011.
Yu, H. "The influence of astrocyte activation on hemodynamic signals for functional brain imaging". In: Imaging the Brain with Optical Methods (Roe AW, ed, Springer NY), pp. 45-64, 2010.
Yu, H. et al. "The Coordinated Mapping of Visual Space and Response Features in Visual Cortex". Neuron 47:267-280, 2005.
Yuste, R., and Denk, W. (1995). Dendritic spines as basic functional units of neuronal integration. Nature 375, 682-684.
Zavalova, L., (1996) Genes from the medicinal leech (*Hirudo medicinalis*) coding for unusual enzymes that specifically cleave endo-epsilon (gamma-Glu)-Lys isopeptide bonds and help to dissolve blood clots. Mol Gen Genet. 253(1-2):20-5.
Zheng, W., et al. "The Possible Role of the Akt Signaling Pathway in Schizophrenia". Brain Res. Jul. 4, 2012. [Epub ahead of print].
Zheng, W.H. & Quirion, R. Comparative signaling pathways of insulin-like growth factor-1 and brain-derived neurotrophic factor in hippocampal neurons and the role of the PI3 kinase pathway in cell survival. J Neurochem 89, 844-52 (2004).
Katz, L.C., et al. "Synpatic Activity and the Construction of Cortical Circuits". Science 274, 1133-8 (1996).
Sur, M., et al. "Developments and Plasticity of Cortical Areas and Networks". Nat Rev Neurosci 2, 251-62 (2001).
Desai, N.S., et al. "Critical Periods for Experience-Dependent Synaptic Scaling in Visual Cortex". Nat Neurosci 5, 783-789 (2002).
Wallace, W., et al. "A Morphological Correlate of Synaptic Scaling in Visual Cortex". J Neurosci 24, 6928-6938 (2004).
Philpot, B.D., et al. "Evidence for Altered NMDA Receptor Function as a Basis for Metaplasticity in Visual Cortex". J Neurosci 23, 5586-8 (2003).
Morales, B., et al. "Dark Rearing Alters the Development of GABAergic Transmission in Visual Cortex". J Neurosci 22, 8084-90 (2002).
Iwai, Y., et al. "Rapid Critical Period Induction by Tonic Inhibition in Visual Cortex". J Neurosci 23, 6695-702 (2003).
Turrigiano, G.G., et al. "Homeostatic Plasticity in the Developing Nervous System". Nat Rev Neurosci 5, 97-107 (2004).
Wiesel, T.N. et al. "Single-Cell Responses in Striate Cortex of Kittens Deprived of Vision in One Eye". J Neurophysiol 26, 1003-17 (1963).
Trachtenberg, J.T., et al. "Rapid Extragranular Plasticity in the Absence of Thalamocortical Plasticity in the Developing Primary Visual Cortex". Science 287, 2029-32 (2000).
Trachtenberg, J.T., et al. "Rapid Anatomical Plasticity of Horizontal Connections in the Developing Visual Cortex". J Neurosci 21, 3476-82 (2001).
Oray, S., et al. "Dendritic Spine Dynamics are Regulated by Monocular Deprivation and Extracellular Matrix Degradation". Neuron 44, 1021-30 (2004).
Mataga, N., et al. "Experience-Dependent Pruning of Dendritic Spines in Visual Cortex by Tissue Plasminogen Activator". Neuron 44, 1031-41 (2004).
Shatz, C.J., et al. "Ocular Dominance in Layer IV of the Cat's Visual Cortex and the Effects of Monocular Deprivation". J Physiol 281, 267-83 (1978).
Antonini, A., et al. "Rapid Remodeling of Axonal Arbors in the Visual Cortex". Science 260, 1819-21 (1993).
Crowley, J.C., et al. "Development of Ocular Dominance Columns in the Absence of Retinal Input". Nat Neurosci 2, 1125-30 (1999).
Yang, C.B., et al. "Identification of Munc 13-3 as a Candidate Gene for Critical-Period Neuroplasticity in Visual Cortex". J Neurosci 22, 8614-8 (2002).
Gordon, J.A., et al. "Experience-Dependent Plasticity of Binocular Responses in the Primary Visual Cortex of the Mouse". J Neurosci 16, 3274-86 (1996).
Newton, J.R., et al. "Acceleration of Visually Cued Conditioned Fear through the Auditory Pathway". Nat Neurosci 7, 968-73 (2004).
Majewska, A., et al. "Motility of Dendritic Spines in Visual Cortex in Vivo: Changes During the Critical Period and Effects of Visual Deprivation". Proc Natl Acad Sci USA 100, 16024-9 (2003).
Tusher, V.G., et al. "Significance Analysis of Microarrays Applied to the Ionizing Radiation Response". Proc Natl Acad Sci USA 98, 5116-21 (2001).

(56) References Cited

OTHER PUBLICATIONS

Al-Shahrour, F., et al. "FatiGO: A Web Tool for Finding Significant Associations of GeneOntology Terms with Groups of Genes". *Bioinformatics* 20, 578-80 (2004).

Akerman, C.J., et al. "Visual Experience before Eye-Opening and the Developments of the Retinogeniculate Pathway". *Neuron* 36, 869-79 (2002).

Flames, N. et al. "Developmental Mechanisms Underlying the Generation of Cortical Interneuron Diversity". *Neuron* 46, 377-81 (2005).

das Neves, L., et al. "Disruption of the Murine Nuclear Factor I-A Gene (Nfia) Results in Perinatal Lethality, Hyrocephalus, and Agenesis of the Corpus Callosum". *Proc Natl Acad Sci USA* 96, 11946-51 (1999).

Shu, T., Butz, K.G., Plachez, C., Gronostajski, R.M. & Richards, L.J. Abnormal development of forebrain midline glia and commissural projections in Nfia knock-out mice. J Neurosci 23, 203-12 (2003).

Steele-Perkins, G. et al. The transcription factor gene Nfib is essential for both lung maturation and brain development. Mol Cell Biol 25, 685-98 (2005).

Mootha, V.K. et al. PGC-1alpha-responsive genes involved in oxidative phosphorylation are coordinately downregulated in human diabetes. Nat Genet 34, 267-73 (2003).

Neve, R.L. & Bear, M.F. Visual experience regulates gene expression in the developing striate cortex. Proc Natl Acad Sci U S A 86, 4781-4 (1989).

Pham, T.A., Impey, S., Storm, D.R. & Stryker, M.P. CRE-mediated gene transcription in neocortical neuronal plasticity during the developmental critical period. Neuron 22, 63-72 (1999).

Mataga, N., Nagai, N. & Hensch, T.K. Permissive proteolytic activity for visual cortical plasticity. Proc Natl Acad Sci U S A 99, 7717-21 (2002).

Polleux, F., Whitford, K.L., Dijkhuizen, P.A., Vitalis, T. & Ghosh, A. Control of cortical interneuron migration by neurotrophins and P13-kinase signaling. Development 129, 3147-60 (2002).

Righi, M., Tongiorgi, E. & Cattaneo, A., Brain-derived neurotrophic factor (BDNF) induces dendritic targeting of BDNF and tyrosine kinase B mRNAs in hippocampal neurons through a phosphatidylinositol-3 kinase-dependent pathway. J Neurosci 20, 3165-74 (2000).

Tropea, D., Caleo, M. & Maffei, L., Synergistic effects of brain-derived neurotrophic factor and chondroitinase ABC on retinal fiber sprouting after denervation of the superior colliculus in adult rats. J Neurosci 23, 7034-44 (2003).

Kalatsky, V.A. & Stryker, M.P., New paradigm for optical imaging: temporally encoded maps of intrinsic signal. Neuron 38, 529-45 (2003).

Subramanian, A. et al., Gene set enrichment analysis: a knowledge-based approach for interpreting genome-wide expression profiles. Proc Natl Acad Sci U S A 102, 15545-50 (2005).

Storey, J.D. & Tibshirani, R. Statistical significance for genomewide studies. Proc Natl Acad Sci U S A 100, 9440-5 (2003).

Antonini, A., Fagiolini, M., and Stryker, M. P., Anatomical correlates of functional plasticity in mouse visual cortex. Journal of Neuroscience 19, 4388-4406 (1999).

Russo, V.C., et al., The Insulin-Like Growth Factor System and Its Pleiotropic Functions in Brain. Endocrine Rev., 26(7): 916-943 (2005).

Foster, F., et al., The phosphoinositide (PI) 3-kinase family. J. Cell Sci. 116:3037-3040 (2003).

Kinney, J., et al., A specific Role for NR2A-Containing NMDA Receptors in the Maintenance of Parvalbumin and GAD67 Immunoreactivity in Cultures Interneurons. J. Neurosci., 26(5): 1604-15 (2006).

Baranes, D., Lederfein, D., Huang, Y.Y., Chen, M., Bailey, C. H., and Kandel, E. R., Tissue plasminogen activator contributes to the late phase of LTP and to synaptic growth in the hippocampal mossy fiber pathway. Neuron 21, 813-825 (1998).

Biernaskie, J. and Corbett J., Enriched Rehabilitative Training Promotes Improved Forelimb Motor Function and Enhanced Dendritic Growth after Focal Ischemic Injury, The Journal of Neuroscience, 21(14):5272-5280 (2001).

Bonhoeffer, T., and Yuste, R., Spine Motility: Phenomenology, Mechanisms, and Function. Neuron 35, 1019-1027 (2002).

Callaway, E. M., and Katz, L. C., Emergence and refinement of clustered horizontal connections in cat striate cortex. J Neurosci 10, 1134-1153 (1990).

Callaway, E. M., and Katz, L. C., Effects of binocular deprivation on the development of clustered horizontal connections in cat striate cortex. Proc Natl Acad Sci U S A 88, 745-749 (1991).

Chen, R., et al., "Nervous System Reorganization Following Injury", Neuroscience 111(4): 761-773 (2002).

Cho, IH, et al., Purification and characterization of six fibrinolytic serine-proteases from earthworm *Lumbricus rubellus*. J Biochem Mol Biol. 37(2):199-205 2004.

Dunaevsky, A., Tashiro, A., Majewska, A., Mason, C., and Yuste, R. (1999). Developmental regulation of spine motility in the mammalian central nervous system. Proc Natl Acad Sci U S A 96, 13438-13443 (2003).

Hensch, T. K., Fagiolini, M., Mataga, N., Stryker, M. P., Baekkeskov, S., and Kash, S. F., Local GABA circuit control of experience-dependent plasticity in developing visual cortex. Science 282, 1504-1508 (1998).

Johannson, B., "Brain Plasticity and Stroke Rehabilitation", Stroke, 31:223-230 (2000).

Koester, H. J., and Sakmann, B., Calcium dynamics in single spines during coincident pre- and postsynaptic activity depend on relative timing of back-propagating action potentials and subthreshold excitatory postsynaptic potentials. Proc Natl Acad Sci USA 95, 9596-9601 (1998).

Leamey CA, et al., Disruption of retinogeniculate pattern formation by inhibition of soluble guanylyl cyclase. J Neurosci. 21(11):3871-80 (2001).

Liberatore GT, et al., Vampire bat salivary plasminogen activator (desmoteplase): a unique fibrinolytic enzyme that does not promote neurodegeneration. Stroke. 34(2):537-43 (2003).

Liepert, J., et al., Treatment-Induced Cortical Reorganization After Stroke in Humans, Stroke, 31:1210-1216 (2000).

Mataga, N., Nagai, N., and Hensch, T. K., Permissive proteolytic activity for visual cortical plasticity. Proc Natl Acad Sci U S A 99, 7717-7721 (2002).

Matus, A., Ackermann, M., Pehling, G., Byers, H. R., and Fujiwara, K., High actin concentrations in brain dendritic spines and postsynaptic densities. Proc Natl Acad Sci U S A 79, 7590-7594 (1982).

Nelles, G., et al., "Reorganization of sensory and motor systems in hemiplegic stroke patients. A positron emission study.", Stroke 30:1510-1516 (1999).

Ohtani A, Inhibitory effect of a new butadiene derivative on the production of plasminogen activator inhibitor-1 in cultured bovine endothelial cells. J Biochem (Tokyo). 120(6):1203-8 (1996).

Oray S, Majewska A, Sur M (in press) Effects of synaptic activity on dendritic spine motility of developing cortical layer 5 pyramidal neurons. Cerebral Cortex.

Rijken, D.C. and Collen, D., Purification and characterization of the plasminogen activator secreted by human melanoma cells in culture. J. Biol. Chem., 256, 7035-7042 (1981).

Schlott, et al., Staphylokinase Requires $NH_2$-terminal Proteolysis for Plasminogen Activation. J. Biol. Chem. 272: 6067-6072 (1997).

Siconolfi, L. B., and Seeds, N. W., Induction of the plasminogen activator system accompanies peripheral nerve regeneration after sciatic nerve crush. J Neurosci 21, 4336-4347 (2001).

Sprengers, E.D. and Kluft, C. Plasminogen activator inhibitors. Blood 69, 381-387 (1987).

Sun, et al., Catalytic Nucleic Acids: From Lab to Applications. Pharmacol. Rev., 52:325-47 (2000).

(56) References Cited

OTHER PUBLICATIONS

Teng, YD and Wrathall, JR, Local Blockade of Sodium Channels by Tetrodotoxin Ameliorates Tissue Loss and Long-Term Functional Deficits Resulting from Experimental Spinal Cord Injury. J. Neuroscience, 17(11), pp. 4359-4366 (1997).

Teng, Y.D., et al. (2002) Functional recovery following traumatic spinal cord injury mediated by a unique polymer scaffold seeded with neural stem cells. Proc Natl Acad Sci U S A, 99(5): p. 3024-9.

Teng, Y.D., et al., Minocycline inhibits contusion-triggered mitochondrial cytochrome c release and mitigates functional deficits after spinal cord injury. Proc. Natl. Acad. Sci. 101(9), pp. 3071-3076 (2004).

Westphal M, Hild DC, Bortey E, Delavault P, Olivares R, Warnke PC, Whittle IR, Jaaskelainen J, Ram Z, A phase 3 trial of local chemotherapy with biodegradable carmustine (BCNU) wafers (Gliadel wafers) in patients with primary malignant glioma. Neuro-oncol 5:79-88 (2003).

Xerri, C. et al., Plasticity of primary somatosensory motor cortex paralleling sensorimotor skill recovery from stroke in adult monkeys, J. Neurophysiol., 79:2119-2148 (1998).

Zavalova L, et al., Fibrinogen-fibrin system regulators from bloodsuckers. Biochemistry (Mosc). 67(1):135-42 (2002).

\* cited by examiner

IDENTIFYING AND MODULATING MOLECULAR PATHWAYS THAT MEDIATE NERVOUS SYSTEM PLASTICITY

RELATED APPLICATIONS

The present application claims priority under 35 U.S.C. §119(e) to U.S. provisional patent application U.S. Ser. No. 60/792,275, filed Apr. 14, 2006, which is incorporated herein by reference.

GOVERNMENT SUPPORT

This invention was made with Government Support under Grant No. EY014134 awarded by the NIH. The Government has certain rights in the invention.

BACKGROUND OF THE INVENTION

Diseases and accidents leading to nervous system damage or degeneration are among the leading causes of mortality and morbidity in many countries. For example, approximately 700,000 people suffer a first or recurrent stroke annually in the United States, resulting in over 150,000 deaths. Although stroke represents the most common cause of damage to the central nervous system (CNS), a number of other conditions are also significant causes of functional deficits due to loss of brain tissue, either as a direct consequence of injury, or secondary to events such as swelling. Among these are primary brain tumors, brain metastases, and surgery for these or other conditions.

Strokes are a result of a sudden disruption of blood flow to a part of the brain and occur when a blood vessel that normally supplies brain tissue either bursts or becomes transiently or permanently blocked, such as by a blood clot (e.g., a thromboembolus) or other embolus or obstruction. The resulting disruption in normal blood flow deprives the affected tissue of needed oxygen and nutrients and can also impair removal of waste products, resulting in damage to, or death of, nervous system cells. Currently the only therapy for ischemic stroke approved by the U.S. Food and Drug Administration (FDA) is infusion of the thrombolytic agent tissue type plasminogen activator (tPA) within a short time window following the causative event. Such thrombolytic therapy was shown to be both safe and beneficial if delivered within 3 hours of the onset of symptoms (NINDS, Tissue plasminogen activator for acute ischemic stroke. The national institute of neurological disorders and stroke RT-PA stroke study group. *N. Engl. J. Med.* 333: 1581-1587, 1995).

While stroke is the third leading cause of death in industrialized countries, in most cases stroke is not fatal. However, stroke is a major cause of morbidity and a leading cause of serious, long-term disability. About 4.8 million stroke survivors are alive today in the United States, with a much larger total number worldwide. Many of these individuals suffer from functional limitations affecting the senses, motor activity, speech and/or the ability to understand speech, behavior, thought patterns, memory, emotions, or other aspects of cognition. Although functional deficits following stroke may be permanent, in many cases full or partial recovery is possible. The mainstays of treatment are supportive care and rehabilitation therapy, which frequently continues for months or years. Unfortunately, there are no pharmacological agents that have demonstrated efficacy in improving the long-term outcome of stroke.

Approximately 10,000-12,000 individuals suffer spinal cord injuries (SCI) each year in the United States, bringing the projected prevalence rate in the United States to nearly 280,000 by the year 2014 (DeVivo, M. J., 2002) Improvements in supportive care have greatly increased the survival rate following such injuries, but therapeutic options remain limited, and efforts focus on rehabilitation. Tumors affecting the spinal cord or meninges (either primary tumors or metastases) are also a significant source of morbidity.

Disorders of the nervous system also have a massive impact on society. Disorders of brain development, such as autism, now afflict about 1 in 166 children. The total number of individuals in the U.S. afflicted with autism, learning disabilities, and similar disorders is estimated to exceed 4 million. Neuropsychiatric disorders such as schizophrenia and bipolar disorders extract a huge cost in lifetime care for afflicted individuals as well as emotional toll on caregivers and families. Neurodevelopmental disorders such as autism are usually treated with behavioral therapies alone, and these strategies have limited success. Similarly, neuropsychiatric disorders such as schizophrenia and bipolar disorder have very limited therapeutic possibilities.

Thus there is a need in the art for improved treatments, particularly pharmacological treatments, that would enhance recovery following damage to the CNS and/or help improve CNS and cognitive function in neuropsychiatric and neurodevelopmental disorders. Common to a large range of CNS conditions is the concept that they centrally involve the function of synapses and their ability to change (i.e., plasticity). Thus, there is a need for new approaches to the identification of genes, molecules, cell types, and biological pathways that play a role in key nervous system properties such as plasticity and that can be modulated to provide a therapeutic benefit.

SUMMARY OF THE INVENTION

The invention provides a method of identifying a gene involved in plasticity comprising steps of: subjecting an individual to a condition that modifies nervous system plasticity; measuring level or activity of each of a plurality of genes in at least a portion of the individual's nervous system; and identifying one or more genes whose expression or activity is differentially regulated in the portion of the individual's nervous system relative to its expression or activity under alternative conditions. In some embodiments, the condition comprises depriving at least a portion of the individual's nervous system of normal inputs. The method may comprise identifying a biological pathway or process enriched in genes that are differentially regulated in at least a portion of the nervous system of an individual subjected to a plasticity-modifying condition.

The invention provides genes that are differentially regulated under conditions that modify plasticity. The invention provides biological pathways that are enriched in such genes. The invention identifies a specific cell type, parvalbumin containing interneurons, as being downregulated under conditions that prolong plasticity. Based at least in part on the identification of these genes, pathways, and cell type, the invention provides combinations of plasticity-modifying agents of particular use. For example, in one embodiment an activator of the insulin-like growth factor 1 (IGF1) pathway (e.g., IGF1 or an active peptide fragment thereof; or a modulator of the JAK/STAT pathway, e.g., IFNγ or an HMG-CoA reductase inhibitor such as a statin) are administered to a subject either individually or in a single composition.

The present invention provides a method for modifying plasticity in the nervous system of a subject comprising the step of: administering a plasticity-modifying agent to a subject in need thereof, wherein the agent is administered either alone or in combination with one or more additional agents in an amount effective to modify nervous system plasticity, wherein the plasticity-modifying agent modulates a gene or pathway that is differentially regulated in at least a portion of the nervous system of an individual subjected to a plasticity-modifying condition. The agent may be administered once, multiple times, and/or continuously. The time may be selected in conjunction with the amount to be effective to modify nervous system plasticity. Exemplary plasticity-modifying condition comprise dark rearing or monocular deprivation.

The invention includes a method for promoting recovery and/or reorganization in the nervous system of a subject in need of enhancement of recovery and/or reorganization of the nervous system comprising administering a plasticity-modifying agent to the subject, wherein the plasticity-enhancing agent modulates a gene or pathway that is differentially regulated in the nervous system of an individual subjected to a plasticity-modifying condition, e.g., dark-rearing (DR) or monocular deprivation (MD). The agent is administered in an amount effective to promote recovery or reorganization in the nervous system. The agent may be administered once, multiple times, and/or continuously. The time may be selected in conjunction with the amount to be effective to promote nervous system recovery or reorganization. The subject may be in need of recovery or reorganization of the nervous system as a result of ischemic, hemorrhagic, neoplastic, degenerative, traumatic, and/or neurodevelopmental damage to the nervous system. The subject may be in need of reorganization of the nervous system as a result of a neurodevelopmental or neuropsychiatric disorder. The method can include a step of identifying or providing, e.g., diagnosing a subject as having suffered such damage or having a neurodevelopmental or neuropsychiatric disorder. The methods can include a step of identifying or diagnosing the subject as having a reasonable likelihood (e.g., at least a 5% chance, at least a 10%, or at least a 50% chance).

The methods may also include administering a proteolysis-enhancing agent such as tissue plasminogen activator (tPA), plasmin, or a PAI inhibitor to the nervous system of the subject. A plasticity-modifying agent of the present invention is, in general, distinct from the proteolysis-enhancing agents described herein. The plasticity-modifying agent and the proteolysis-enhancing agent may be administered as part of a single composition or individually. The present invention provides a composition comprising a plasticity-modifying agent and a proteolysis-enhancing agent. The composition(s) can be delivered using a variety of techniques including injection, via infusion pump, from an implantable microchip, or using a polymeric delivery vehicle. The composition(s) can be administered, for example, to one or more subdivisions or areas of the brain, the spinal cord, or to one or more nerves or nerve tracts innervating diverse regions of the body.

In certain embodiments the composition is administered by implanting into the subject a drug delivery device that releases the plasticity-modifying agent over a period of time at or in the vicinity of a desired location. The desired location can be, for example, an area of ischemic, hemorrhagic, neoplastic, degenerative, traumatic, and/or neurodevelopmental damage in the central or peripheral nervous system, or location in a brain hemisphere opposite to an area of damage. In some embodiments the drug delivery device comprises a pump. In some embodiments the drug delivery device comprises a biocompatible polymer, e.g., a biodegradable polymer. In some embodiments the polymeric matrix of the drug delivery device comprises a hydrogel. In some embodiments of the invention the composition comprises a plurality of polymeric microparticles or nanoparticles having the plasticity-modifying agent associated therewith (e.g., encapsulated therein, adsorbed thereon, entangled in a polymer network, etc.).

The invention also includes a drug delivery device for implantation into the body of a subject to modify plasticity. In certain embodiments of the invention the device is implanted to promote nervous system reorganization and/or recovery following ischemic, hemorrhagic, neoplastic, traumatic, degenerative, and/or neurodevelopmental damage.

An inventive device may include a proteolysis-enhancing agent, e.g., a proteolytic agent such as a protease. Alternatively or additionally, a proteolysis-enhancing agent can be administered separately. In certain embodiments the proteolysis-enhancing agent is plasmin, a plasminogen activator, and/or an inhibitor of an endogenous plasminogen activator inhibitor. For example, in certain embodiments, the proteolysis-enhancing agent is tissue plasminogen activator (tPA), e.g., human tPA. In certain embodiments of the invention, the proteolysis-enhancing agent is plasmin. In certain embodiments, the proteolysis-enhancing agent promotes degradation of a component of the extracellular matrix (ECM). In certain embodiments, the proteolytic agent directly or indirectly degrades fibrin.

Optionally, the plasticity-modifying agent and/or the proteolysis-enhancing agent is covalently attached to a polymer by an optionally cleavable linkage. In some embodiments, one or both of the plasticity-modifying agent and the proteolysis-enhancing agent is delivered in a solution that forms a gel following contact with physiological fluids. The plasticity-modifying agent and, optionally, a proteolysis-enhancing agent may, for example, be delivered in an amount effective to promote structural reorganization of synaptic connections, increase formation of new synaptic connections, increase dendritic spine motility, promote growth of axons and synaptic connections, inhibit at least in part functional and/or structural deterioration or degradation, stabilize synapses, or any combination of the foregoing.

In certain embodiments the composition comprises one or more neural growth enhancing agents, neurotransmitters or analogs thereof, neurally active growth factors, neural signaling molecules, neurally active small molecules, and neurally active metals. Alternatively or additionally, one or more of these agents can be administered separately, for example, by focal administration to the nervous system or by an alternate route.

The invention further provides a method of treating a subject in need of enhancement of recovery or reorganization in the nervous system comprising focally administering a composition comprising a plasticity-modifying agent and a proteolysis-enhancing agent to the central or peripheral nervous system of the subject. The subject will typically have suffered nervous system damage as a result of ischemic, hemorrhagic, neoplastic, degenerative, traumatic, and/or neurodevelopmental damage. The invention provides methods of treating a subject in need of enhancement of recovery and/or reorganization in the nervous system comprising administering a plasticity-modifying agent, a proteolysis-enhancing agent, and a neural growth enhancing agent to the subject. One, more than one, or all of the agents can be administered focally to the central or peripheral nervous system. Agents can be administered separately or in a single composition. Any of the methods for administration contemplated herein can be used.

In any of the inventive methods, the subject may be engaged in a program of rehabilitation designed to promote functional recovery following ischemic, hemorrhagic, neoplastic, traumatic, and/or neurodevelopmental damage to the nervous system, wherein the subject is so engaged during at least part of the time interval during which the agent is administered or during which the agent remains active in the nervous system of the subject.

In any of the methods described herein, the subject may be engaged in a program of behavioral or cognitive therapy to improve function of the nervous system following from a neurodevelopmental disorder, wherein the subject is so engaged during at least part of the time interval during which the agent is administered or during which the agent remains active in the nervous system of the subject.

The present invention provides drug delivery devices comprising: a biocompatible polymer and a plasticity-modifying agent, wherein the plasticity-modifying agent agent is released from the polymer in an amount effective to promote structural or functional recovery or reorganization in the nervous system of the subject. The device may comprise a proteolysis-enhancing agent.

The present invention provides compositions comprising a plasticity-modifying agent and a neural growth enhancing agent, which is optionally selected from among neurotransmitters or analogs thereof, neurally active growth factors, neural signaling molecules, and neurally active small molecules, and neurally active metals. The invention comprises drug delivery devices, e.g., polymer-based drug delivery devices, comprising the composition.

This application refers to various patents and publications. The contents of all of these are incorporated by reference. In addition, the following publications are incorporated herein by reference: Ausubel, F., (ed.). *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Kandel, E., Schwartz, J. H., Jessell, T. M., (eds.), *Principles of Neural Science*, 4$^{th}$ ed., McGraw Hill, 2000; Cowan, W. M., Südhof, T. C., and Stevens, C. F., (eds.), *Synapses*, The Johns Hopkins University Press, Baltimore and London, 2001; and Hardman, J., Limbird. E., Gilman, A. (Eds.), Victor, M. and Ropper, A. H., *Adams and Victor's Principles of Neurology*, 7$^{th}$ ed., McGraw Hill, 2000; Grossman, R. I. and Yousem, D. M., *Neuroradiology: The Requisites*, 2$^{nd}$ ed., C. V. Mosby, 2003; Gillen, G. and Burkhardt, A. (eds.), Stroke Rehabilitation. A Function-Based Approach, 2$^{nd}$ ed., C. V. Mosby, 2004; Somers, M. F., *Spinal Cord Injury: Functional Rehabilitation*, 2$^{nd}$ ed., Prentice Hall, 2001; *Goodman and Gilman's The Pharmacological Basis of Therapeutics*, 10th Ed., McGraw Hill, 2001 (referred to herein as *Goodman and Gilman*). In the event of a conflict or inconsistency between any of the incorporated references and the instant specification or the understanding of one or ordinary skill in the art, the specification shall control, it being understood that the determination of whether a conflict or inconsistency exists is within the discretion of the inventors and can be made at any time.

Where ranges of numerical values are stated herein, the endpoints are included within the range unless otherwise stated or otherwise evident from the context. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included in or excluded from the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

This application refers to various genes and proteins using names that are well known in the art. At times one or more identifiers and/or accession numbers for these genes and proteins are provided. Such names, identifiers, and/or accession numbers are utilized in various databases available to one of skill in the art such as Genbank and Pubmed. For example, one of skill in the art can search the Entrez Gene database provided by the National Center for Biotechnology Information (NCBI), available at the web site having URL www.ncbi.nlm.nih.gov/entrez/query.fcgi?CMD=search&DB=gene and can thereby locate the Gene ID for any particular gene or protein of interest. The Gene ID entry provides biological information, alternate names, chromosomal location, etc., as well as links to database entries for the corresponding nucleotide and protein sequences and references in the scientific literature. It will be appreciated that the names and/or sequences of genes mentioned herein may differ in different species. The invention encompasses the genes regardless of species. When the methods for modifying plasticity, nervous system structure or function, nervous system recovery or reorganization, etc., are applied to a subject it may be preferable to employ agents that modulate the expression and/or activity of genes and/or pathways as they exist in the species to which the subject belongs, although in many cases such agents will be effective in multiple species. In certain embodiments of the invention the gene is a human gene. One of skill in the art will be able to identify the human homologs of mouse genes mentioned herein in other species such as humans.

Figure 2:
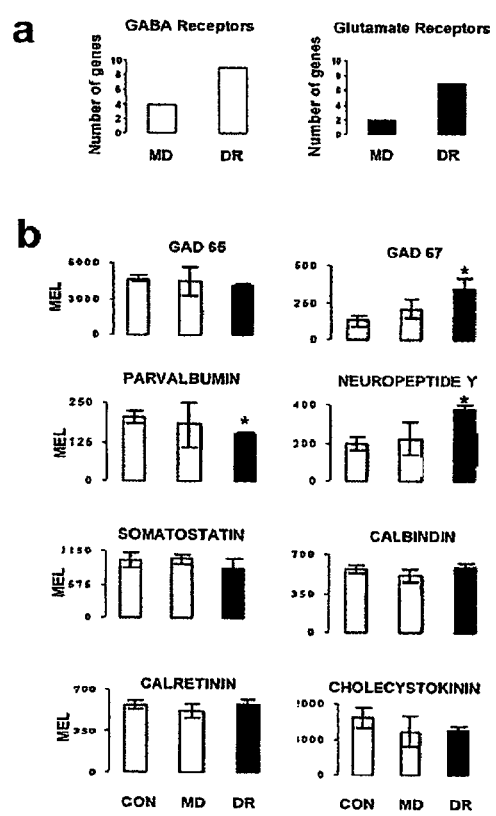

FIG. 2: Regulation of genes involved in excitatory and inhibitory transmission in MD and DR animals. (A) Numbers of inhibitory/excitatory receptor genes that are significantly upregulated in MD or DR versus control. (B) Representation of the Microarray Expression Levels (MEL) in control (con), Monocularly Deprived (MD) and Dark Reared (DR) animals of glutamic acid decarboxylase genes (GAD65 and GAD67), the synthetic enzymes for GABA, and different classes of inhibitory neurons. Only the probes for parvalbumin are significantly downregulated in DR, while the other markers are either upregulated or unchanged (star indicates two-tailed t test, $P<0.05$).

Figure 3:
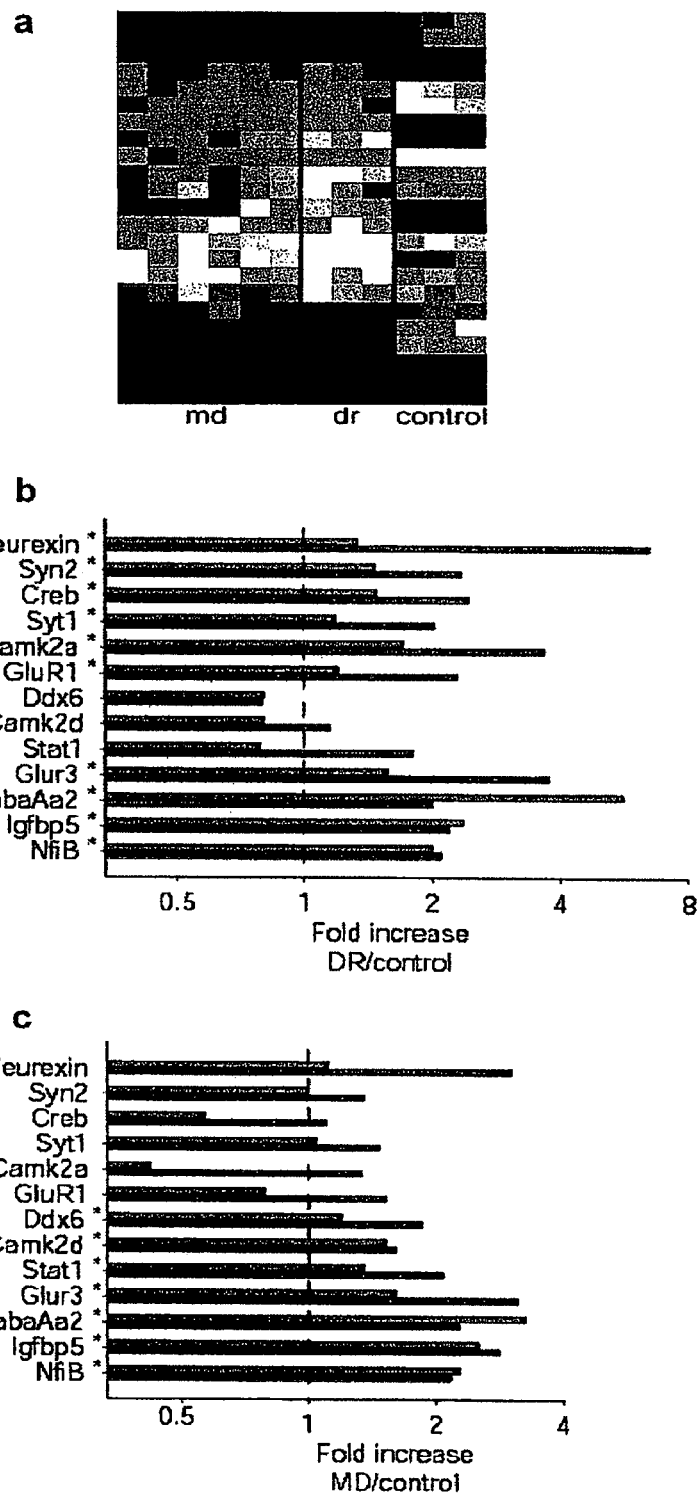

FIG. 3: Confirmation of selected molecules with RT-PCR. (A) Heat map of the genes confirmed with semi-quantitative PCR. The level of expression is represented in logarithmic scale; red corresponds to maximal expression and blue to minimal expression. The genes are ranked according to their expression level after MD. (B, C) Representation of the fold increase of selected molecules in DR (B) and MD (C) versus control, showing the ratio between DR or MD versus control for Microarray Expression Levels (red) and PCR values (green). A star indicates that the microarray expression of the corresponding gene is significantly upregulated (two-tailed t test $P<0.05$) in DR vs. control or MD versus control.

Figure 4:
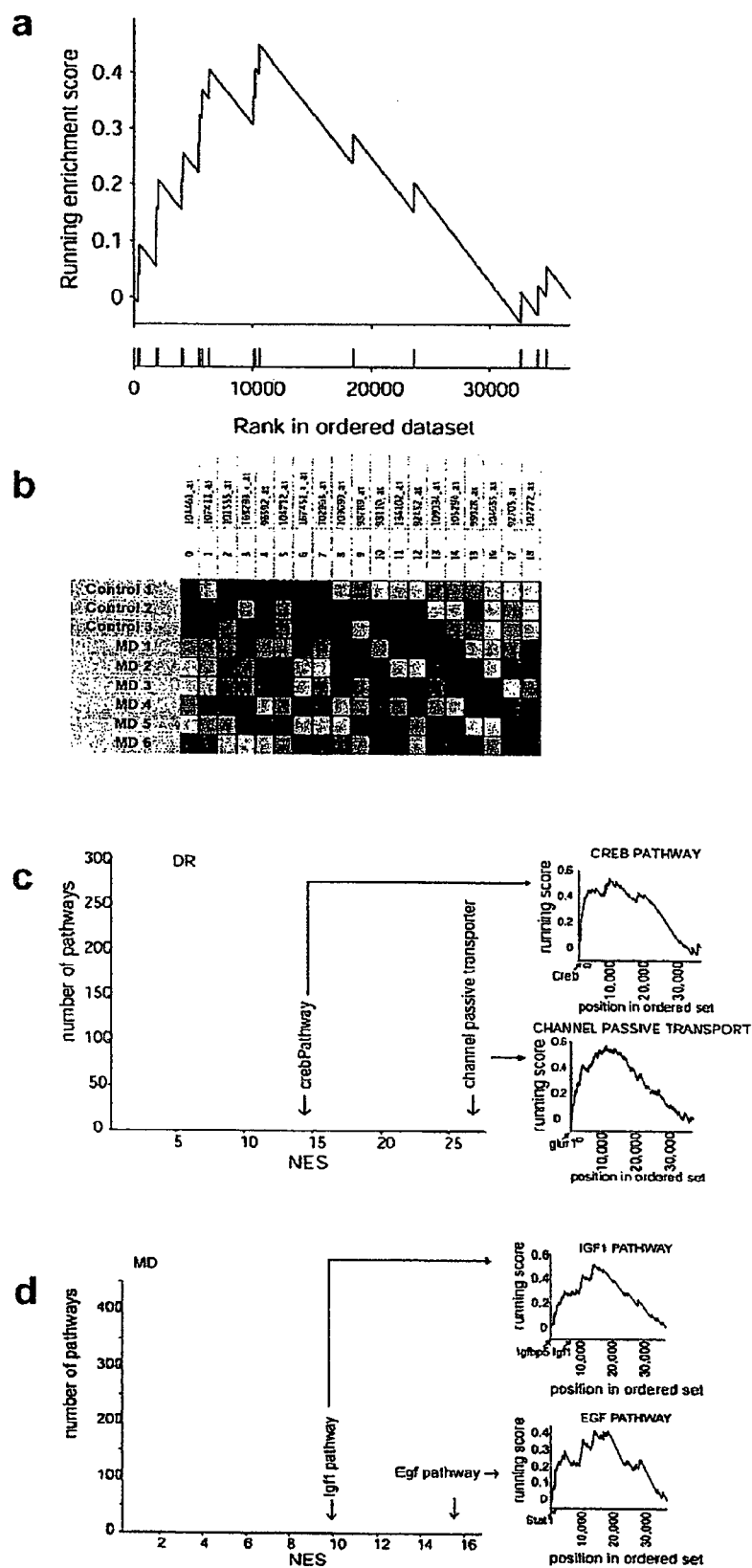

FIG. 4: Gene Set Enrichment Analysis of gene expression after DR and MD. (A) Example analysis of enrichment of the ARF pathway in the MD versus control data set. The hypothesis tested is that the expression of the ARF gene set (n=19 genes) is enriched in the MD versus control data set. The genes in the dataset are ranked according to a correlation statistic (signal-to-noise ratio); genes up-regulated after MD vs. control appear first while genes up-regulated in control (that is, downregulated in MD vs. control) appear late. The straight lines represent genes in the ranked list that are in the ARF pathway (bottom). The running enrichment score is plotted in the upper graph (top). The peak enrichment score for the ARF pathway in the MD versus control data set is 0.48, leading to a normalized enrichment score (NES) of 6.8. (B) Heat map of the expression levels of all the probes of the ARF pathway gene set in the MD and control samples. Highest levels of expression correspond to brilliant red, while lowest levels of expression correspond to dark blue. (C) Distribution of normalized enrichment score (NES) values for the DR versus control data set. The arrows highlight two pathways that are particularly enriched in DR and are discussed in the text: the CREB pathway and the Channel Passive Transporter pathway. The insets show the running enrichment scores for these two pathways; the red arrows show the positions of Creb and GluR1 probes respectively. (D) Distribution of NES values in the GSEA analysis for the MD versus control data set. The arrows indicate two pathways discussed in the text which are particularly enriched in MD: the EGF pathway and the IGF1 pathway. For each of these pathways, the insets show the running enrichment score. The red arrows in the insets point to the positions of Stat1 and IGF1-IGFBP5 probes respectively.

Figure 5:
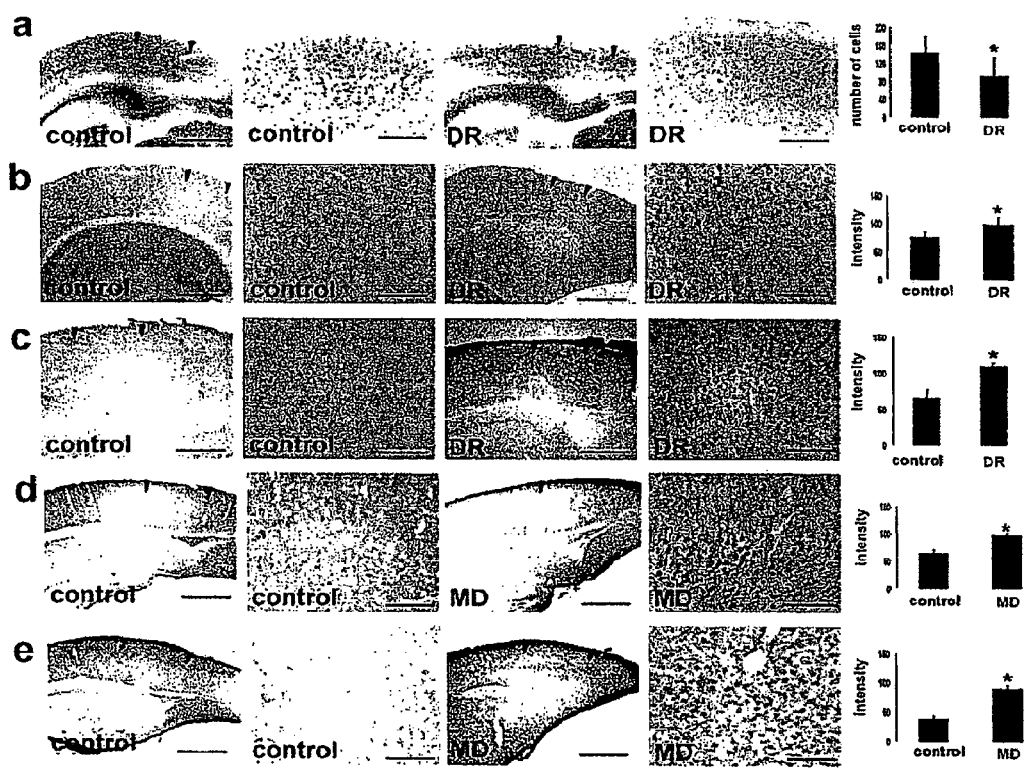

FIG. 5. Immunohistochemistry for molecules that show increased expression following DR and MD. Immunohistochemistry for selected molecules was performed on coronal slices containing V1 from P27 control, Dark Reared (DR) and Monocularly Deprived (MD) mice. In DR mice, the expression of three proteins: (A) Parvalbumin, (B) GluR1 and (C) Phospho-Creb was examined. The parvalbumin gene is down-regulated in DR versus control and the immunohistochemistry shows a decrease in the number of parvalbumin-positive neurons in DR animals. The histogram on the right shows a significant decrease ($P<0.01$) in the number of parvalbuminergic neurons versus control. GluR1 and P-Creb proteins were over-expressed in visual cortex of DR animals versus control. In MD mice, the expression of (D) activated Stat1 and (E) IGFBP5 was examined. Both proteins are selectively up-regulated in V1 after 15 days of MD relative to control. Bars in the right panels (B-E) show the intensity of the staining in sections of DR or MD and control animals; for all the molecules examined the intensity of staining was significantly higher in the deprived conditions that in controls ($P<0.05$). For each molecule, low magnification pictures (scale bar=765 µm) and high magnification pictures (scale bar=100 µm) are shown. Arrows in the low magnification pictures demarcate V1.

Figure 6:
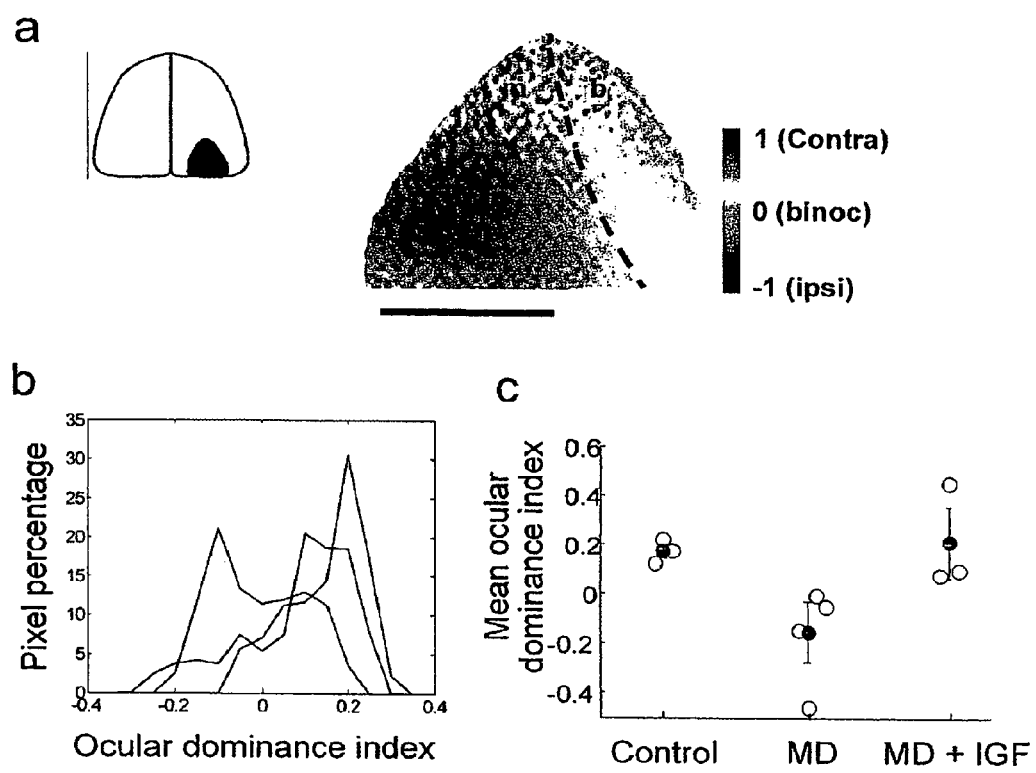

FIG. 6: Application of IGF1 prevents the ocular dominance shift after MD in mouse V1. (A) Left: Mouse brain showing the location of V1 (black region). Right: Ocular dominance index map in mouse V1. The dotted line separates the binocular zone (b) from the monocular zone (m). Scale bar, 1 mm. (B) Histograms of ocular dominance index in the binocular zone of three representative mice. Red line, P27 control mouse; black line, P27 mouse after 7 days of MD; blue line, P30 mouse after 7 days of MD plus IGF1 application for the same period. The data from each animal typically includes a region within binocular cortex containing over 2000 pixels. (C). Mean ocular dominance indices of the 3 groups of mice. Open circles, mean ocular dominance index of the binocular zone pixels from each animal; filled circles, average value of each group.

Figure 7:
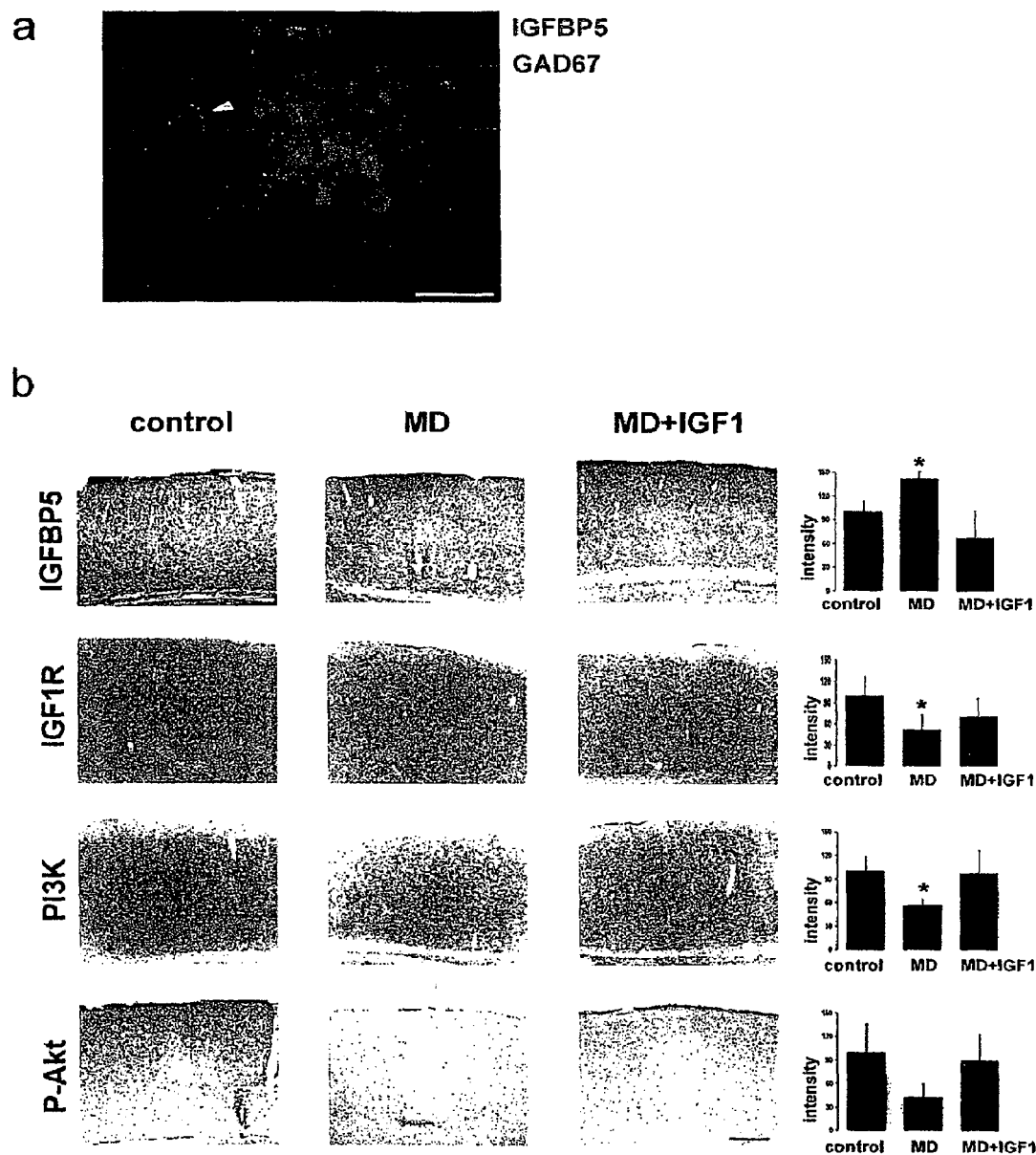

FIG. 7: Immunohistochemistry for selected markers of the IGF1 pathway. (A) Double staining for IGFBP5 (green) and GAD67 (red) in visual cortex of a P28 mouse. Yellow arrow shows an overlap between the two colors suggesting that IGFBP5 is present in GABAergic neurons; however the presence of cells immunopositive for IGFBP5 but not for GAD67 (green arrow) and vice versa (red arrow) shows that IGFBP5 is present in other cell classes as well. Scale bar=17 µm. (B) Immunostaining for selected molecules in three different conditions: P28 control (animal reared in normal light conditions), P28 MD (animals monocularly deprived for 4 days), and P28 MD+IGF1 (animals deprived for 4 days and simultaneously injected IP daily with IGF1 solution). In all the MD panels the cortex shown is contralateral to the deprived eye. Bars at right show the staining intensity of each molecule in the different conditions. Scale bar=70 µm.

BRIEF DESCRIPTION OF THE TABLE APPENDIX

The Appendix, which is a part of the instant specification, consists of the following Tables:

Table 4 lists genes whose expression is downregulated in visual cortex under conditions of DR.

Table 5 lists genes whose expression is upregulated in visual cortex under conditions of DR.

Table 6 lists genes whose expression is downregulated in visual cortex under conditions of long term MD.

Table 7 lists genes whose expression is upregulated in visual cortex under conditions of long term MD.

Table 8 lists genes whose expression is downregulated in visual cortex under conditions of short term MD Table 9 lists genes whose expression is upregulated in visual cortex under conditions of short term MD.

Table 10 lists genes that are downregulated in visual cortex under conditions of short term MD in subjects treated with an activator of the IGF1 pathway.

Table 11 lists genes that are upregulated in visual cortex under conditions of short term MD in subjects treated with an activator of the IGF1 pathway.

DEFINITIONS

Approximately: As used herein, the term "approximately" in reference to a number is generally taken to include numbers that fall within a range of 10% in either direction of the number (greater than or less than) unless otherwise stated or otherwise evident from the context (except where such number would exceed 100% of a possible value).

Agonist: As used herein, the term "agonist" generally refers to a substance that can directly interact with (e.g., bind to) a receptor and initiate a physiological or a pharmacological response characteristic of the activity of that receptor, e.g., the activity that is normally induced by interaction of an endogenous positively-acting ligand with the receptor. Substances generally recognized in the literature as agonists of a particular receptor are of use in the methods described herein. The term "agonist" also refers to partial agonists, i.e., compounds that are capable of partially activating a receptor, e.g., activating it to a lesser extent than its endogenous ligand. The term also encompasses substances that indirectly stimulate a receptor, e.g., by inhibiting reuptake or breakdown/metabolism of an endogenous direct agonist and/or by stimulating the production or release of an endogenous direct agonist.

Antagonist: As used herein, the term "antagonist" generally refers to a substance that opposes the receptor-associated responses normally induced by another bioactive agent such as an endogenous positively-acting ligand. Typically, an antagonist binds to a receptor and prevents binding of an endogenous ligand that would normally activate the receptor, or prevents binding of an exogenous agonist to the receptor. The antagonist may or may not induce an effect itself. The activity of a receptor is generally taken to be the activity associated with binding of an endogenous positively-acting ligand. Substances generally recognized in the literature as antagonists of a particular receptor are of use in the methods described herein. The term also encompasses substances that indirectly inhibit a receptor, e.g., by inhibiting reuptake or by stimulating breakdown/metabolism of an endogenous direct agonist and/or by stimulating the production or release of an endogenous direct antagonist.

Biocompatible: A material is considered "biocompatible" if it is substantially non-toxic to the recipient, in the quantities and at the location used, and also does not elicit or cause a significant deleterious or untoward effect on the recipient's body, e.g., a significant immunological or inflammatory reaction, unacceptable scar tissue formation, etc.

Biodegradable: As used herein, the term "biodegradable," refers to a material that is capable of being broken down physically and/or chemically within the body of a subject, e.g., by hydrolysis under physiological conditions, by natural biological processes such as the action of enzymes present within the body, etc., to form smaller chemical species which can be metabolized and/or excreted.

Biological information resource: As used herein, the term "biological information resource" refers to a compilation of reliable information about biochemical species (e.g., genes or their expression products, substrates, cofactors, physiologically important ions or small molecules), biological processes, and optionally, biological pathways, from which it is possible to conveniently determine information such as (i) whether a biochemical species is a component of a particular biological process; (ii) which biochemical species are components of a particular biological process; (iii) which biological processes include a particular biochemical species as a component; (iv) whether a particular biological process includes a particular biochemical species as a component, etc. A biological information resource can also include any type of additional biological information. For example, information such as identifiers of compounds known to interact with a biochemical species or known to influence a biological pathway can be included. Names of diseases or clinical conditions that are related to a biological process or biochemical species, e.g., in which the biological process or biochemical species plays a causative role, or in which a defect in the biological process or biochemical species plays a causative role, can be included. By "reliable information" is meant information that is generally recognized in the art as being substantially accurate. Typically such information will have been published in the scientific literature and described therein in sufficient detail to be capable of being independently verified and will have been replicated and/or acknowledged as being accurate in one or more additional scientific publications. A biological information resource will typically comprise a database and will provide one or more software tools that allow a user to readily obtain access to the information and to search the information using one or more query terms, e.g., an identifier for a biochemical species, biological process, etc. An "identifier" refers to any term or combination of terms that is used to refer to a biochemical species, biological process, etc. The identifier can be, for example, the name of a gene or the name of a biological process.

Biological pathway: As used herein, the term "biological pathway" refers to a sequence of reactions (e.g., physical interactions between molecules, enzyme reactions) that takes place in a living organism, typically resulting in a biological effect. A pathway typically involves a cascade of events in which molecules involved in the pathway (referred to as "components" of the pathway) signal to or act upon each other, often in a characteristic and ordered manner. Many of the components of the pathway are RNA or polypeptide expression products of genes (also referred to as "gene products"). Such genes may also be referred to as components of the pathway. Biological pathways of interest herein include the IGF1 pathway, the JAK/STAT pathway, the PI3 kinase pathway, and subpathways thereof.

Biological process: As used herein, the term "biological process" refers to a series of events accomplished by one or more biochemical species or ordered assemblies of biochemical species. The biochemical species or assemblies thereof are referred to as "components" of the biological process. The components are said to be "involved in" the biological process. For example, a gene product that is a component of a biological process, i.e., plays a role in carrying out that biological process, is said to be involved in that biological process. Genes whose expression product(s) are components of a biological process may also be referred to as components of the pathway. The series of events making up a biological process is typically directed towards achieving a biological goal of significance to the biological system. Examples of biological processes include, without limitation, cell communication, metabolism, morphogenesis, secretion, etc. It will be appreciated that a biological process may comprise a plurality of biological processes (subprocesses). A biological process may comprise or be performed by one or more biological pathways. The "central nervous system" (CNS)

includes the brain, spinal cord, optic, olfactory, and auditory systems. The CNS comprises both neurons and glial cells (neuroglia), which are support cells that aid the function of neurons. Oligodendrocytes, astrocytes, and microglia are glial cells within the CNS. Oligodendrocytes myelinate axons in the CNS, while astrocytes contribute to the blood-brain barrier, which separates the CNS from blood proteins and cells, and perform a number of supportive functions for neurons. Microglial cells serve immune system functions.

Concurrent administration: The term "concurrent administration," as used herein with respect to two or more agents, e.g., therapeutic agents, is administration performed using doses and time intervals such that the administered agents are present together within the body, or at a site of action in the body such as in the CNS in amounts sufficient to have a biological effect over a time interval of minutes, hours, days, weeks, etc. The agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart).

Critical period: As used herein, the term "critical period" refers to a time period during the development of an organism in which the organism's nervous system is particularly able to acquire a specific functional ability and/or structural configuration, typically at least in part in response to external environmental stimuli. Absence of the appropriate stimuli during the critical period typically results in failure to develop the functional ability and/or structural configuration that would develop had these stimuli been present. The timing and duration of the critical period may depend upon the environmental stimuli received. For example, lack of certain environmental stimuli prolongs the critical period.

Deprived condition: As used herein, the term "deprived condition" refers to an environment that fail to provide adequate environmental stimuli needed to allow normal development of one or more functional or structural features of the nervous system. An individual subjected to a deprivation condition typically receives fewer and/or less intense or varied stimuli of one or more types than an individual subjected to "normal conditions." In the case of an animal raised in a laboratory, "normal conditions" are standard laboratory conditions typically used for the maintenance of such animals.

Effective amount: As used herein, an "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. A desired biological response may be, for example, (i) functional or structural reorganization of synaptic connections, dendrites, or axon projections; (ii) maintenance of synaptic connections, dendrites, or axon projections under conditions in which they would otherwise deteriorate; (iii) regeneration of a nerve or an axonal projection system or its maintenance under conditions in which it would otherwise deteriorate; (iv) an improvement in performance of a task requiring motor or sensory function; (v) an improvement in performance of a task requiring cognitive function, e.g., improved performance on a test that measures learning and/or memory; (vi) a slowing in the rate of decline in motor, sensory, and/or cognitive function.

Enriched condition: As used herein, the term "enriched condition" refers to an environment that provides receives more stimuli and/or more intense or varied stimuli of one or more types than an individual subjected to "normal conditions."

Expression product: As used herein, the term "expression product" or "gene product" refers to an RNA transcribed from a gene or a polypeptide translated from an RNA transcribed from a gene. RNAs or polypeptides that are modified following their transcription or translation are considered expression products of the gene that encodes them. Modifications include, e.g., splicing, cleavage, addition of phosphate or fatty acid groups, etc.

Focal delivery: As used herein, the term "focal delivery" (or "focal administration" in reference to delivery of a pharmacological agent), refers to delivery that does not rely upon transport of the agent to its intended target tissue via the vascular system, e.g., the agent is not administered directly into a blood vessel. The agent is delivered directly to its intended target tissue or in the vicinity thereof, e.g. by injection through a needle, catheter, or cannula, or by implantation of a delivery vehicle or device containing the agent. If the agent is delivered to the vicinity of its target tissue rather than into the target tissue itself, the agent may reach its target tissue by diffusion. For purposes of the present invention, any method that achieves delivery of an agent to the CNS or portion thereof without requiring transport via the vascular system from a site outside the skull or meninges (the membranes that cover the brain and the spinal cord), is considered to achieve focal delivery of the agent. Specifically included are delivery by use of an implanted or external pump, and/or delivery directly into one or more ventricles of the CNS. It will be understood that once having been focally delivered a portion of the agent (typically only a minor fraction thereof) may in part enter the vascular system and be transported to another location.

Function: As used herein, the term "function," with reference to the nervous system or a component thereof, is used broadly herein to refer to any function, role, task, or activity performed by the nervous system or a component thereof. The term includes, without limitation, the ability to process and recall information, regulate behavior, stimulate release of endogenous chemicals, control motor functions, receive and process sensory input, maintain consciousness, etc.

Functional recovery: As used herein, the term "functional recovery" refers to the process in which a nervous system or component thereof that has at least in part lost the ability to perform a function that it previously performed, regains at least in part the ability to perform the function. Functional recovery may take place in at least two different ways: (i) the recovery in function may involve partial or complete recovery of the portion of the nervous system that previously performed the function; (ii) the recovery in function may involve a portion of the nervous system performing a function that it did not previously perform. Of course in some instances both processes may take place. Functional recovery can also refer to preservation of the ability of the nervous system or a portion thereof to perform a function that it previously performed, after the nervous system or component thereof has been physically altered, disrupted, or otherwise subjected to a physical or chemical insult or neurodegenerative disease, when such physical alteration, disruption, physical or chemical insult or neurodegenerative disease would otherwise be expected to lead to deterioration or loss of the ability of the nervous system or portion thereof to perform the function.

Functional reorganization: The term "functional reorganization," as used in reference to the nervous system or a portion thereof, refers to the process in which a portion of the nervous system wholly or partially assumes, i.e., takes on, a function (e.g., a sensory, motor, or cognitive function) that was not previously performed by that portion of the nervous system. The function or task may, but need not have been, previously performed by a different portion of the nervous system. Functional reorganization may, but need not, entail one or more aspects of structural reorganization. Functional reorganization may also be referred to as functional rearrangement.

An example of functional reorganization is the capacity of an area of sensory or motor cortex adjacent to an area of injury or necrosis of CNS tissue to control CNS output to a portion of the body that was previously controlled by the injured or necrotic tissue, or to receive and process input from a region of the body from which input was previously received and processed by the injured or necrotic tissue. Another example is the capacity of an area of sensory or motor cortex corresponding in location to an area of injury or necrosis of CNS tissue, but located in the opposite hemisphere of the brain, to control CNS output to a portion of the body that was previously controlled by the injured or necrotic tissue, or to receive and process input from a region of the body from which input was previously received and processed by the injured or necrotic tissue. Yet another example is provided by the nervous system's response to monocular deprivation, which is further discussed below.

Infarct: As used herein, the term "infarct" refers to an area of localized tissue necrosis resulting from inadequate blood supply, e.g., due to obstruction of a blood vessel. Also referred to as an infarction. When the necrotic tissue is brain tissue, the infarct may be referred to as a cerebral infarct or cerebral infarction.

Modulate: As used herein, the term "modulate" means to alter, e.g., to increase or enhance, to decrease or inhibit, or to cause a variation in a temporal pattern. To "modulate a gene" means to modulate the level and/or activity of an RNA or polypeptide expression product of the gene, e.g., by administering an agonist or antagonist. "Level" of an expression product refers to amount, e.g., concentration by weight or volume, number of molecules per cell or by weight or volume, etc. To "modulate a pathway" means to modulate at least one reaction and/or gene involved in the pathway, typically resulting in an alteration in the biological effect or outcome of the pathway. To "modulate a cell" means to increase or enhance, or to decrease or inhibit, the development, survival, and/or activity of the cell.

Neural tissue: As used herein, the term "neural tissue" refers to one or more components of the central nervous system and/or peripheral nervous system. Such components include brain tissue and nerves, which may be present in bundles or tracts. In general, brain tissue and nerves contain neurons (which typically comprise cell body, axon, and dendrite(s)), glial cells (e.g., astrocytes, oligodendrocytes, and microglia in the CNS; Schwann cells in the PNS). It will be appreciated that brain tissue and nerves typically also contain various noncellular supporting materials such as basal lamina (in the PNS), endoneurium, perineurium, and epineuriun in nerves, etc. Additional normeural cells such as fibroblasts, endothelial cells, macrophages, etc., are typically also present. See Schmidt and Leach, 2003, for further description of the structure of various neural tissues.

Peripheral nervous system: As used herein, the term "peripheral nervous system" (PNS) includes the cranial nerves arising from the brain (other than the optic and olfactory nerves), the spinal nerves arising from the spinal cord, sensory nerve cell bodies, and their processes, i.e., all nervous tissue outside of the CNS. The PNS comprises both neurons and glial cells (neuroglia), which are support cells that aid the function of neurons. Glial cells within the PNS are known as Schwann cells, and serve to myelinate axons by providing a sheath that surrounds the axons. In various embodiments of the invention the methods and compositions described herein are applied to different portions of the PNS.

Plasticity: As used herein, the term "plasticity" refers to the capacity of the nervous system, or a portion thereof, to change (e.g., to reorganize) its structure and/or function, generally in response to an environmental condition, injury, experience, or ongoing nervous system activity. Plasticity may involve the proliferation of neurons or glia, the growth or movement of neuronal processes and/or alterations in their shape. Plasticity may involve formation of new synaptic connections between neurons and/or strengthening or weakening of existing synaptic connections. Formation of new synaptic connections may involve growth or movement of neuronal processes. Plasticity may also involve alterations in non-neuronal components of the nervous system, e.g., astrocytes or other glial cells.

Plasticity-modifying agent: As used herein, the term "plasticity-modifying agent" refers to a substance whose administration to a subject, either alone or in combination with one or more other substances or non-pharmacological therapy, results in a detectable alteration in the plasticity of at least a portion of the nervous system. The alteration may be evidenced by an alteration in nervous system function and/or structure as compared with the function and/or structure that would be observed in the absence of the agent. The agent has a clinically significant effect on the nervous system to modify plasticity and is not administered simply for nutritional or dietary purposes. The agent may increase, decrease, and/or prolong plasticity.

Plurality: As used herein, the term "plurality" means more than one.

Polypeptide: As used herein, the term "polypeptide" refers to a polymer of amino acids. As used herein, the term "protein" refers to a molecule composed of one or more polypeptides. The terms "protein," "polypeptide," and "peptide" may be used interchangeably herein. Polypeptides as described herein typically contain only natural amino acids, although non-natural amino acids (i.e., compounds that do not occur in nature in polypeptides but that can be incorporated into a polypeptide chain) and/or amino acid analogs as are known in the art may also be employed.

Proteolysis: As used herein, the term "proteolysis" refers to the breakdown, or degradation, of proteins into smaller polypeptides, typically by cleavage of peptide bonds. Ultimately proteolysis may result in breakdown of the protein into individual amino acids.

Proteolysis-enhancing agent: As used herein, the term "proteolysis-enhancing agent" refers to a substance, e.g., a protease, that increases, contributes to, or causes proteolysis of one or more proteins or inhibits an inhibitor of proteolysis.

Purified: As used herein, the term "purified" means separated from many other compounds or entities. A compound or entity may be partially purified, substantially purified, or pure, where it is pure when it is removed from substantially all other compounds or entities (other than solvents, ions, etc.), i.e., it is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids. In a preferred embodiment a purified protein is removed from at least 90%, preferably at least 95%, more preferably at least 99%, or more, of the other proteins in a preparation, so that the purified protein constitutes at least 90%, preferably at least 95%, more preferably at least 99%, of the material in the preparation on a dry w/w basis.

Recovery: As used herein, the term "recovery" refers to structural and/or functional recovery.

Reorganization: As used herein, the term "reorganization" refers to structural and/or functional reorganization.

RNAi agent: As used herein, the term "RNAi agent" refers to a nucleic acid that inhibits gene expression by an RNAi interference mechanism. Examples include short interfering RNAs (siRNAs), short hairpin RNAs (shRNAs), microRNAs (miRNAs) and nucleic acids that are processed intracellularly, e.g., by a member of the RNase III family of nucleases such as DICER that cleaves double-stranded RNAs, to produce an siRNA, shRNA, or miRNA. It will be appreciated that an RNAi agent, if produced using chemical synthesis, can include one or more deoxyribonucleotides or nucleotide analogs, modified backbone structures, etc., in addition to or instead of ribonucleotides linked by phosphodiester bonds.

Sequential administration: As used herein, "sequential administration" of two or more agents refers to administration of two or more agents to a subject such that the agents are not present together in the subject's body at greater than de minimis concentrations. Thus the agents are not present together in the subject's body in concentrations sufficient for the agents to each have a separate biological effect. In certain embodiments a first agent is administered to a subject. A second agent is administered at a later time at which the concentration of the first agent has declined to less than 1%, less than 5%, or less than 10% of its peak concentration in the CNS or PNS. Administration of the agents may, but need not, alternate. Each agent may be administered multiple times.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Spine dynamics: As used herein, the term "spine dynamics" refers to a change in any of various structural properties of spines over time. The properties include spine shape, size, number, density, and motility. Spine dynamics may be examined with respect to the individual spine or with respect to a plurality (i.e., more than one) of spines.

Spine motility: As used herein, the term "spine motility" refers to a change in spine length over time. When examined with respect to a plurality of spines, spine motility refers to the average change in spine length over time.

Structural recovery: The term "structural recovery," as used in reference to the nervous system or a portion thereof, refers to the partial or complete restoration of a structure that has physically altered, disrupted, or otherwise subjected to a physical or chemical insult, which is intended to include deprivation of oxygen and/or nutrients. "Structural recovery" can also refer to preservation of a structure that has been physically altered, disrupted, or otherwise subjected to a physical or chemical insult, when such physical alteration, disruption, physical or chemical insult would otherwise be expected to lead to deterioration and/or loss or alteration in normal structural features. The structure can be, for example, a synaptic connection, a nerve, nerve bundle, nerve tract, nucleus, brain region, connection between brain regions, etc.

Structural reorganization: The term "structural reorganization," as used in reference to the nervous system or a portion thereof, refers to an alteration in the pattern of connections between two or more neurons or between one or more neurons and one or more glial cells (e.g., astrocytes, oligodendrocytes, microglia, Schwann cells) that takes place over a period of time or an alteration in the position of two or more neuronal or glial cell bodies or cell processes (axons, dendrites, dendritic spines) with respect to one another. The alteration may include the formation of synapses between neurons that did not synapse with each other at the beginning of the time period. The alteration may include the formation of additional synapses between neurons that had at least one synaptic connection at the beginning of the time period. The alteration may also or alternatively include loss of synapses that existed at the beginning of the time period. Reorganization may entail growth or retraction of neural processes such as axons (e.g., axonal sprouting or regeneration), dendrites, or dendritic spines, migration of neurons or glia, and/or neuronal or glial cell division. Structural reorganization may also be referred to as structural rearrangement.

Subject: As used herein, the term "subject" or "individual" refers to an individual to whom an agent is to be delivered, e.g., for experimental, diagnostic, and/or therapeutic purposes and/or an individual who is subjected to a condition that modifies plasticity. Preferred subjects are mammals, particularly domesticated mammals (e.g., dogs, cats, etc.), primates, or humans.

Synapses: As used herein, the term "synapses" refer to "specialized intercellular junctions between neurons or between neurons and other excitable cells where signals are propagated from one cell to another with high spatial precision and speed" (De Camilli, in Cowan, supra). They are the primary sites of intercellular communication in the mammalian nervous system. In general, the basic structure of a synapse consists of a close juxtaposition of specialized regions of the plasma membrane of two neurons, referred to as the presynaptic and postsynaptic neurons, to form a synaptic junction. The presynaptic neuron is the nerve cell transmitting a signal while the postsynaptic neuron is the recipient of the signal. Most neurons in the vertebrate nervous system possess a cell body and two types of cell processes, axons and dendrites. Signals, i.e., action potentials, are initiated and transmitted by the axon while dendrites (and also the cell body) receive inputs via synaptic contacts from other neurons.

Treating: As used herein, the term "treating" generally refers to medical and/or surgical management of a patient for purposes of bringing about an improvement in the state of a subject with respect to a disease, disorder, or condition from which the subject suffers and/or reducing or slowing further deterioration of the subject's condition. Treating can include reversing, alleviating, and/or inhibiting the progress of, the disease, disorder, or condition to which such term applies, and/or reversing, alleviating, inhibiting the progress one or more symptoms or manifestations of such disease, disorder or condition.

DETAILED DESCRIPTION OF CERTAIN EMBODIMENTS OF THE INVENTION

Methods for Identifying Genes, Biological Pathways, and Cells Involved in Plasticity The invention provides methods to identify molecular targets (e.g., genes and their expression product(s)) that may be modulated in order to modify plasticity in the nervous system of an individual. The genes are differentially regulated in at least a portion of the nervous system of individuals subjected to a condition that modifies plasticity. For example, in certain embodiments, inventive methods identify a gene wherein the level and/or activity of an expression product of the gene differs in at least a portion of the nervous system of a subject if the subject has been subjected to a condition known to modify plasticity relative to its expression or activity in that portion of the nervous system in a subject who has not been subjected to the condition or who has been subjected to an alternate condition. In some embodiments, inventive methods identify a gene wherein the level and/or activity of an expression product of the gene differs in a portion of the nervous system that has been subjected to a condition that modifies plasticity relative to its expression or activity in a portion of the nervous system that has not been subjected to a condition that modifies plasticity (e.g., a portion located at a corresponding position of the opposite brain hemisphere of a subject). The portion of the nervous system may be any functionally or structurally defined part, area, region, unit, or component of the nervous system (which terms are used interchangeably herein). Portions of the nervous system include cortex, cerebellum, thalamus, hypothalamus, hippocampus, amygdala, basal ganglia (caudate nucleus, putamen and globus pallidus), midbrain, pons, medulla, nerve tracts, etc., and any sub-portion of the foregoing. For example, sub-regions of the cortex include visual cortex, auditory cortex, somatosensory cortex, entorhinal cortex, olfactory cortex, Broca's area, Wernicke's area, etc. It will be appreciated that these regions themselves may be composed of smaller sub-regions. For example, the primate cortex has been divided into Brodmann areas 1-49 and 52, some of which include subareas, based on cytoarchitectural distinctions. Important areas of the primate visual cortex are referred to as V1, V2, V3, V4, and MT (also referred to as V5). Portions of the nervous system also include the six major cortical layers (I-VI) and their sublayers. Portions of the nervous system also include cortical columns, a term that refers to collections of cells arranged vertically from the surface of the cortex to the white matter that comprise functional and/or anatomical units. Thus, a cortical column can be defined on the basis of anatomical features (e.g. stereotyped patterns of pyramidal cell apical dendrite bundles), functional features (e.g. columns of cortical cells all responding to the same stimulus orientation) or both. Cortical columns include ocular dominance, orientation, spatial frequency, and color columns. In certain embodiments, the portion of the nervous system comprises cells of one or more types, e.g., one or more neuronal cell types. Cells may be excitatory or inhibitory. Exemplary cell types found in the nervous system include pyramidal cells, stellate cells, interneurons (e.g., chandelier cells, neurogliaform cells, basket cells, double basket cells, Purkinje cells, granule cells, Cajal-Retzius cells, Meynert cells, etc.).

Inventive methods are applied herein to identify genes that are differentially regulated in the visual cortex under monocular deprivation or dark rearing, both of which are conditions known to modify plasticity. The invention identifies biological pathways enriched in such genes.

The invention provides a method of identifying a gene involved in plasticity (referred to herein as a "plasticity-related gene") comprising steps of: (i) subjecting an individual to a condition that modifies plasticity; (ii) measuring level or activity of each of a plurality of genes in at least a portion of the individual's nervous system; and (iii) identifying one or more genes whose expression or activity is differentially regulated in the portion of the individual's nervous system relative to its expression or activity under alternative conditions. Conditions may be environmental conditions that are deficient in one or more environmental stimuli that the individual would normally experience. Conditions may include one or more environmental stimuli that the individual would not normally experience. Alternative conditions may be normal environmental conditions, e.g., standard laboratory conditions. Conditions suitable for maintaining animals are discussed in Guide for the Care and Use of Laboratory Animals, Institute for Laboratory Animal Research (ILAR) Commission on Life Sciences, National Research Council, National Academies Press, Washington, D.C. (1996). It will be appreciated that a range of conditions may be considered "normal" but will generally not include specific efforts to deprive or supplement the nervous system inputs that typically would be received be animal maintained as described in the foregoing reference.

Inventive methods may include identifying one or more biological processes or pathways involving one or more of the plasticity-related genes. The biological process pathway may be enriched for genes identified by the method. For example, the biological process or pathway may include a higher proportion of genes identified by the method than would be expected based on the number of genes in the process or pathway and the number of known genes in an individual of that particular species. In other words, genes identified as being differentially regulated are over-represented among the genes in the biological process or pathway. See Examples for further details.

In certain embodiments of the invention, the individual is subjected to the condition during at least a portion of a critical period for development of one or more nervous system structure(s), functions, or properties. Nervous system structures, functions, or properties for which a critical period has been well documented in one or more species include ocular dominance, orientation bias, development of the neuromuscular junction, climbing fiber refinement, whisker barrel map formation, whisker RF tuning, cortical tonotopic map, sound localization, birdsong, and human language. The conditions may include depriving the individual of normal inputs needed for the establishment of any of these structures, functions, or properties. The timing of critical periods and the effects of specific environmental conditions are known in the art (see, e.g., Hensch, 2004, *Annu. Rev. Neurosci.,* 27:549).

In certain embodiments of the invention, conditions include subjecting a subject to an alteration in visual input, optionally during a critical period for development of the visual cortex. Alteration of visual input during postnatal development causes adaptive changes in the maturation of visual cortex circuitry. One method of use for identifying genes, biological pathways, and cells involved in activity-dependent plasticity is to alter visual experience during a critical period of development. The timing of such critical periods for development of the visual system is known in the art[4]. One example of altering visual experience is to raise animals in complete darkness from birth (dark rearing). Dark-rearing (DR) has diverse effects on the visual cortex, causing an upregulation of miniature synaptic potentials in subsets of neurons[5], a reduction in spine number together with an increase in area of the spines that remain[6], a change in the threshold for eliciting synaptic potentiation and depression[7, 8], and a prolongation of the critical period for eliciting experience dependent changes in visual function[9].

One example of manipulation of use to study the influence of activity on visual cortex neurons and networks and to identify genes, biological pathways, and cells involved in plasticity is monocular deprivation (MD). In animals with binocular vision, inputs to a portion of the visual cortex become anatomically and functionally segregated into alternating stripes of input from the two eyes, referred to as ocular dominance columns. As a consequence, individual cortical neurons that were originally responsive to both eyes become responsive to only one eye. However, if one eye is deprived of visual input during a critical period (monocular deprivation), that eye loses most of its ability to activate the cortex, and the responses of cells shift towards the nondeprived eye eye, i.e., ocular dominance (OD) shifts in favor of the nondeprived eye. The rapid appearance of the functional deficit is followed by structural changes including a reduction in cortical area driven by the deprived eye and expansion of the area driven by the nondeprived eye, which take place on a timescale of weeks to months. The extent and complexity of thalamocortical axonal arbors from the deprived eye are reduced, while the extent and complexity of arbors from the nondeprived eye increase. MD, which can be achieved by suturing the lids of one eye during the critical period, causes an increase in the proportion of neurons in the binocular part of the V1 region of the cortex that respond to the open eye[13]. Short-term MD causes a reorganization of intracortical connections both functionally and structurally[14-17], whereas long-term MD leads in addition to a reduction of thalamocortical arbors from the deprived eye and an expansion of arbors from the non-deprived eye[18,19].

The individual can be subjected to the condition during all or part of a critical period, e.g., for a total of between 10% and 100% of the critical period. The individual can be subjected to the condition intermittently or continuously. In certain embodiments of the invention the critical period is, e.g., between 24 hours and 1 year in length, e.g., between 24 hours and 60 days in length. The critical period can commence at any time after birth or even prior to birth and may terminate at any later time, depending upon the particular nervous system structure(s), functions, or properties under consideration.

Any suitable method can be used to identify the differentially regulated genes. In general, the methods involve obtaining samples of nervous system tissue (e.g., samples of tissue from a portion of the brain such as cortex, hippocampus, etc.) from a subject who has been subjected to a condition (e.g., a reduction in or increase in inputs) that modifies plasticity in at least a portion of the nervous system. The level and/or activity of each of a plurality of gene products is measured in the sample and is compared with the level and/or activity that would exist under alternate conditions. The method can involve obtaining a sample of nervous system tissue from a different subject who has not been subjected to the condition or obtaining a sample of nervous system tissue from the same subject but from a portion of the nervous system that has not been subjected to the condition. The level and/or activity in the two samples can be compared in an experiment performed on the two samples. Alternatively or additionally, a comparison with previously gathered data on expression levels and/or activity can be used.

Methods for determining the level of a gene product are well known in the art, and any suitable method can be used. For example, if the gene product is an RNA, its level can be measured using cDNA or oligonucleotide microarrays, subtractive hybridization, Northern blots, quantitative reverse transcription polymerase chain reaction (RT-PCR), etc. If the gene product is a polypeptide, its level can be measured using a variety of immunologically based methods such as immunohistochemistry, enzyme-linked immunosorbent assay (ELISA), Western blot, protein array technology (e.g., antibody arrays or arrays using other specific binding agents, etc.).

Activity of a gene product can also be measured in a variety of ways that will typically depend upon the specific gene product whose activity is being measured. For example, if the gene product is a kinase or phosphatase, the extent to which an endogenous substrate is phosphorylated provides an indication of the activity of the gene product. The substrate is isolated from cell in which it is expressed, and its phosphorylation state is evaluated. Alternatively or additionally, in vitro kinase or phosphatase assays can be performed. If the gene product is a transcription factor, an assay that involves measuring expression of a reporter construct that contains a DNA element responsive to the transcription factor can be used. The activity of certain polypeptides is regulated by post-translational modification, localization, and/or physical association (typically noncovalent binding) with one or more cellular structures or molecules. For example, certain polypeptides are activated or inactivated by phosphorylation. Activity may be assessed using binding assays, assays that determine subcellular localization or association with particular intracellular structures or molecules, assays that determine modification state, electrophoresis, mass spectrometry, etc. One of skill in the art will be able to select appropriate methods for determining and comparing the activity of gene products.

In certain embodiments of the invention a highly parallel method is used. By "highly parallel" is meant that the method determines the level or activity of at least 10 gene products essentially simultaneously and/or in a single experiment. Examples include microarray analysis and protein array analysis, wherein the array comprises at least 10 features (e.g., at least 10 specific binding agents such as oligonucleotides or antibodies are affixed to the array). In certain embodiments of the invention the highly parallel method determines the level or activity of at least 100, at least 1000, at least 10,000, or at least 100,000 gene products essentially simultaneously and/or in a single experiment.

Many of the genes that have been or will be identified using the above methods are components of one or more biological processes or pathways. Such biological processes or pathways may be identified using a variety of methods. One of skill in the art will be familiar with processes and pathways in which some of the genes play a role or will be able to identify such processes and pathways by searching the literature or by using readily available biological information resources.

One biological information resource of particular use is the Gene Ontology project (www.geneontology.org). The Gene Ontology (GO) provides a list of three structured, controlled vocabularies (ontologies) that describe gene products and their associated biological processes and cellular constituents using a uniform terminology. In particular, the Gene Ontology database annotates (and thereby associates) identifiers of gene products (e.g., gene names) with identifiers of biological processes of which those gene products are components. The Gene Ontology database can thus be used to identify the gene products that carry out a particular biological process and/or to identify the biological processes in which any gene product of interest plays a role. While the Gene Ontology database is used herein to exemplify the identification of biological processes and pathways that involve genes that are differentially regulated in the nervous system of an individual subjected to a plasticity-modifying condition, any similar compilation of information that associates identifiers of biochemical species with identifiers of biological processes and/or pathways could be used instead of, or in addition to, the Gene Ontology database. For example, the Kyoto Encyclopedia of Genes and Genomes (KEGG) offers somewhat similar facilities.

Numerous additional computer-based resources that provide convenient, unified access to biological information are available on the World Wide Web.

In certain embodiments, biological processes or pathways whose components (e.g., genes) are over-represented among the plasticity-related genes are identified as likely to be involved in modifying plasticity, i.e., they are identified as plasticity-related processes or pathways. A gene (or other biochemical species) that is a component of a biological process is over-represented among the plasticity-related genes if the likelihood that the number of plasticity-related genes that are associated with that biological process is greater than the number of plasticity-related genes that would be expected to be associated with that biological process based on the number of plasticity-related genes identified and the number of genes that are components of the biological process or pathway. Genes that are components of a biological process or pathway identified as being a plasticity-related process or pathway are candidate plasticity-related genes even if they are not themselves differentially regulated under plasticity-modifying conditions. For example, a first polypeptide that acts as a ligand, receptor, substrate, or binding partner for a second polypeptide whose expression is differentially regulated under plasticity-modifying conditions may be a component of a biological pathway of which the first polypeptide is a component and may be modulated instead of, or in addition to, modulating the first polypeptide.

In certain embodiments of the invention, once a gene, pathway, or process is identified using the methods described above, its role in nervous system structure(s), functions, or properties is more precisely evaluated using any of a variety of approaches. Certain of these approaches are also useful to modulate plasticity for therapeutic purposes, e.g., to improve recovery or reorganization of the nervous system in a subject in need of recovery or reorganization. For example, an agent that modulates the gene, pathway, or process can be administered to an individual and the effect of the agent on the nervous system is determined. The individual may or may not be subjected to a plasticity-modifying condition such as a deprived or enriched condition. The agent can be administered during all or part of the period of time over which the individual is subjected to the condition. In certain embodiments, a transgenic non-human animal (e.g., a mouse or rat) that has temporally and/or spatially altered expression of the gene (e.g., that lacks or has reduced expression of the gene or has elevated or ectopic expression of the gene) is analyzed to determine whether the animal has altered nervous system structure or function and/or altered plasticity relative to an animal in which expression of the gene is not altered (e.g., a "wild type" animal). The transgenic animal can be generated using standard methods known in the art and is an aspect of this invention. In certain embodiments, an agent that modulates a gene, pathway, or process that is differentially regulated in individuals subjected to a plasticity-modifying condition is administered to a non-human animal. The animal may or may not be subjected to a plasticity-modifying condition or an event that damages the nervous system. The animal exhibits altered plasticity relative to an animal to which the agent is not administered. The animal is used as a model to screen for additional agents that are useful to alter plasticity and/or promote reorganization or recovery of the nervous system.

In certain embodiments of the invention, an agent that modulates a gene that is a component of a plasticity-related biological process or pathway is administered. The gene itself may or may not be differentially regulated under a plasticity-modifying condition. In some instances, agents that modulate particular genes, pathways, or pathways will be known to those of skill in the art. Any such agent can be used. In certain embodiments of the invention an RNAi agent such as an siRNA or shRNA is used to inhibit expression of a gene, e.g., by triggering degradation of mRNA transcribed from the gene. RNA-mediated interference (RNAi) has recently emerged as a powerful method to reduce the expression of any target transcript in mammalian cells (see, e.g., Elbashir, 2001; Brummelkamp, 2002; McManus & Sharp, 2002; and U.S. Patent Publications 2005/0026278, 2004/0259248, and 2003/0108923). Briefly, it has been found that the presence within a cell of a short double-stranded RNA molecule referred to as a short interfering RNA (siRNA), one strand of which is substantially complementary to a transcript present in the cell (the target transcript) over a length of about 17-29 nucleotides, results in inhibition of expression of the target transcript. The mechanism typically involves degradation of the transcript by intracellular machinery that cleaves RNA (although translational inhibition can also occur). Short hairpin RNAs are single-stranded RNA molecules that include a stem (formed by self-hybridization of two complementary portions of the RNA) and a loop. The stem-loop structure can be processed intracellularly into an siRNA. In some embodiments, an antibody, aptamer, or other molecule with specific binding properties is used to modulate activity of a polypeptide. In some embodiments, a ligand (e.g., an agonist or antagonist) is used to modulate activity of a receptor. In certain embodiments of the invention, the agent is one that can cross the blood brain barrier so as to achieve an effective concentration in the CNS when administered to the subject at a location outside the nervous system (e.g., orally, intravenously, intraperitoneally) at concentrations that do not cause unacceptable side effects.

In certain embodiments, antisense oligonucleotides complementary to an mRNA transcript that encodes a polypeptide, or ribozymes that cleave the mRNA transcript, are used to decrease expression. Antisense oligonucleotides, or a vector that provides a template for intracellular synthesis of an antisense oligonucleotide, or cells that synthesize the oligonucleotide, can be administered. Antisense technology and its applications are well known in the art and are described in Phillips, M. I. (ed.) "Antisense Technology," *Methods Enzymol.*, Vol. 313 and 314, Academic Press, San Diego, 2000, and references mentioned therein. See also Crooke, S. (ed.) "Antisense Drug Technology: Principles, Strategies, and Applications" (1$^{st}$ ed), Marcel Dekker, ISBN: 0824705661, 1st edition (2001), and references therein.

In some embodiments, an aptamer that binds to a polypeptide and inhibits its activity is used. An aptamer is an oligonucleotide (e.g., DNA, RNA, which can include various modified nucleotides, e.g., 2'-O-methyl modified nucleotides) that binds to a particular protein. Aptamers are typically derived from an in vitro evolution process (SELEX), and methods for obtaining aptamers specific for a protein of interest are known in the art (see, e.g., Brody, 2000).

Ribozymes and deoxyribozymes are RNA and DNA molecules that can act as enzymes by folding into a catalytically active structure that is specified by the nucleotide sequence of the molecule. Such molecules have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation (Cotten and Birnstiel, 1989; Usman, 1996; and Sun, 2000).

It will be appreciated that synthetic nucleic acids such as siRNA, antisense oligonucleotides, aptamers, ribozymes, etc., can include RNA, DNA, nucleoside analog(s), and/or may included modified sugars, or modified backbone structures.

Expression or activity of a gene, pathway, or process identified using the methods of the invention can be modulated as described above for purposes of modifying nervous system structure(s), functions, or properties. These approaches are of use to modulate plasticity for therapeutic purposes, e.g., to improve recovery or reorganization of the nervous system in a subject in need of nervous system recovery or reorganization.

The invention provides methods for modifying plasticity by modulating particular cell types present in the nervous system. Cells present in the nervous system have been classified into a number of different cell types based on their level of expression of a molecule or portion thereof, or a set of two or more molecules or portions thereof (referred to herein as "markers"). The molecule or portion thereof may be, e.g., a particular gene product, a lipid, a carbohydrate modification of a polypeptide or lipid, etc., (referred to herein as "markers"). The marker(s) are said to be characteristic of the cell type. Cells may be classified into types with varying degrees of specificity. For example, the cell type may be an interneuron or may be more specifically classified as being a particular type of interneuron. Certain cell types may be identified based on their expression of a single marker. Other cell types may be identified based on their expression of two or more markers (referred to as a "set" of markers), in which case each marker may be expressed in more than one cell type with specific sets of markers serving to identify specific cell types. In some instances the cell is identified based on whether or not the marker is detectably present in the cell or at its surface at significant levels (above background). In some instances the cell is identified as being of a particular type based on the level at which the marker is present in the cell relative to the level at which it is present in cells of other types. Markers include molecules and portions thereof, wherein absence of the molecule or portion thereof may in part be used to classify cells into different types. Expression of a marker or a specific set of markers may correlate with various parameters such as morphology (e.g., branching pattern of neuronal processes), location, and/or electrophysiologic properties.

The invention provides methods for selecting a cell type as a target for modulation to regulate plasticity based on identifying genes that are differentially regulated under plasticity-modifying conditions. Cells of the cell type are involved in regulating one or more aspects of plasticity. Cells of the cell type may play a role in maintaining or terminating a critical period. They may play a role in modifying the ability of other cells to respond to inputs, e.g., nerve impulses arising as a result of environmental stimuli. They may regulate formation of new synaptic connections between neurons and/or regulate the strengthening or weakening of existing synaptic connections. The invention provides methods of selecting a cell type as a target for modulation comprising steps of: (i) subjecting an individual to a condition that modifies plasticity; (ii) measuring level or activity of each of a plurality of genes in at least a portion of the individual's nervous system; (iii) identifying one or more genes whose expression or activity is differentially regulated in the portion of the individual's nervous system relative to its expression or activity under alternative conditions; and (iv) selecting a cell type as a target for modulation, wherein a product of at least one of the genes is a marker of the cell type. "Product" here refers to an expression product of the gene or to a molecule or molecular modification that is present in a cell or at its surface as a result of the expression of the gene. For example, if the gene encodes a kinase, the "product" may be the phosphorylated form of a substrate of the kinase. In certain embodiments of the invention, the cell type expresses at least two of the differentially regulated genes or expresses at least one of the differentially regulated genes and does not significantly express at least one of the differentially regulated genes. The method may include determining that the number of cells of the cell type is altered in at least a portion of the nervous system of an individual subjected to a plasticity-modifying condition. For example, immunohistochemistry or in vivo imaging can be used to evaluate cell number.

The marker may be any marker recognized in the art as useful to classify cells present in the nervous system into different cell types. In certain embodiments of the invention, the marker is a calcium binding protein. A variety of calcium binding proteins (CBPs) such as calbindin, parvalbumin, and calretenin are recognized in the art as being markers of different types of interneurons (Markram et al., 2004, *Nat. Rev. Neurosci.*, 5:793; and Flames et al., 2005, *Neuron*, 46:377). The marker may be a neuropeptide such as somatostatin, vasoactive intestinal peptide, neuropeptide Y, or cholecystokinin. These neuropeptides are recognized in the art as being markers of different types of interneurons (Markram, 2004; and Flames and Marin, 2005). Certain cell types are identified based on their expression of one or more CBPs and one or more neuropeptides.

In illustrative embodiments, as described in the Examples, inventive methods are applied to identify the gene that encodes parvalbumin (PV) as being down-regulated (under-expressed) in the visual cortex under conditions of DR, which conditions prolong the state of plasticity associated with the critical period. The invention further identifies PV expressing interneurons as being reduced in number in visual cortex under conditions of DR. Thus in certain embodiments of the invention, the cell type selected as a target for modulation is a PV-expressing interneuron, i.e., parvalbumin is a marker of the cell type selected as a target for modulation. In the cortex, interneurons that express PV are inhibitory interneurons that utilize γ-aminobutyric acid (GABA) as their neurotransmitter and are morphologically classified as basket cells and chandelier cells (Markram, 2004).

The invention includes computer-readable media (e.g., a hard disk, floppy disk, compact disk, zip disk, flash memory, magnetic memory, etc.) that store information related to any of the methods described above. Information may be organized in the form of a database, i.e., a collection of data that is organized so that its contents can easily be accessed, managed and updated. Information may identify one or more genes that are differentially regulated in at least a portion of the nervous system of an individual subjected to plasticity-modifying conditions, optionally under conditions in which an agent is administered to an individual during or after the time period in which the individual is subjected to plasticity-modifying conditions. Genes can be identified by name, by sequence, by accession number(s), etc. It will be appreciated that the information about expression and/or activity may relate to the genes themselves and/or to any of their expression products (RNA or protein). The information may indicate the nature of the conditions under which differential regulation was observed, may identify genes whose expression is altered by a plasticity-modifying agent, etc. Genes may be listed in order or ranked, e.g., according to the significance of their differential regulation. Exemplary collections of such information are provided in Tables 4-11. Computer-readable media may store information identifying genes that are not differentially regulated, provided that they also include information pertaining to genes that are differentially regulated and identifies those genes as being relevant to plasticity, to nervous system structure, function, recovery or reorganization, etc. Additional information related to the gene(s) and/or to their role in plasticity or nervous system recovery or reorganization can be included, e.g., (i) quantitative information related to the extent to which the gene(s) is/are differentially regulated and/or its significance; (ii) information identifying a biological pathway or process enriched in one or more of the genes; (iii) results obtained by administering an agent that modulates expression or activity of one or more of the genes to a subject, etc. The invention also includes methods comprising the step of electronically sending or receiving any of the afore-mentioned information and, optionally, storing at least part of the information and/or creating a new computer-readable medium or copy containing at least part of the information.

Compositions and Methods for Modulating Plasticity and Promoting Nervous System Reorganization and Recovery The present invention is based in part on the identification of genes that are differentially regulated in response to particular environmental conditions that modify plasticity, namely dark rearing and monocular deprivation. The invention is based in part on the identification of biological processes and pathways that are enriched for one or more of these differentially regulated genes and are therefore considered herein to be differentially regulated pathways. In some embodiments, the present invention encompasses the recognition that expression products of certain genes that are differentially regulated in response to DR and/or MD are involved in plasticity. In some embodiments, the present invention encompasses the recognition that certain of these genes are implicated as being involved in structural and/or functional nervous system reorganization following nervous system damage and can be manipulated to achieve therapeutic benefit. In some embodiments, the present invention encompasses the recognition that certain of these expression products, and agents that modulate their expression and/or activity, are of use to promote nervous system recovery and/or reorganization following nervous system damage, e.g., following ischemic, hemorrhagic, neoplastic, degenerative, traumatic, and/or neurodevelopmental damage and/or to inhibit nervous system deterioration that would otherwise occur, e.g., as a result of deprivation of input.

The invention identifies (i) genes whose expression is downregulated in visual cortex under conditions of DR (Table 4), (ii) genes whose expression is upregulated in visual cortex under conditions of DR (Table 5), (iii) genes whose expression is downregulated in visual cortex under conditions of long term MD (Table 6), (iv) genes whose expression is upregulated in visual cortex under conditions of long term MD (Table 7), (v) genes whose expression is downregulated in visual cortex under conditions of short term MD (Table 8), and (vi) genes whose expression is upregulated in visual cortex under conditions of short term MD (Table 9). The invention identifies genes that are differentially regulated in visual cortex under conditions of short term MD in subjects who are treated with a plasticity-modifying agent, namely an activator of the IGF1 pathway (Tables 10 and 11). These genes are identified as candidates for modulation to modify plasticity and/or to promote functional and/or structural nervous system reorganization or recovery of the nervous system. The genes were identified at least in part by hybridizing mRNA to a microarray from Affymetrix (www.affymetrix.com) that contained probes for a large number of mouse genes (see Example 1). The numbered rows in Tables 4-11 list (from left to right, separated by spaces or tabs) the Affymetrix identifier of the probe, the p value, the data for experimental condition (e.g., MD or DR) and control, the gene symbol corresponding to the probe (where available), accession number(s) for the genes and/or proteins, and Reference Sequence (RefSeq) identifier. Items that are not available or not included are indicated by - - - -. It will be appreciated that the entries in the tables can be arranged in a number of different ways and the specific ordering presented in the tables is not intended to be limiting. For example, the entries can be listed and/or ranked on the basis of ascending p value, on the basis of the absolute or relative magnitude of the difference in expression between the experimental and control conditions, etc.

One of ordinary skill in the art will be able to obtain additional information about the genes and their expression product(s) listed in Tables 4-11 and/or discussed herein, e.g., their sequences, by searching public databases such as those available through Entrez, the search and retrieval system used at the National Center for Biotechnology Information (www.ncbi.nlm.nih.gov) for databases, including PubMed, Nucleotide and Protein Sequences (e.g., Genbank), Protein Structures, Complete Genomes, Taxonomy, etc., (www.ncbi.nlm.nih.gov/gquery/gquery.fcgi). These databases can be searched using the symbols or names of the genes. One of skill in the art will also recognize that additional information can be found at the publicly available Affymetrix website, Netaffx Analysis Center (www.affymetrix.com/analysis/index.affx), visited Apr. 12, 2006, which allows one to correlate GeneChip® array results with array design and annotation information and can be queried by ID. The website includes libraries for each microarray that provide the IDs of the probes and accession numbers for the corresponding genes and proteins.

The invention provides methods for modifying plasticity in the nervous system of a subject comprising steps of: administering a plasticity-modifying agent to a subject in need thereof, wherein the agent is administered either alone or in combination with one or more additional agents in an amount effective to modify nervous system plasticity, wherein the plasticity-modifying agent modulates a gene or pathway that is differentially regulated in at least a portion of the nervous system of an individual subjected to a plasticity-modifying condition. In other words, when administered to the subject, the agent modulates a gene or pathway, wherein the gene or pathway is a gene or pathway that is differentially regulated in the nervous system of an individual subjected to a plasticity-modifying condition, e.g., a gene or pathway identified using the methods of the present invention. The subject to whom the agent is administered may or may not be subjected to a plasticity-modifying condition. In certain embodiments of the invention, the plasticity-modifying condition is DR or MD. In certain specific embodiments, the plasticity-modifying condition is MD. In certain embodiments of the invention the agent modifies plasticity in a manner that depends on nervous system activity, e.g., the extent to which the nervous system undergoes structural or functional alteration in the presence of the agent will depend on the type of inputs received by the nervous system and/or the type of stimuli to which the nervous system is subjected. In certain embodiments of the invention, the agent enhances the ability of the nervous system to modify its structure or function in response to the presence of a second agent such as a neural growth enhancing agent. Thus the plasticity-enhancing agent may at least in part play a permissive role, contributing to structural or functional recovery or reorganization in the nervous system when administered to a subject who is receiving rehabilitative therapy that modifies nervous system inputs or who is receiving a neural growth enhancing agent.

The invention further provides methods of promoting reorganization or recovery in the nervous system of a subject comprising steps of: administering a plasticity-modifying agent to a subject in need thereof, wherein the agent is administered either alone or in combination with one or more additional agents in an amount effective to promote nervous system reorganization or recovery, wherein the plasticity-modifying agent modulates a gene or pathway that is differentially regulated in at least a portion of the nervous system of an individual subjected to a plasticity-modifying condition, e.g., conditions of DR or MD. The subject may have suffered ischemic, hemorrhagic, neoplastic, traumatic, neurodegenerative, toxic, and/or neurodevelopmental damage to the nervous system. The agent may contribute to (e.g., enhance) recovery or reorganization in the subject's nervous system and/or promote normalization of function. In other words, the degree of reorganization or recovery of the nervous system, or improvement of function, is greater than would have been the case if the agent had not been administered to the subject. In certain embodiments of the invention, the agent does not act solely or primarily by exerting a neuroprotective effect, e.g., does not act solely or primarily by inhibiting cell death or dysfunction (e.g., necrosis or apoptosis). In certain embodiments of the invention, the agent exerts both a neuroprotective effect and a plasticity-enhancing effect. According to certain embodiments of the invention, the agent is capable of exerting a neuroprotective effect but is administered within a particular time window subsequent to a specific damaging event such as a stroke, at a time that falls outside the time window during which the agent would exert a neuroprotective effect.

The above methods may modify plasticity and/or promote recovery or reorganization in any one or more portions of the nervous system. For example, in certain embodiments of the invention, a method modifies plasticity, e.g., promotes plasticity, and/or promote recovery or reorganization in at least a portion of the visual cortex. In certain embodiments of the invention, the portion of the nervous system is one located in proximity to an implanted drug delivery device. For example, the portion of the nervous system may be located up to 1, 2, 3, 4, 5, 6, 7, 8, 9, or 10 centimeters (cm) away from the surface or border of the device.

Typically, agents and compositions in accordance with the invention promote structural reorganization and/or functional reorganization of the nervous system or a portion thereof or maintain the nervous system in a state in which such reorganization can occur. In certain specific embodiments, agents of the invention promote structural and/or functional recovery of the nervous system or a portion thereof. It will be appreciated that often there will be a correlation between (i) structural reorganization and/or recovery and (ii) functional reorganization and/or recovery, e.g., both structural reorganization and/or recovery as well as functional reorganization and/or recovery take place. However, in some embodiments of the invention, functional reorganization and/or recovery take place without detectable evidence of structural reorganization and/or recovery. In some embodiments of the invention, structural reorganization and/or recovery take place without detectable evidence of functional reorganization and/or recovery during a particular time period of evaluation. In such embodiments, functional reorganization and/or recovery may occur at a later time, and/or the recovery may not be detected using the particular measurement tools and methods used for the evaluation. It will also be appreciated that reorganization is typically associated with recovery, but reorganization can precede noticeable evidence of recovery, sometimes by a significant period of time.

Functional recovery from damaging events may involve regrowth of physical connections (e.g., synapses) between surviving nervous system cells (e.g., neurons, glial cells) and/or establishment of new connections. Certain of the plasticity-modifying agents may interact directly with cells (e.g., neurons, glial cells, etc.) to enhance their plasticity and/or stimulate their capacity for structural and/or functional reorganization. Agents may be administered in conjunction with an agent that causes degradation of molecule(s) present in the ECM that would otherwise impede beneficial structural changes or would exert inhibitory effects on nervous system cells. In certain embodiments of the invention, two or more agents are administered concurrently or sequentially to a subject. Either or both of the agents may be focally administered to the nervous system of the subject.

Plasticity-Modifying Agents

The invention identifies a number of genes and biological pathways that may be modulated to modify plasticity. Before discussing certain of these genes and pathways it should be noted that certain of the genes and their encoded polypeptides discussed herein are members of families, and in some cases multiple isoforms of a particular polypeptide exist, as well as post-translationally modified forms (e.g., forms that have been modified by phosphorylation, glycosylation, acylation, etc.). In such cases a single name may be used to collectively refer to multiple genes or polypeptides. For example, "PI3K" refers to any member or set of members of the PI3K family. "AKT" refers to at least Akt1, Akt2, and/or Akt3, etc. "STAT" refers to at least STAT1 2, 3, 4, 5a, 5b, 6, and/or 7, etc. "JAK" refers to at least JAK1, JAK2, JAK3, and/or Tyk2, etc. Similarly, the "JAK/STAT pathway" refers to any pathway involving at least one JAK and at least one STAT. It will be appreciated that in certain embodiments of the invention it will be desirable to selectively modulate one or more members of a family, e.g., one or more members that is/are present in the nervous system. It will be also be appreciated that multiple variant polypeptides encoded by a single gene may arise from RNA and/or protein splicing and that gene editing can also give rise to variants, all of which may be referred to by the same name or symbol herein. The invention thus includes embodiments in which any one or more members of a family, isoforms, splice variants that arise from RNA or protein splicing or gene editing, post-translationally modified forms, etc., are modulated.

One of ordinary skill in the art will readily understand which particular genes and gene products (e.g. mRNA and polypeptides) are referred to using the names listed herein and will be able to retrieve the sequences of these genes and gene products and relevant information such as sources from which the molecule can be purified or obtained using, e.g., publicly available databases such as Genbank and PubMed. For example, one of skill in the art can search the Entrez Gene database provided by the National Center for Biotechnology Information (NCBI), available at the web site having URL www.ncbi.nlm.nih.gov/entrez/query.fcgi?CMD=search&DB=gene and can thereby locate the Gene ID for any particular gene or polypeptide of interest. It will be appreciated that allelic variants, homologs, and biologically active fragments or variants of the molecules described herein also be used.

In some embodiments (described in more detail in the Examples), IGFBP5 is identified as being differentially regulated under a particular deprived condition (MD). IGFBP5 is a component of the IGF1 pathway. The invention contemplates modulating one or more components of the IGF1 pathway in order to modify plasticity. The invention contemplates modulating one or more components of the IGF1 pathway to promote recovery or reorganization of the nervous system in a subject in need thereof.

As described in the Examples, IGFPB5 is significantly upregulated under conditions of MD in the visual cortex of subjects that are subjected to MD. IGFBP5 is one of the most upregulated genes after MD both at the mRNA and protein level. Furthermore, the IGF1 pathway is one of the biological pathways that is most enriched for genes that are differentially regulated after MD, and both IGFBP5 and IGF1 are constituents of several highly enriched pathways after MD. Therefore, the IGF1 pathway is identified as being a plasticity-related pathway of particular interest. As described in Example 4, administration of an activator of the IFG1 pathway prevented many of the effects of monocular deprivation on the V1 region of the cortex. To the best of the inventors' knowledge, these results represent the first evidence showing the possible functional involvement of the IGF1/IGFBP5 system in experience-dependent plasticity in the cortex. The results demonstrate that IGF1 and/or pathways and mechanisms involving IGF1 stabilize synapses and alter plasticity.

IGF1 is a member of a superfamily of growth-promoting peptides related to insulin in sequence and biological activity. The actions of IGF1 are mediated by the type I IGF receptor (IGF1R), which transmits binding of IGF1 to an intracellular signaling cascade. Binding of IGFs to the IGF1R enhances the receptors's tyrosine kinase activity, resulting in phosphorylation of insulin receptor substrates IRS1-IRS4, which leads to activation of two major downstream signaling pathways, the mitogen activated protein kinase (MAPK) and the phosphoinositide 3-kinase (PI3K) pathways. The PI3K pathway is discussed further below. Six IGF binding proteins (IGFBP1-GFBP6) regulate the biological activity of IGF1 by a variety of mechanisms, and some of the IGFBPs have effects independent of IGF1. IGF1, IGF1R, and certain of the IGFBPs are expressed in the CNS and have been postulated to have a variety of different functions therein (Russo, 2005). IGF1 interacts with a variety of different proteins, and activation of the IGF1 pathway results in phosphorylation of a large number of downstream substrates.

The IGF1 pathway can be modulated using a variety of different methods. In certain embodiments of the invention, the pathway is modulated so as to increase the activity of the pathway. IGF1 or a biologically active fragment thereof can be administered to the subject to activate the pathway. In some embodiments, the tripeptide GPE is used. Alternatively or additionally, a different ligand of an IGF receptor can be administered. The ligand can be an agonist or antagonist, depending on whether it is desired to inhibit or activate the receptor. In some embodiments, methods include (i) administering agent that disrupts the physical association between IGF1 and an IGFBP; (ii) administering an agent that activates or inhibits a kinase that phosphorylates one or more IGF1 substrates; (iii) administering an agent that activates or inhibits a phosphatase that dephosphorylates one or more IGF1 substrates; (iv) administering an agent that upregulates expression of IGF1 or IGF1R; (v) administering an agent that upregulates or downregulates expression of an IGFBP; (vi) administering an agent that increases the expression or activity of a component of the PI3K, and/or Akt signaling cascade. etc. In one embodiment, an RNAi agent is used to inhibit expression of one or more genes in the pathway, e.g., a gene encoding an IGF binding protein such as IGFBP5.

In certain embodiments of the invention, the phosphoinositide 3-kinase (PI3K) signal transduction pathway is modulated. Phosphoinositide 3-kinase, also referred to as phosphatidylinositol 3-kinase, is a lipid kinase and a serine/threonine kinase that is a component of a signal transduction pathway involving Src-like or receptor tyrosine kinases such as the IGF1 receptor. Thus, the PI3K pathway is responsible at least in part for the actions of IGF1. The PI3K kinase superfamily includes a large number of structurally related enzymes with differing regulation and substrates (see Foster, 2003 and Paez et al., 2003, for reviews). "Classical" PI3K comprises a regulatory subunit (p85) and a 110-kDa catalytic subunit (p110). PI3K acts through a downstream effector protein kinase B (PKB, also named Akt) to regulate many cellular processes including cell survival, cell proliferation, vesicular trafficking, inflammation and apoptosis inhibition. Three isoforms of Akt (Akt1, Akt2, and Akt3) are known. When activated, PI3K phosphorylates phosphoinositides at the 3' position of the inositol ring. Following their phosphorylation the phosphoinositides promote Akt activation by phosphorylation. Activated Akt (phosphoAkt) then phosphorylates a variety of substrates.

As described in the Examples, PI3K, which is activated by IGF1, was significantly diminished in expression after MD, but expression was fully restored after MD when IGF1 treatment was administered, suggesting that the plasticity-related effects of IGF1 may at least in part be mediated through PI3K. The present invention encompasses modulating the PI3K pathway, optionally by modulating the expression or activity of Akt, to modify plasticity in a subject in need thereof. For example, the invention encompasses administering an agent that inhibits or enhances phosphorylation of Akt. The invention contemplates modulating one or more components of the PI3K pathway, e.g., Akt, to promote recovery or reorganization of the nervous system in a subject in need thereof. Agents that modulate activity of PI3K and/or Akt are known in the art (see, e.g., U.S. Patent Publication 2003/0236271, which describes bicyclic or tricyclic fused heteroaryl derivatives useful to inhibit PI3K; and U.S. Patent Publication 2004/0176385, describing small molecule inhibitors of PI3K). In some embodiments, the agent is an RNAi agent, such as an siRNA that is targeted to a component of the PI3K signal transduction pathway (see, e.g., U.S. Patent Publication 2005/0272682).

In certain embodiments (described in more detail in the Examples), STAT1 is identified as being differentially regulated under a particular deprived condition (monocular deprivation), and the JAK/STAT pathway is identified as being a plasticity-related pathway. In particular, STAT1 is upregulated in the visual cortex of subjects that are subjected to MD. Furthermore, phosphorylated STAT1 was upregulated, indicating activation of the JAK-STAT cascade. The invention contemplates modulating one or more components of the JAK/STAT pathway in order to modify plasticity in a subject in need thereof. The invention also contemplates modulating one or more components of the JAK/STAT pathway to promote recovery or reorganization of the nervous system in a subject in need thereof. The JAK/STAT pathway is the major signaling mechanism for a diverse group of cytokines and growth factors (reviewed in Rawlings et al., 2004, *J Cell Sci.*, 117:1281). Binding of these ligands to their receptors induces multimerization of receptor subunits that are associated with Janus tyrosine kinases (JAKs), allowing transphosphorylation of the JAKs. Activated JAKs phosphorylate signal transducers and activators of transcription proteins (STATs), transcription factors that are present in the cytoplasm in latent form until activated. Phosphorylated STATs dimerize and are translocated into the nucleus, where they activate or repress transcription of target genes. In addition to these main components of the JAK/STAT pathway, other proteins that contribute to JAK/STAT signaling include signal-trans adapter molecules (STAMs), STAT-interacting protein (StIP), and the SH2B/Lnk/APS family. There are three main classes of negative regulators of JAK/STAT signaling: suppressor of cytokine signaling (SOCS) proteins, protein inhibitors of activated STATs (PIAS) proteins, and protein tyrosine phosphatases (PTPs).

The JAK/STAT pathway can be modulated using a variety of different methods. A component of the JAK/STAT pathway (e.g., a STAT or JAK polypeptide), or a ligand of a JAK-binding cytokine receptor can be administered. For example, a receptor agonist can be administered to activate the pathway, or an antagonist can be administered to inhibit the pathway. Other methods to modulate the JAK/STAT pathway include administering an agent that (i) disrupts or inhibits the physical association between a JAK and a STAT; (ii) activates or inhibits a kinase that phosphorylates one or more JAK substrates; (iii) activates or inhibits a phosphatase that dephosphorylates one or more JAK substrates; (iv) upregulates expression of a component of the JAK/STAT pathway; (v) downregulates expression of a component of the JAK/STAT pathway; (vi) disrupts the physical association between a JAK-binding cytokine receptor and a JAK; (vii) activates or inhibits a JAK-binding cytokine receptor; (viii) inhibits or enhances translocation of a STAT to the nucleus; (ix) inhibits association of a STAT with DNA; (x) disrupts the physical association between a JAK-binding cytokine receptor and an endogenous JAK regulating protein such as a SOCS or PIAS protein; (xi) induces or inhibits expression of an endogenous JAK regulating protein, etc. As noted above, RNAi agents are of use to inhibit expression of genes in the pathway, e.g., one or more JAK, STAT, SOCS, or PIAS proteins. In general, inhibiting expression of a JAK or STAT will inhibit the JAK/STAT pathway, while inhibiting expression of a negative regulator such as a SOCS or PIAS protein will activate the pathway.

The present invention encompasses the discovery that phosphorylated STAT1 is upregulated after MD. Without wishing to be bound by any theory, this upregulation may be a response of the brain to remove or reduce deprived eye connections as well as possibly expand non-deprived eye connections. Thus, upregulating STAT1 or otherwise activating the pathway in which it acts would enhance plasticity and/or increase the ocular dominance shift in a MD model.

In some embodiments, the agent that modulates the JAK/STAT pathway is a cytokine. Cytokines are polypeptides secreted by immune system cells (e.g., lymphocytes, macrophages, etc.) that exert a biological effect on other immune system cells and/or on other cells in the body. Examples include interferons, interleukins, chemokines, etc. The cytokine may upregulate a component of the JAK/STAT pathway such as STAT1. IFNγ is an exemplary cytokine of use in the invention to activate the JAK/STAT pathway. In some embodiments, the agent reduces STAT1 expression or activity. Exemplary agents that reduce STAT1 expression or activity include ionomycin and fludarabine. Without wishing to be bound by any theory, administration of these agents may alter the ocular dominance shift in an MD model. In some embodiments, the agent is a peroxisome proliferator receptor (PPAR)-gamma agonist. Examples include various prostaglandins such as 15-deoxy-delta 12,14-prostaglandin J(2), thiazolidinediones such as rosiglitazone, etc. In certain embodiments of the invention, one or more of these agents is administered to inhibit phosphorylation of one or more STAT or JAK proteins. In some embodiments, the agent is an HMG-CoA reductase inhibitor. HMG-CoA reductase inhibitors include statins such as simvastatin, atorvastatin, lovastatin, etc. These agents may be administered to inhibit the JAK/STAT pathway. Agents that inhibit STAT1 phosphorylation by inhibiting JAKs include tryphostins such as AG490 which blocks the action of JAK2 (Meydan et al., 1996, *Nature*, 379:645) and WHI-P131, which blocks the action of JAK3 (Sudbeck et al., 1999, *Clin. Cancer Res.*, 5:1569). Tyrphostins are low molecular weight compounds that specifically inhibit protein tyrosine kinases. See also U.S. Pat. No. 6,080,748, which describes a variety of dimethoxyquinazoline compounds useful as inhibitors of JAK3. See also U.S. Patent Publications 2003/0236244, 2004/0209799, 2004/0097504, 2005/0159385, and 2005/0148574.

The invention provides methods of modifying plasticity comprising steps of: modulating a cell type characterized in that one or more markers of the cell type is a product of a gene that is differentially regulated in at least a portion of the nervous system of an individual subjected to a condition that modifies plasticity. The invention provides methods of modifying plasticity comprising steps of: modulating a marker of a cell type characterized in that one or more markers of the cell type is a product of a gene that is differentially regulated in at least a portion of the nervous system of an individual subjected to a condition that modifies plasticity.

As noted above, the invention identifies the gene that encodes PV as being downregulated (i.e. underexpressed) in the visual cortex under conditions of DR, which prolong the state of plasticity associated with the critical period. The invention identifies PV expressing interneurons as being reduced in number in visual cortex under conditions of DR. Based at least in part on these discoveries, the invention provides methods of modifying plasticity in the nervous system of a subject comprising administering a plasticity-modifying agent to the subject, wherein the plasticity-modifying agent modulates development, survival, and/or activity of parvalbumin expressing interneurons in at least a portion of the brain. In some embodiments, the agent inhibits development, survival, and/or activity of parvalbumin expressing interneurons in at least a portion of the brain. In certain embodiments of the invention, the plasticity-modifying agent inhibits expression or activity of parvalbumin.

Exemplary methods of inhibiting development, survival, and/or activity of parvalbumin expressing interneurons include administering L-type calcium channel antagonists such as nimodipine or nifedipine (Jiang et al., 2005, *Neuroscience*, 135:839). In some embodiments, PV expressing interneurons are targeted for elimination by administering a complex comprising a cytotoxic agent and a targeting moiety, wherein the targeting moiety specifically binds to a marker of PV expressing interneurons, e.g., a molecule or portion thereof present at the cell surface of PV expressing interneurons. The complex or a portion thereof may be internalized. The cytotoxic agent selectively kills interneurons that have the marker present at their cell surface. "At the cell surface" is used herein to mean that a molecule or portion thereof is exposed to the extracellular environment and accessible to binding by a suitable binding agent.

The cytotoxic agent may be covalently or noncovalently associated with the targeting moiety. Alternatively or additionally, both the cytotoxic agent and the targeting moiety may be covalently or noncovalently associated with a third entity. For example, in some embodiments, the cytotoxic agent and the targeting moiety are covalently attached to one another either directly or via a linker moiety to form a conjugate. In some embodiments, the cytotoxic agent and the targeting moiety are associated with a delivery vehicle such as a polymeric scaffold, polymeric particle, or liposome. A variety of cytotoxic moieties can be used. Exemplary classes include alkalizing or alkylating agents, alkyl sulfonates, aziridines, ethylenimines and methylamelamines, nitrogen mustards, certain antibiotics, anti-metabolites, folic acid analogues, purine analogs, pyrimidine analogs, arabinosides, platinum analogs, microtubule inhibitors (e.g., microtubule depolymerizing agents or stabilizers), topoisomerase inhibitors, proteasome inhibitors, proapoptotic agents, kinase inhibitors, radioisotopes, toxins such as diphtheria toxin, *Pseudomonas* exotoxin A (PE), cholera toxin (CT), pertussis toxin (PT), ricin A chain, botulinum toxin A, conotoxins, etc. The marker may be, e.g., an ion channel or receptor subunit that is expressed by PV expressing interneurons. Typically, the marker is present at the cell surface of PV expressing interneurons at a higher average level than the level at which it is present at the cell surface of most or all other cell types in the nervous system. Examples include α subunits of L-type calcium channels (e.g., subunit 1.2 or 1.3; Jiang and Swann, 2005), NR2A subunits of NMDA receptors (Kinney, 2006), and the following ion channel subunits: HCN2, Kv3.1, Kv1.2, Kv1.6, Kv1.1, Kv3.2, HCN1, KVβ1, and Caα1A (Markram, 2004). The targeting moiety can be ligand of a receptor or channel that includes any of the foregoing subunits, an antibody or other specific binding agent (e.g., an aptamer or a binding peptide selected through phage display) that binds to a marker such as any of the foregoing subunits, etc.

Alternatively or additionally, in certain embodiments of the invention, it is desirable to reduce plasticity by accelerating or enhancing the development, survival, and/or activity of PV expressing interneurons. For example, agonists of L-type calcium channels such as BayK 8644 can be used.

In some embodiments, the present invention relates to administering combinations of multiple plasticity-modifying agents to a subject. The agents may be administered together in a single composition or separately. In some embodiments, an agent that modulates the IGF1 pathway and an agent that modulates the JAK/STAT pathway are administered. In some embodiments, an agent that modulates the IGF1 or JAK/STAT pathway and that inhibits development, survival, and/or activity PV expressing interneurons is administered. In some embodiments, an agent that modulates the IGF1 pathway, an agent that modulates the JAK/STAT pathway, and an agent that inhibits development, survival, and/or activity PV expressing interneurons are administered.

In some embodiments, the invention relates to compositions comprising multiple plasticity-modifying agents. One such composition comprises an agent that activates the IGF1 pathway and an agent that activates or inhibits the JAK/STAT pathway. The composition can comprise any agent that activates the IGF1 pathway and any agent that activates or inhibits the JAK/STAT pathway. In some embodiments, the composition comprises IGF1 or a biologically active variant or fragment thereof such as GPE, and an HMG-CoA reductase inhibitor such as a statin. In some embodiments, the composition comprises IFNγ or a biologically active fragment or variant thereof and an HMG-CoA reductase inhibitor.

Combined Administration of Plasticity-Modifying Agent and Proteolysis-Enhancing Agent In certain embodiments of the invention, one or more plasticity-modifying agents and one or more proteolysis-enhancing agents are administered to a subject. As described in co-pending patent application U.S. Ser. No. 11/205,501, entitled COMPOSITIONS AND METHODS FOR ENHANCING STRUCTURAL AND FUNCTIONAL NERVOUS SYSTEM REORGANIZATION, now published as U.S. Patent Publication 2006/0104969, the inventors have shown that focal administration of proteolysis-enhancing agents such as tPA, plasmin, or agents with plasmin-like activity to the nervous system of a subject promotes reorganization and recovery in the subject's nervous system. The invention provides methods for modifying plasticity in the nervous system of a subject comprising the step of: administering a plasticity-modifying agent and a proteolysis-enhancing agent to a subject in need thereof, wherein the agents are administered in an amount and for a time effective to modify nervous system plasticity, wherein the plasticity-modifying agent modulates a gene or pathway that is differentially regulated in at least a portion of the nervous system of an individual subjected to a plasticity-modifying condition. For example, in certain embodiments of the invention, the agent modulates a gene or pathway that is differentially regulated in at least a portion of the nervous system of an individual subjected to conditions of dark rearing (DR) or monocular deprivation (MD). The plasticity-modifying agent can be, e.g., any of the agents described herein.

Without wishing to be bound by any theory, proteolysis of one or more ECM component(s), mediated by a proteolysis-enhancing agent such as tPA and/or plasmin, creates an environment that is permissive for structural reorganization and may enhance activity of a plasticity-modifying agent. Thus, the present invention encompasses the recognition that enhancing proteolytic activity in the nervous system following nervous system damage in combination with administering a plasticity-modifying agent may permit increased structural remodeling relative to either therapy alone, thereby contributing to improved functional recovery. The following sections describe proteolysis-enhancing agents of use in the invention, drug delivery devices, methods and locations for the focal administration of plasticity-promoting agents and proteolysis-enhancing agents, and various other features of the invention.

A variety of different proteolysis-enhancing agents, or combinations thereof, are of use in the invention. In certain embodiments of the invention, the proteolysis-enhancing agent is a polypeptide. In certain embodiments of the invention, the polypeptide is a protease. In certain embodiments of the invention, the proteolysis-enhancing agent enhances proteolysis of fibrin. The agent may directly cleave fibrin or may activate an endogenous protease that cleaves fibrin. In certain embodiments of the invention, the agent enhances proteolysis of a component of the ECM other than fibrin in addition to, or instead of, enhancing proteolysis of fibrin. For example, the proteolysis-enhancing agent may cleave one or more extracellular matrix components including, but not limited to, collagen, laminin, fibronectin, and proteoglycans. It is noted that the classification of a particular agent as a plasticity-promoting agent or a proteolysis-enhancing agent should not be understood to be limiting in any way. Thus the effect(s) of the proteolysis-enhancing agent on the nervous system may result wholly or in part from one or more activities that does not involve proteolysis. While the plasticity-promoting agents of the present invention are not recognized as having proteolytic activity, such activity is not excluded, and the effect(s) of the plasticity-promoting agent on the nervous system may result wholly or in part from proteolysis that occurs as an indirect effect of their administration. For example, administration of the plasticity-promoting agent may increase expression of an endogenous proteolysis-enhancing agent such as plasmin or inhibit the expression of an endogenous inhibitor of a proteolysis-enhancing agent.

Suitable agents for use in the present invention include components of the tPA/plasmin cascade. Components of the tPA/plasmin cascade include plasminogen activators such as tissue plasminogen activator (tPA) and variants thereof, plasminogen, and plasmin. Plasminogen activators (PAs) are serine proteases that catalyze the conversion of plasminogen to plasmin (Vassalli, 1991) by cleavage of a single peptide bond (R561-V562) yielding two chains that remain connected by two disulfide bridges (Higgins and Bennett, 1990). Plasmin is a potent serine protease whose major substrate in vivo is fibrin, the proteinaceous component of blood clots. Plasminogen activation by tPA is stimulated in the presence of fibrin. Plasmin has a broad substrate range and is capable of either directly or indirectly cleaving many other proteins, including most proteins found in the ECM. "Direct," as used herein, means that the protease physically interacts with the polypeptide that is cleaved, while "indirect" means that the protease does not usually physically interact with the polypeptide that is cleaved, but tends to interact with another molecule, e.g., another protease, which in turn directly or indirectly cleaves the polypeptide. Plasmin is also capable of activating metalloprotease precursors. Metalloproteases in turn degrade ECM molecules. Metalloproteases are of use in certain embodiments of the present invention. In addition to the aforementioned substrates, plasmin cleaves and activates various growth factors and growth factor precursors. Although the liver is the major site of plasmin synthesis, plasminogen mRNA and protein have been detected in numerous brain regions. Thus, plasminogen is available to be cleaved by tPA administered to the nervous system.

Two PAs, tissue-type PA (tPA) and urokinase-type PA (uPA) have been identified in mammals. A major physiological function of PAs to trigger the lysis of clots by activating plasminogen to plasmin, which degrades fibrin. In the body, PA activity is regulated in part by various endogenous serine protease inhibitors that inhibit PAs, a number of which have been identified. Neuroserpin (Gene ID 5274) belongs to the serpin family of the serine protease inhibitors and is expressed by neurons of both the developing and the adult nervous system. Neuroserpin is present in regions of the brain where either tPA message or tPA protein are found, suggesting that neuroserpin may be the selective inhibitor of tPA in the CNS. Plasminogen activator inhibitor 1 (PAI-1; Gene ID 5054) is the main plasminogen activator inhibitor (PAI) in plasma but is also found in the nervous system. Protease-nexin I (Gene ID 5270), PAI-2 (Gene ID 5055), and PAI-3 (Gene ID 268591, *Mus musculus*) are other endogenous PAIs. Protease-nexin I and neuroserpin inhibit plasmin in addition to PAs.

While not wishing to be bound by any theory, there are a number of potential substrates for tPA and/or plasmin whose proteolysis may contribute to structural reorganization in the nervous system. Among these are various ECM proteins such as fibrin, fibronectin, tenascin, and laminin. In addition to plasmin, tPA may activate other proteases such as the plasmin-like protein hepatocyte growth factor (HGF), which may in turn cleave additional substrates.

tPA for use in the present invention may be from any species, although for administration to humans, it is generally desirable to use human tPA or a variant thereof. tPA and useful variants thereof, including variants with improved properties are described in U.S. Pat. Nos. 6,284,247; 6,261, 837; 5,869,314; 5,770,426; 5,753,486 5,728,566; 5,728,565; 5,714,372; 5,616,486; 5,612,029; 5,587,159; 5,520,913; 5,520,911; 5,411,871; 5,385,732; 5,262,170; 5,185,259; 5,108,901; 4,766,075; 4,853,330, and other patents assigned to Genentech, Inc. (see also Higgins 1990). For example, and without limitation, the tPA variant may have an alteration in the protease domain, relative to naturally occurring tPA, and/ or may have a deletion of one or more amino acids at the N-terminus, relative to naturally occurring tPA. The tPA variant may have one or more additional glycosylation sites relative to naturally occurring tPA and/or may have an alteration that disrupts glycosylation that would normally occur in naturally occurring tPA when expressed in eukaryotic cells, e.g., mammalian cells. Properties that may be of use include, but are not limited to, increased half-life, increased activity, increased affinity or specificity for fibrin, etc.

Human tPA has been assigned Gene ID 5327 in the Entrez Gene database (National Center for Biotechnology Information; NCBI) and the GenBank entry for the full length amino acid, mRNA, and gene sequences are AAA98809, K03021, and NM_000930, respectively. However, it is noted that it may be preferable to use the mature form of tPA, lacking the signal sequence peptide (as described, e.g., in U.S. Pat. No. 4,853,330 and Yelverton 1983) or a variant thereof.

The chymotrypsin family serine proteases, of which tPA is a member, are normally secreted as single chain proteins and are activated by a proteolytic cleavage at a specific site in the polypeptide chain to produce a two chain form (Renatus, 1997, and references therein). Both the single chain and two chain forms are active towards plasminogen, although the activity of the two-chain form is greater. Plasmin activates single-chain tPA to the two-chain form, thus resulting in a positive feedback loop. The single chain, the two chain form of tPA, and/or combinations thereof, may be used in the present invention.

tPA and variants thereof are commercially available and have been approved for administration to humans for a variety of conditions. For example alteplase (Activase®, Genentech, South San Francisco, Calif.) is recombinant human tPA. Reteplase (Retavase®, Rapilysin®; Boehringer Mannheim, Roche Centoror) is a recombinant non-glycosylated form of human tPA in which the molecule has been genetically engineered to contain 355 of the 527 amino acids of the original protein. Tenecteplase (TNKase®, Genentech) is a 527 amino acid glycoprotein derivative of human tPA that differs from naturally occurring human tPA by having three amino acid substitutions. These substitutions decrease plasma clearance, increase fibrin binding (and thereby increase fibrin specificity), and increase resistance to plasminogen activator inhibitor-1 (PAI-1). Anistreplase (Eminase®, SmithKline Beecham) is a commercially available human tPA.

Additional plasminogen activators include streptokinase (Streptase®, Kabikinase®) and urokinase (Abbokinase®), both of which are commercially available.

Alternatively or additionally, proteolysis-enhancing agents of use in the invention include tPA activators such as *Desmodus rotundus* salivary plasminogen activator (DSPA) Desmoteplase (Paion, Germany) which is derived from vampire bat saliva (Liberatore, 2003, and references therein). Four distinct proteases have been characterized and are referred to as *D. rotundus* salivary plasminogen activators (DSPAs). Full-length vampire bat plasminogen activator (DSPA1) is the variant most intensively studied and exhibits >72% amino acid sequence identity with human tPA. However, 2 important functional differences are apparent. First, DSPAs exist as single-chain molecules that are not cleaved into 2 chain forms. Second, the catalytic activity of the DSPAs appears to be dependent on a fibrin cofactor. Urokinase plasminogen activators such as rescupase (Saruplase®, Grunenthal), and microplasmin (a cleavage product of plasminogen) are also of use in various embodiments of the invention. Alfimeprase (Nuvelo) is yet another proteolysis-enhancing agent of use in the present invention. Alfimeprase is a recombinantly produced, truncated form of fibrolase, a known directly fibrinolytic zinc metalloproteinase that was first isolated from the venom of the southern copperhead snake (Agkistrodon contortrix contortrix) (Toombs, 2001). These enzymes breaks down fibrin directly. Fibrolase itself is of use in the present invention. Also of use is staphylokinase (Schlott, 1997).

In some embodiments of the invention plasmin or mini-plasmin is administered instead of, or in addition to, tPA. A variety of other agents that have plasmin-like activity may be used. In general, such substances are able to cleave typical plasmin substrates, such as the synthetic substrate S-225™ (Chromogenix-Instrumentation Laboratory, Milan, Italy), which is a conveniently assayed chromogenic substrate for plasmin and activated plasminogen. Other agents that have tPA-like activity (e.g., they are able to cleave plasminogen and activate it in a similar manner to tPA) can be used.

Lumbrokinase is an enzyme or group of enzymes derived from earthworms *Lumbricus rubellus* which has been known for some time (see, e.g., reporting cloning of a gene encoding lumbrokinase, PI239, GenBank Accession No. AF433650; Ge, 2005). Other fibrinolytic proteases isolated from earthworms are of use (Cho, 2004). Also of use is nattokinase.

In some embodiments, a variety of fibrinolytic enzymes that have been isolated from various worms, insects, and parasites can be used in accordance with the present invention. For example, destabilase, an enzyme present in the leech, hydrolyzes fibrin cross-links (Zavalova, 1996; Zavalova, 2002).

In some embodiments of the invention, plasminogen is administered instead of, or in addition to, tPA.

Instead of, or in addition to, administering a molecule that itself has plasminogen activator activity, plasmin activity, or plasmin-like activity, substances that increase endogenous expression of plasminogen activators or plasmin may be administered. Such substances may act by increasing transcription or translation of the mRNA that encodes the molecule, stabilizes the molecule, etc. They include, but are not limited to, brain derived neurotrophic factor (BDNF), transforming growth factor-$\beta$ (TGF-$\beta$), phorbol esters, and retinoic acid.

A variety of other agents can be administered to enhance protolysis in the central or peripheral nervous system in order to treat nervous system damage due to ischemic, hemorrhagic, neoplastic, traumatic, degenerative, and/or neurodevelopmental conditions. Certain of these agents are administered focally while others are administered using an alternate route of administration, e.g., oral, intravenous, intraperitoneal, intramuscular, intradermal, transdermal, subcutaneous, pulmonary (e.g., by inhalation into the lungs), nasal, etc. For example, sulodexide is a fibrinolytic agent that releases cellular tPA and thus is of use to increase tPA activity. In certain embodiments of the invention it is administered orally (Harenberg, 1998). Other agents of use in the invention to inhibit PAI include enalapril (Sakata, 1999) and ampotherin (Parkinnen, 1993).

Aspirin, which has been reported to stimulate plasmin activity, is of use in the invention (Milwidksy, 1991). In certain embodiments aspirin is not used, or if the subject is receiving aspirin, a different agent is used in addition to aspirin.

Another strategy that may be used to increase the level of plasminogen activator activity, plasmin activity, or plasmin-like activity is to administer a substance that inhibits one or more of the endogenous inhibitors of tPA or plasmin. Such endogenous inhibitors include PAI-1, PAI-2, PAI-3, and neuroserpin. A plasminogen activator inhibitor will be referred to as a PAI herein. In some embodiments, an inactive form of a PAI, which is unable to inhibit plasminogen activators, is used (see, e.g., PCT Publication WO 97/39028; and Lawrence et al., 1997, *J. Biol. Chem.*, 272:7676; both of which describe various inactive forms of PAI). Without wishing to be bound by any theory, an inactive form of PAI may compete with an active form and thereby prevent inhibition of tPA. Small molecules and peptides that inhibit one or more PAIs are known in the art and are of use in the present invention. Examples include PAI-039 (Hennan, 2005), ZK4044 (Liang, 2005), tiplaxtinin (Elokdah, 2004), piperazine-based derivatives (Ye, 2004), T-686 (Ohtani, 1996), fendosal (HP129), AR-H029953XX, XR1853, XR5118 and the peptide TVASS (Gils, 2002).

RNAi may be used to reduce expression of a transcript that encodes an inhibitory protein, e.g., an endogenous PAI. siRNAs or shRNAs targeted to a transcript that encodes an endogenous PAI can be delivered together with a proteolysis-enhancing agent or administered separately. Alternatively or additionally, a vector that provides a template for intracellular synthesis of one or more RNAs that hybridize to each other or self-hybridize to form an siRNA or shRNA that inhibits expression of an inhibitory protein, or cells that synthesize such RNAs, can be administered.

Antisense oligonucleotides complementary to an mRNA transcript that encodes an inhibitory protein, or ribozymes that cleave the transcript, or vector that provide template for intracellular synthesis of an antisense RNA or ribozyme can also be used to down-regulate expression of the inhibitor. In some embodiments of the invention, an aptamer that binds to a PAI and inhibits its inhibitory activity is used. In some embodiments, an RNA or DNA enzyme that cleaves a transcript that encodes a PAI and thus inhibits its inhibitory activity is used.

In certain embodiments, an antibody or antibody fragment that binds to a PAI is used to inhibit its activity, or any polypeptide having a similar binding specificity, e.g., an affibody. The antibody or antibody fragment can be any immunoglobulin or immunoglobulin-like molecule that binds to an antigen and can be monoclonal or polyclonal.

Any substance that acts to counteract the effect of a molecule that is inhibitory for activity of a proteolysis-enhancing agent, whether by causing degradation, by sequestering, by reducing expression, or by blocking interaction of the molecule with another molecule or with a cell will be said to counteract the inhibitory molecule and is within the scope and spirit of the invention.

The present invention encompasses the recognition that enhancing proteolytic activity in the nervous system following nervous system damage may permit increased structural remodeling, thereby contributing to improved functional recovery and will increase the efficacy of a plasticity-enhancing agent. However, the invention described herein does not require any particular mechanism of action. The invention encompasses use of variants or modified forms of the proteolysis-enhancing agents, wherein the variants or modified forms do not enhance proteolysis. For example, the invention encompasses variants of proteases (e.g., variants having a mutation in an active site region) in which the sequence has been altered, such that the variant is no longer an active proteolytic agent. The invention also encompasses embodiments in which the proteolysis-enhancing agent has been chemically inactivated, such that it no longer enhances proteolysis. Thus in some embodiments of the invention an inactive form of a proteolysis-enhancing agent is focally administered. However, in general, a proteolysis-enhancing agent is active or capable of being activated when used according to the present invention.

It will be appreciated that various agents have been focally administered to the nervous system of a subject suffering from ischemic, hemorrhagic, neoplastic, traumatic, toxic, neurodegenerative, and/or neurodevelopmental damage to the nervous system, for purposes other than enhancing proteolysis. For example, analgesic agents are commonly administered. Should it be the case that any of such previously administered agents enhance proteolysis, such agent may be explicitly excluded from the present invention or, if used in the present invention, its use in the context of the present invention differs from such previous use. For example, its use in the context of the present invention involves administration to a different location, uses a different administration means, involves administration in combination with a plasticity-modifying agent, and/or employs a different dose and/or time course, etc.

The ability of PAs to trigger the lysis of clots has led to the use of PAs and other plasminogen-activating proteases such as streptokinase as thrombolytic agents for the treatment of myocardial infarction and stroke, as mentioned above. However, studies have suggested that tPA, which is released by neurons following excitotoxicity such as occurs in ischemia, could increase neuronal damage. Furthermore, release or leakage of tPA out of the vascular system and the attendant potential for damage to nervous system tissue, is a recognized hazard of thrombolytic therapy. Thus the invention described herein, which demonstrates that appropriate administration of plasmin and/or plasminogen-activating proteases such as tPA can actually contribute to structural and/or functional nervous system reorganization and recovery, is particularly noteworthy.

It will be appreciated that various embodiments of the present invention differ from previously reported uses of tPA (e.g., for purposes of thrombolysis) in at least one of the following ways, which are described in further detail below: (i) administration as described herein is focally directed to the nervous system and does not typically take place via the vascular system; (ii) administration as described herein is typically performed at least 3 hours following the onset of a stroke or other damaging event and typically at least 12 hours or more following the onset of the damaging event; (iii) administration as described herein may occur multiple times (e.g., 2, 3, or more times) following the onset of a damaging event and/or may occur either intermittently or continuously over a prolonged time period following the onset of a damaging event (e.g., over at least 1 week, 4 weeks, 1 month (30 days), 3 months, 6 months, 1 year, 2 years, 3 years, or even longer); (iv) administration as described herein typically does not use doses that would be sufficient to cause effective blood clot lysis at the site of administration when administered using methods that are intended to achieve blood clot lysis.

Variants and Fragments

It will be appreciated that most proteins can tolerate a certain amount of sequence variation without substantial loss of functional activity, provided that such sequence variation does not affect key residues that are required for such functional activity. The present invention therefore encompasses variants of the plasticity-enhancing or proteolysis-enhancing polypeptides (and other polypeptides disclosed herein), wherein such variants retain a significant amount of biological activity. For example, the fragment can have substantially similar activity (e.g., at least about 10-20% of the relevant activity) to the original polypeptide, at least about 50% of the relevant activity, etc. The term "variants" includes fragments, i.e., polypeptides whose sequence is a continuous subset of a polypeptide disclosed herein. Biologically active variants or fragments of certain polypeptides of interest herein are known in the art. The invention contemplates the use of any such variant or fragment. For example, GPE is a biologically active fragment of IGF1 of use in the invention. Specifically encompassed are variants or fragments in which one or more kringle domains of a polypeptide disclosed herein, e.g. plasmin or tPA, is removed. Certain fragments of use in this invention contain a protease domain and, optionally, at least one kringle domain As is well known in the art, certain amino acids are generally similar with respect to particular properties and can frequently be substituted for one another in a polypeptide without significantly altering the functional and structural properties of the polypeptide. For example, the variants may contain one or more conservative amino acid substitutions, which may be defined in accordance with Stryer, *Biochemistry*, 3rd ed., 1988. Amino acids in the following groups possess similar features with respect to side chain properties such as charge, hydrophobicity, aromaticity, etc., and can be substituted for one another in accordance with certain embodiments of the invention: (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P (P may be considered to fall within group (1)). One of ordinary skill in the art will recognize that other definitions of conservative substitutions can also be used. Amino acid abbreviations used herein are in accordance with common usage in the art.

The present invention encompasses administration of variants that are at least 80% identical, at least 85% identical, at least 90% identical, at least 95% identical, or at least 98% identical to one or more of the polypeptides disclosed herein over a number of amino acids equal to at least 50% of the number of amino acids the polypeptide. Percent identity may be calculated by standard methods. For example, the percent identity between first and second polypeptides over a window of evaluation may be computed by aligning the polypeptides, determining the number of polypeptides within the window of evaluation that are opposite an identical polypeptides allowing the introduction of gaps to maximize identity, dividing by the total number of amino acid positions in the window, and multiplying by 100. Various computer programs such as BLAST2, BLASTP, Gapped BLAST, etc., generate alignments and provide % identity between sequences of interest. Algorithms employed in those programs (utilizing default values) can be used.

The present invention encompasses variants in which up to 20%, up to 15%, up to 10%, up to 5%, or up to 2% of the amino acid residues are either substituted (e.g., conservatively substituted), deleted, or added, relative to a polypeptide disclosed herein. Specifically encompassed are allelic variants that exist within a population. The invention encompasses variants that are specifically recognized by immunological reagents (e.g., monoclonal or polyclonal antibodies) that recognize a polypeptide disclosed herein, i.e., the immunological reagent binds to the variant with a substantially similar affinity (e.g., having a $K_a$ at least 50% as great) as that with which it binds to the polypeptide.

The invention encompasses variants that have a substantially similar overall structure to the polypeptides disclosed herein. For example, certain variants possess sufficient structural similarity to a protein disclosed herein so that when its 3-dimensional structure (either actual or predicted, structure) is superimposed on the structure of the protein the volume of overlap is at least 70%, at least 80%, or at least 90% of the total volume of the structure. Furthermore a partial or complete 3-dimensional structure of a variant may be determined by crystallizing the protein using methods known in the art.

Alternatively or additionally, an NMR solution structure can be generated (see, e.g., Heinemann, 2001; Wishart D. 2005; and references therein). A modeling program such as MODELLER (Sali and Blundell, 1993), or any other modelling program, can be used to generate a predicted structure. The PROSPECT-PSPP suite of programs can be used (Guo, 2004).

In certain embodiments of the invention, the variant has substantially similar plasticity-modifying or proteolysis-enhancing activity as the polypeptide of which it is a variant. In certain embodiments of the invention, the variant does not have a substitution at an active site residue. Active site residues of serine proteases such as the proteases disclosed herein are well known in the art.

Methods of Preparing the Agents of the Invention

The agents disclosed herein are all known in the art, and it is believed that appropriate methods for their manufacture are well within the skill of those in the art and therefore need not be described here in detail. For example, and without limitation, many of the small molecules described herein can be chemically synthesized using known methods, as can siRNAs and antisense oligonucleotides, and peptides. Certain agents can be purified from natural sources.

Plasticity-modifying agent such as IGF1, IFNγ, and proteolysis-enhancing agents, e.g., tPA, or other polypeptides such as plasmin, growth factors, etc., for use in the present invention, may be purified from natural sources, manufactured using recombinant DNA technology (e.g., recombinant tPA), synthesized using purely chemical synthesis (i.e., synthesis not requiring the use of cells to produce the polypeptide), etc.

Methods for producing a polypeptide of interest using recombinant DNA technology are well known in the art. Briefly, such methods generally involve inserting a coding sequence for the polypeptide into an expression vector, operatively associated with expression signals such as a promoter, such that mRNA encoding the protein is transcribed when the expression vector is introduced into a suitable host cell. The host cell translates the mRNA to produce the polypeptide. The polypeptide can include a secretion signal sequence so that the polypeptide is secreted into the medium. The polypeptide may be harvested from the cells or from the medium. Transgenic animals and plants are commonly used to produce polypeptides. Plants into which viral vectors have been introduced are also used to produce polypeptides.

Small molecules such as non-peptide neurotransmitters and analogs thereof, small peptides, neurally active metals, and other compounds disclosed herein are typically either purified from natural sources or chemically synthesized, as appropriate, according to standard methods.

Any of the agents disclosed herein can be provided as pharmaceutically acceptable salts, prodrugs, etc. Furthermore, any of the polypeptides disclosed herein can be modified using a variety of methods known in the art. For example, they can be modified by addition of polyethylene glycol (PEG) or variants thereof. Such modifications may increase the active half-life of the polypeptide (see, e.g., Nektar Advanced Pegylation 2005-2006 Product Catalog, Nektar Therapeutics, San Carlos, Calif., which describes a number of such modifying agents and provides details of appropriate conjugation procedures). For administration by injection or infusion, compositions of the invention will typically be mixed with pharmaceutically acceptable carriers or diluent such as sodium chloride (e.g., 0.9%) or dextrose (e.g., 5% dextrose) aqueous solutions. Agents can be provided for administration either in solution or in lyophilized or otherwise dried form. They can be reconstituted in water, saline, etc., followed by dilution in an appropriate pharmaceutically acceptable carrier or diluent.

Polymer-Based Drug Delivery Devices

The invention provides a drug delivery device for implantation into the nervous system of a subject to promote recovery or reorganization, e.g., following ischemic, hemorrhagic, neoplastic, traumatic, and/or neurodevelopmental damage to the nervous system. The drug delivery device comprises a release material, a plasticity-modifying agent, and, optionally, one or more additional active agents such as a proteolysis-enhancing agent. The term "release material" is used to refer to any matrix or material that releases incorporated molecules by diffusion or disintegration of the matrix. In certain embodiments of the invention the release material is a biocompatible polymer. The proteolysis-enhancing agent is released from the release material in an amount effective to promote reorganization and/or recovery of the nervous system. A drug delivery device in which an an active agent is physically associated with a polymeric material such as those disclosed herein is referred to as a "polymer-based drug delivery device" in order to distinguish such devices from mechanical drug delivery devices such as infusion pumps, which are used in various embodiments of this invention, though it should be recognized that materials other than polymers could also be used.

In certain embodiments of the invention, the plasticity-modifying agent and, optionally, the proteolysis-enhancing agent, is/are incorporated into or otherwise physically associated with a biocompatible polymeric matrix, which may be biodegradable or nonbiodegradable. Any form of physical association is acceptable provided that the association remains stable under conditions of storage and implantation and for sufficient time to release the active agent over a desired time period. For example, the active agent may be encapsulated within a polymeric matrix, entrapped or entangled within a polymeric matrix, adsorbed to the surface of a polymeric matrix, covalently attached to a polymeric matrix, etc. The matrix is delivered to or implanted into the body at the location of the target tissue or in the vicinity thereof. The agent is released from the polymeric matrix over a period of time, e.g. by diffusion out of the matrix or release into the extracellular environment as the matrix degrades or erodes. In some embodiments, the active agent is incorporated into liposomes.

The polymeric matrix may have a number of different shapes. For example, microparticles of various sizes (which may also be referred to as beads, microbeads, microspheres, nanoparticles, nanobeads, nanospheres, etc.) can be used. Polymeric microparticles and their use for drug delivery are well known in the art. Such particles are typically approximately spherical in shape but may have irregular shapes. Generally, a microparticle will have a diameter of less than 500 microns, more typically less than 100 microns, and a nanoparticle will have a diameter of 1 micron or less. If the shape of the particle is irregular, then the volume will typically correspond to that of microspheres or nanspheres. Methods for making microspheres are described in the literature, for example, in U.S. Pat. No. 4,272,398; Mathiowitz and Langer, 1987; Mathiowitz et al., 1987; Mathiowitz et al., 1988; Mathiowitz et al., 1990; Mathiowitz et al., 1992; and Benita et al., 1984. Solid nanoparticles or microparticles can be made using any method known in the art including, but not limited to, spray drying, nanoprecipitation, phase separation, single and double emulsion solvent evaporation, solvent extraction, and simple and complex coacervation. Preferred methods include spray drying and the double emulsion process. Solid agent-containing polymeric compositions can also be made using granulation, extrusion, and/or spheronization.

The conditions used in preparing the particles may be altered to yield particles of a desired size or property (e.g., hydrophobicity, hydrophilicity, external morphology, "stickiness," shape, etc.). The method of preparing the particle and the conditions (e.g., solvent, temperature, concentration, air flow rate, etc.) used may also depend on the agent being encapsulated and/or the composition of the polymer matrix. If the particles prepared by any of the above methods have a size range outside of the desired range, the particles can be sized, for example, using a sieve.

Solid nanoparticles or microparticles can be suspended or dispersed in a pharmaceutically acceptable fluid such as physiological saline and focally administered by injection or infusion (e.g., using a pump) to the nervous system.

Solid polymer-agent compositions (e.g., discs, wafers, tubes, sheets, rods, etc.) can be prepared using any of a variety of methods that are well known in the art. For example, in the case of polymers that have a melting point below the temperature at which the agent is to be delivered and/or at which the polymer degrades or becomes undesirably reactive, a polymer can be melted, mixed with the agent to be delivered, and then solidified by cooling. A solid article can be prepared by solvent casting, in which the polymer is dissolved in a solvent, and the agent is dissolved or dispersed in the polymer solution. Following evaporation of the solvent, the substance is left in the polymeric matrix. This approach generally requires that the polymer is soluble in organic solvent(s) and that the agent is soluble or dispersible in the solvent. In still other methods, a powder of the polymer is mixed with the agent and then compressed to form an implant. Microparticles or nanoparticles comprising a polymeric matrix and a proteolysis-enhancing agent and optionally one or more other active agents can be compressed, optionally with the use of binders, to form an implant.

A polymeric matrix can be formed into various shapes such as wafers, tubes, discs, rods, sheets, etc., which may have a range of different sizes and volumes. For example, prior to polymerization, a polymer solution may be poured into a mold having the appropriate shape and dimension. Following polymerization the material assumes the shape of the mold and is usable as an implant. The agent(s) may be present in the solution prior to polymerization, or the implant may be impregnated with the agent following its fabrication.

Suitable biocompatible polymers, a number of which are biodegradable include, for example, poly(lactides), poly(glycolides), poly(lactide-co-glycolides), poly(lactic acids), poly(glycolic acids), poly(lactic acid-co-glycolic acids), polycaprolactone, polycarbonates, polyesteramides, polyanhydrides, poly(amides), poly(amino acids), polyethylene glycol and derivatives thereof, polyorthoesters, polyacetals, polycyanoacrylates, polyetheresters, poly(dioxanones), poly(alkylene alkylates), copolymers of polyethylene glycol and polyorthoesters, biodegradable polyurethanes. Other polymers include poly(ethers) such as poly(ethylene oxide), poly(ethylene glycol), and poly(tetramethylene oxide); vinyl polymers-poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; poly(siloxanes); etc. Other polymeric materials include those based on naturally occurring materials such as polysaccharides (e.g., alginate), chitosan, agarose, hyaluronic acid, gelatin, collagen, and/or other proteins, and mixtures and/or modified forms thereof. Chemical derivatives of any of the polymers disclosed herein (e.g., substitutions, additions of chemical groups, for example, alkyl, alkylene, hydroxylations, oxidations, and other modifications routinely made by those skilled in the art) are encompassed. Furthermore, blends, graft polymers, and copolymers, including block copolymers of any of these polymers can be used. It will be appreciated that a vast number of different polymer variations are available. It will be understood that certain of these polymers require use of appropriate initiators or cross-linking agents in order to polymerize.

One of skill in the art will understand that in choosing an appropriate polymer and method of manufacture, it is important to select materials and methods that are compatible with stability of the agent. For example, it may be desirable to avoid processing temperatures that are likely to result in substantial degradation or denaturation of the agent, which may result in loss of bioactivity. It will also be desirable to test the composition so as to ensure that the agent is released in significant amounts over the desired period of time.

In general, the following criteria are important for selection of a material to be used for delivery of the active agent(s): (1) minimal or no cytotoxicity, (2) minimal or no elicitation of immune responses and inflammation, (3) compatibility with aqueous solutions and physiological conditions, and (4) compatibility of the material and its processing methods with the stability of the agent to be incorporated. It may be desirable to utilize a material with a controlled rate of biodegradation. Features such as cross-linking and monomer concentration may be selected to provide a desired rate of degradation and release of the agent. It will be appreciated that a polymeric drug delivery device of the invention may include one or more pharmaceutically acceptable materials such as buffers, spheronizing agents, fillers, surfactants, disintegrants, binders, or coatings. Exemplary materials are described in U.S. Pat. No. 5,846,565.

Methods for purifying or synthesizing the various polymers for use in drug delivery systems of the invention are known in the art. Methods for incorporating therapeutically active agents into polymeric matrices are likewise known in the art. For example, the active agent can be combined in solution with the polymer prior to polymerization or can be provided in solid form and encapsulated as the polymer polymerizes. A number of different agents have been delivered to the CNS using such polymer matrices. For example, chemotherapeutic agents have been delivered to tumors in the nervous system by encapsulating the agent in a polymeric matrix, which is made into a shaped form, and surgically implanting the matrix into the brain (see, e.g., U.S. Pat. Nos. 5,626,862; 5,651,986; and 5,846,565). Additional drug delivery devices in which an active agents is provided in a polymeric matrix are described (see, e.g., U.S. Pat. Nos. 4,346,709 and 5,330,768; Wu, 1994; Dang, 1996; Fleming, 2002; and Westphal, 2002).

Similar methods to those used in the afore-mentioned references are of use to focally deliver the agents of the invention. In certain embodiments of the invention, the drug delivery device provides controlled or sustained release, i.e., the proteolysis-enhancing agent and any other agents contained in the device are released over a prolonged period of time, e.g., hours to days, weeks, or months.

Preparation of polymer-agent drug delivery devices can be performed using standard methods known in the art. Briefly, drug delivery devices are typically prepared in one of several ways. For example, the polymer can be melted, mixed with the substance to be delivered, and then solidified by cooling.

Such melt fabrication processes generally utilize polymers having a melting point that is below the temperature at which the substance to be delivered and the polymer itself degrade or become reactive. Alternatively or additionally, the device can be prepared by solvent casting, where the polymer is dissolved in a solvent, and the substance to be delivered dissolved or dispersed in the polymer solution. The solvent is then evaporated, leaving the substance in the polymeric matrix. Solvent casting typically utilizes a polymer that is soluble in organic solvents, and the drug to be encapsulated should be soluble or dispersible in the solvent. Similar devices can be made by phase separation or emulsification or even spray drying techniques. In still other methods, a powder of the polymer is mixed with the agent and then compressed to form an implant.

Methods of producing implants also include granulation, extrusion, and spheronization. A dry powder blend is produced including the desired excipients and microspheres. The dry powder is granulated with water or other non-solvents for microspheres such as oils and passed through an extruder forming "strings" or "fibers" of wet massed material as it passes through the extruder screen. The extrudate strings are placed in a spheronizer which forms spherical particles by breakage of the strings and repeated contact between the particles, the spheronizer walls and the rotating spheroniter base plate. The implants are dried and screened to remove aggregates and fines.

These methods can be used to make microimplants (microparticles, microspheres, and microcapsules encapsulating drug to be released), slabs or sheets, films, tubes, and other structures. A preferred form for infusion or injection is microimplants, as described elsewhere herein.

Proteins and peptides have been successfully incorporated into polymeric matrices. For example, insulin has been incorporated into biodegradable polymeric microcapsules and retains essentially the same bioactivity as the free form (Takenaga 2004). Natural and synthetic collagenous matrices have been used as carriers of a variety of different growth factors (Kanematsu, 2004).

Of particular interest in the present invention are polymers that form hydrogels, i.e., gels that contain a substantial proportion of water. Hydrogels may, for example contain 30%, 40%, 50%, 60%, 70%, 80%, 90%, or an even greater amount of water on a w/w basis. Polymeric materials can be formed into hydrogels either prior to or following administration to a subject. An exemplary material comprises hPLA-b-PEG-PLA macromers. The agent is mixed with the polymer solution prior to initiating polymerization. Other suitable hydrogel-forming polymers are known in the art. For example, a variety of polysaccharides, polypeptides, and derivatives thereof can be used. Exemplary polysaccharides include alginate, collagen, cellulose, hyaluronic acid, dextran, chitosan, derivatives of any of the foregoing, etc. Other materials that form hydrogels include synthetic polymers such as polyethylene oxide-polypropylene glycol block copolymers such as Pluronics™ or Tetronics™, poly(vinyl alcohol), silicones, polypeptides such as gelatin, polyethylene glycol and related molecules, polyethylene oxide and related molecules or derivatives, etc. The hydrogel precursor materials may contain or be modified to contain functional groups that become crosslinked to one another. Optionally, photopolymerization is employed. In some embodiments, a drug delivery device comprising biodegradable macromers such as those described in U.S. Pat. No. 6,153,211 is used.

In some embodiments of the invention, a plasticity-modifying agent, a proteolysis-enhancing agent, or both, is covalently attached to the polymer, optionally via a moiety that is cleavable in vivo, such as an ester linkage or disulfide bond.

The polymer-based drug delivery devices of the invention may be implanted at any desired location within the CNS. For example, and without limitation, the polymer-based drug delivery device can be implanted either in the brain (e.g., close to a site of damage such as an ischemic region following stroke, or in the opposite brain hemisphere), or in the base of the brain, in or near a CSF-filled space such as ventricle, etc. In the case of a device implanted into a CSF-filled space, the device releases the agent into the CSF, allowing it to diffuse to a region of the brain surround the space. Depending on the size of the device, it can also be implanted at or adjacent to a nerve, nerve tract, ganglion, etc., of the PNS. For example, microimplants can be implanted within or internal to the epineurium or perineurium of a nerve.

Implantable Microchip-Based Delivery

In certain embodiments of the invention, one or more agent(s) is delivered to the nervous system using an external or implantable silicon or polymeric microchip, which contains from dozens to up to hundreds or thousands of microreservoirs, each of which can be filled with any combination of drugs, reagents, or other chemicals. Micro-reservoirs can be opened at predetermined times and/or on demand using pre-programmed microprocessors, remote control, or biosensors. If desired, complex chemical release patterns can be achieved using these approaches. In some embodiments, micro-reservoirs have "caps" that degrade over time. Release can be controlled by varying the thickness and/or composition of the cap, thereby allowing release to occur at predictable and substantially predetermined times. The cap material can be, e.g., a degradable polymer. In some embodiments, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays release. If diffusion through the cap material is limiting, the cap material determines the release rate of the molecules in addition to delaying release time.

In some embodiments, the agent(s) to be delivered are inserted into the reservoirs in their pure form, as a liquid solution or gel, or they may be encapsulated within or by a release material. The release material may be, for example, a biodegradable or non-biodegradable polymer. Representative polymers include those mentioned above (see, e.g., Santini et al., 2000; U.S. Pat. Nos. 5,797,898 and 6,808,522; and U.S. Patent Publications 2002/0072784, 2004/0166140, and 2005/0149000; for discussion of microchip-based delivery systems). Microchips can be implanted at any desired location in the CNS (as described above). Depending on the size of the device, it can also be implanted at or adjacent to a nerve, nerve tract, ganglion, etc., of the PNS. For example, microchips can be implanted within or internal to the epineurium or perineurium of a nerve.

Methods for Focal Delivery

In certain embodiments of the invention, compositions comprising a plasticity-modifying agent and optionally a proteolysis enhancing agent are administered to a subject by focal delivery. Focal delivery may be accomplished in a number of different ways. Implantation of a polymer-based drug delivery device or microchip such as those described above at a site within the central nervous system or within or adjacent to a nerve, nerve tract, or ganglion within the peripheral nervous system is a suitable method to achieve focal delivery.

Internal (implantable) or external pumps can be employed for administering a substantially fluid composition of the invention. Such pumps typically include a drug reservoir from which continuous or intermittent release occurs into the target tissue or in the vicinity thereof via a catheter. In certain embodiments of the invention, treatment is carried out using an implantable pump and a catheter having a proximal end coupled to the pump and having a discharge portion for infusing therapeutic dosages of one or more agents described herein into a predetermined infusion site in brain tissue or into the spinal canal (intrathecal delivery).

Infusion (which term is used to refer to administration of a substantially fluid material to a location in the body by means other than injection) may be carried out in a continuous or nearly continuous manner, or may be intermittent. The pump may be programmed to release predetermined amounts of the agent at predetermined time intervals. U.S. Pat. No. 4,692,147 (assigned to Medtronic, Inc., Minneapolis, Minn.) describes a suitable pump. In certain embodiments one or more of the infusion systems known as the Synchromed® Infusion System (manufactured by Medtronic, Inc., Minneapolis, Minn.; see web site having URL www.medtronic.com) is used. However, it will be appreciated that the pump may take the form of any device used for moving fluid from a reservoir. Mechanical, pressure-based, osmotic, or electrokinetic means may be used.

In order to deliver an agent to the brain parenchyma, a catheter attached to the pump may be implanted so that the discharge portion lies in the brain parenchyma (see, e.g., U.S. Pat. No. 6,263,237 for description of a variety of suitable systems and methods for implanting them into the body of a subject and directing the administration of an active agent to a desired location in the brain). Continuous ICM is a relatively new technique of regional delivery of therapeutic agents directly into brain parenchyma, which establishes a bulk flow current that has the potential to homogeneously distribute even large molecules (see, e.g., Laske, 1997 for an example of administration of an agent to a region within the brain).

In certain embodiments of the invention, the agent is delivered to one or more of the CSF-containing cavities or chambers of the central nervous system, e.g., the ventricles or cisterna magna, which is located at the bottom of the skull. As is well known in the art, there are two lateral ventricles and midline third and fourth ventricles within the brain. To deliver an agent to a ventricle or the cisterna magna using an infusion pump, the catheter may be implanted so that the discharge portion lies in the ventricle or the cisterna. The agent diffuses out of the ventricle or cisterna magna. Delivery to these locations therefore allows delivery of the agent to a relatively wide area of the brain rather than localizing it more closely to a specific site. Intraventricular or intracisternal administration is considered to be administration to the nervous system. In certain embodiments of the invention delivery to a CSF-containing space, e.g., a ventricle, is accomplished by surgically implanting a catheter through the skull so that the tip has access to the space. The other end of the catheter is then connected to a reservoir (e.g., an Ommaya reservoir), which is placed beneath the scalp (i.e., subcutaneously). This method is in use for delivery of chemotherapeutic agents (see, e.g., Ommaya and Punjab, 1963; Galicich and Guido, 1974; Machado, 1985; Obbens, 1985; and Al-Anazi, 2000).

If the subject suffers from damage to the spinal cord, the catheter is implanted so that the discharge portion lies in an intrathecal space of the spinal cord while the other end is connected to the pump reservoir. Methods for administering agents to the spinal fluid (i.e., intrathecally) are well known in the art. Such methods are commonly used in the treatment of chronic pain, and are routinely used to deliver analgesic agents over a period of months. Similar methods are of use in the present invention (see, e.g., Lamer, 1994; Paice, 1996; Winkemuller, 1996; Tutak, 1996; and Roberts, 2001 for descriptions of the use of implantable pumps for delivery of a variety of different therapeutic agents for treatment of a number of different conditions).

For delivery to the PNS, suitable methods include injection or infiltration into a nerve or nerve trunk, e.g., adjacent to a site of nerve damage, and implantation of a polymer-based delivery device or microchip either adjacent to a site of nerve damage. Methods for administering anesthetic agents to diverse nerves, nerve bundles, etc., within the PNS are well known in the art, and any of these methods are applicable in the context of the present invention.

In certain embodiments of the invention, a solution comprising a polymer, a plasticity-modifying agent, and optionally one or more additional active agents is administered by injection or infusion using any of the means described above. The polymer assembles to form a gel upon administration, e.g., following contact with physiological fluids. Such assembly may, for example, be triggered by exposure to monovalent or divalent cations. For example, U.S. Publication 2002/0160471 describes self-assembling peptides that form hydrogels. U.S. Pat. No. 6,129,761 describes a variety of different self-assembling polymers and polymers that require a polymerizing agent or cross-linking agent to facilitate assembly. Certain of these polymers assemble to form hydrogel structures upon contact with physiological fluids following administration to a subject. In another embodiment a collagen-based system is used (see, e.g., PCT Publication WO 00/47130, which describes injectable collagen-based systems for delivery of cells or therapeutic agents).

Delivery Location, Timing, Duration of Treatment, and Dose

The plasticity-modifying agent(s) can be administered using any route of administration, e.g., oral, intravenous, intraperitoneal, intramuscular, intradermal, transdermal, subcutaneous, pulmonary (e.g., by inhalation into the lungs), nasal, etc. The route and dose will be selected so as to achieve effective concentrations in the nervous system without undue side effects.

The location at which a composition of the invention is to be administered or implanted may be selected with relation to the particular condition being treated. For example, if the subject has suffered an injury or damage to the brain, e.g., as a result of stroke, trauma, etc., the composition may be delivered to the brain parenchyma or to one or more of the ventricles of the brain or to the cisterna magna. If the subject has suffered an injury or damage to the spinal cord, a composition of the invention may be delivered to the spinal cord, e.g., by implanting or administering a composition within the spinal canal. If the plasticity-modifying agent or an inventive composition crosses the blood-brain barrier, it can be delivered systemically, e.g., by oral, intravenous, intraperitoneal, intramuscular, intradermal, transdermal, subcutaneous, pulmonary (e.g., by inhalation into the lungs), nasal, etc. administration.

The area to which the agent is to be administered may be, for example, an area that has been damaged (e.g., an ischemic lesion) or an area adjacent to an area that has been damaged. The agent(s) may be administered to any region, nucleus, or functional area within the brain including, but not limited to, any of the major subdivisions of the brain (cortex, hippocampus, cerebellum, thalamus, midbrain, brain stem), which include motor cortex, sensory cortex including visual cortex, auditory cortex, and somatosensory cortex, language areas of cortex, frontal cortex, internal capsule, basal ganglia, thalamus, and/or other area noted above, etc. As noted above, numerous specific areas within the brain have been defined based on anatomical and histological considerations. In addition, areas in the brain that are responsible for performing various tasks have been defined on functional grounds and are well known in the art (see, e.g., Kandel, supra; and Victor and Ropper, supra).

In certain embodiments of the invention, the area that has been damaged is identified. The area that has been damaged can be identified using a variety of different imaging techniques known in the art. For example, and without limitation, suitable methods include imaging techniques such as magnetic resonance imaging (MRI), optionally imaging features associated with blood flow such as perfusion, diffusion, or both, computed tomography (CT), positron emission tomography (PET), ultrasound, etc. Imaging techniques that image structure and/or function are available. Functional studies can be performed, e.g., using labeled substrates such as glucose to identify regions of the brain that are metabolically inactive and/or that do not respond to stimulation, suggesting that they are functionally inactive (see, e.g., Grossman and Yousem, supra).

Clinical diagnosis can be used instead of, or in addition to, imaging techniques. For example, the area to which damage has occurred can be identified by performing a neurological examination. Deficits noted on the neurological examination can be correlated with damage to particular areas of the central and/or peripheral nervous system (Kandel, supra; and Victor and Ropper, supra). In certain conditions, such as neuropsychiatric disorders of developmental or adult origin, a genetic test may be used in addition to a clinical diagnosis.

Any of the foregoing methods can be utilized acutely (e.g., within hours to a few days of a damaging event such as stroke or injury) or at later times (e.g., several days to weeks, months, or years following the event). The characteristic evolution of the appearance of nervous system lesions is well known in the art, so the practitioner can readily identify the location of damaged tissue at any desired time point relative to the time at which the event causing the damage occurred.

In certain embodiments of the invention, the agent is delivered at or adjacent to a site where tissue necrosis and/or scar tissue formation has occurred in the CNS. Areas of necrosis can be identified using various imaging techniques such as those mentioned above. Symptoms may also be used to guide selection of an appropriate location at which to implant the matrix. For example, if a subject experiences impairment of a particular function such as movement, sensation, speech, etc., then the portion of the brain that is normally responsible for control or achievement of that function, or the corresponding area on the contralateral side of the subject's body, may be selected as a suitable site for implantation of a drug delivery device of the invention. Standard surgical techniques can be used.

In some embodiments of the invention the agent is administered to an area adjacent to a region that has been damaged by an infarct, e.g., to the peri-infarct area. Without wishing to be bound by any theory, peri-infarct regions are likely to be sites of clinically relevant cortical remodeling following stroke. For example, the agent may be administered to a site that is located up to approximately 0.5 cm from the edge of an infarcted area, up to 1.0 cm from the edge of an infarcted area, or up to 2 cm from the edge of an infarcted area. In some embodiments the agent is administered to a site immediately adjacent to an infarcted area, e.g., up to 0.5 cm from the edge of the infarcted area. In some embodiments of the invention the agent is administered to the ischemic penumbra adjacent to an area of severe ischemia following stroke (see, e.g., Furlan et al., 1996). The ischemic penumbra is a region of brain tissue that experiences mild to moderate ischemia but remains viable for a period of time following a stroke (e.g., up to several hours or longer) and may be salvageable if perfusion is re-established and/or through the use of neuroprotective agents. The ischemic penumbra may be operationally defined using, e.g., diffusion and perfusion MRI (Schlaug et al., 1999; and Kidwell et al. 2003). One of ordinary skill in the art will be able to select an appropriate definition and measurement technique.

In some embodiments of the invention, the agent is administered to a location on the opposite side of the brain from the side where damage has occurred. The site of administration may be substantially symmetrically located with respect to the region that has been damaged. Without wishing to be bound by any theory, it is possible that following damage to a particular region of the brain, the contralaterally located region reorganizes so as to assume responsibility for functions that were previously performed by the damaged region. For example, a portion of the brain that normally (e.g. prior to injury) generates movement commands for the left hand only may reorganize so as to generate commands to both hands following damage to a portion of the brain that previously commanded the right hand.

As mentioned above, delivery by injection or infusion pump is suitable for compositions in which an agent of the invention is dissolved in a liquid and for compositions comprising microparticles of suitable dimensions. The polymer-based drug delivery devices of the invention will typically be implanted into the subject in an appropriate location in the nervous system so that they will release the active agent at a desired location. For example, they may be implanted into the brain parenchyma. They may also be implanted into a ventricle or into the spinal canal in various embodiments of the invention. The location for implantation is selected so as to achieve an effective concentration of the active agent at a desired location in the nervous system, i.e., typically reasonably close to the location at which it is desired to achieve the effective concentration. Care is taken to avoid disrupting undamaged portions of the nervous system to the extent possible. Imaging may be used to guide administration or implantation of the compositions and drug delivery devices of the invention, e.g., they may be administered or implanted under stereotactic guidance.

The agent(s) can be administered in a continuous or intermittent fashion. Intermittent or pulsatile delivery may be performed at times selected in accordance with the active half-life of the agent in order to maintain a therapeutically useful dose and/or may be performed in accordance with physiological patterns such as circadian rhythms, or during periods when the subject either is or is not engaged in particular activities. If the agent is administered using an implanted device such as a pump or microchip, an external controller may be used to trigger release at a desired time, or the device can be programmed to release the agent at particular times or intervals.

In some embodiments, compositions of the invention may be administered to a subject following an event that damages the brain or spinal cord or following diagnosis of a neuropsychiatric or neurodevelopmental disorder for a finite period of time. For example, compositions of the invention may be administered to a subject for up to 1 week, up to 4 weeks, up to 2 months, up to 6 months, up to 12 months, up to 18 months, up to 2 years, up to 5 years, up to 10 years, up to 20 years, or even longer. In some embodiments, compositions of the invention may be administered to a subject following an event that damages the brain or spinal cord or following diagnosis of a neuropsychiatric or neurodevelopmental disorder for the rest of the subject's life.

In some embodiments, compositions of the invention are not administered immediately after an event that damages the brain or spinal cord or following diagnosis of a neuropsychiatric or neurodevelopmental disorder. To give but a few examples, administration may be initiated after certain other therapeutic strategies (e.g. behavioral therapies) have been performed; after the subject has reached a desired level of health; after the subject has reached a desired age; etc. In some embodiments, compositions of the invention are administered at least 1 week, at least 4 weeks, at least 2 months, at least 6 months, at least 12 months, at least 18 months, at least 2 years, at least 5 years, at least 10 years, at least 20 years, or even longer, after an event that damages the brain or spinal cord or following diagnosis of a neuropsychiatric or neurodevelopmental disorder.

In some embodiments, compositions of the invention may be administered for a period of time and may then be discontinued. For example, administration may be discontinued when the subject responds to the administration (e.g. if symptoms improve, if damage is reversed, if plasticity has been modified, if function has been restored to the nervous system, if neural development has been stimulated, etc.). To give another example, administration may be discontinued when the subject has reached at least one desired endpoint or treatment milestone. In some embodiments, compositions of the invention may be administered to a subject for up to 1 week, up to 4 weeks, up to 2 months, up to 6 months, up to 12 months, up to 18 months, up to 2 years, up to 5 years, up to 10 years, up to 20 years, or even longer, before being discontinued. In some embodiments, administration of compositions of the invention that has been discontinued may be resumed at any point in time after discontinuing the administration. To give but one hypothetical example, (i) a plasticity-modifying agent may be administered to a subject following diagnosis with a neurodevelopmental disorder; (ii) the subject's symptoms may disappear; (iii) administration of the plasticity-modifying agent may be discontinued; (iv) the symptoms may return; and (v) administration of the plasticity-modifying agent may be resumed. In some embodiments, administration may be discontinued for up to 4 weeks, up to 2 months, up to 6 months, up to 12 months, up to 18 months, up to 2 years, up to 5 years, up to 10 years, up to 20 years, or even longer, before administration is resumed.

In certain embodiments of the invention, the compositions of the invention are administered at times varying from immediately after to considerably after, e.g., least 3 hours after, the onset or occurrence of a damaging event such as a stroke or injury. For example, the initial administration may be a few minutes to hours, e.g., at least 6, 12, 24, 36, or 48 hours after the onset or occurrence of a damaging event. In certain embodiments of the invention the initial administration is between 24 hours and 1 week after the onset or occurrence of a damaging event, between 1 week and 1 month after the onset or occurrence of a damaging event, or between 1 and 3 months, 3 and 6 months, 6 and 12 months after the onset or occurrence of a damaging event, etc. The initial administration may occur at times greater than 1 year following the onset or occurrence of a specific damaging event, e.g., between 1-5 years, etc. In some embodiments of the invention the initial administration occurs after the subject has reached a plateau of functional recovery. For example, the subject may have failed to display improvement on one or more standardized tests, or may have failed to experience subjective improvement during the preceding 1-3 months, 3-6 months, or longer.

For treatment of neuropsychiatric disorders, neurodegenerative diseases, nutrient deprivation, neoplastic diseases, and other conditions for which there is no specific identifiable damaging event, administration can occur at any time following diagnosis of the disease.

The total time period during which treatment occurs, and the number of treatments within such time period, can vary. The total duration of treatment (i.e., the time interval between the first and the last treatment) can range from days to weeks, months, or years. For example, the total duration may be 1 day; 1 week; 4 weeks; 1, 3, 6, 9, or 12 months, between 1 and 2 years; 2 and 5 years; 2 and 10 years; 2 and 20 years; etc. If the agent is administered in discrete doses in addition to or instead of being administered continuously, subjects may receive anywhere from a single dose to dozens or even hundreds or thousands of doses. The time interval between doses can be varied. It may, for example, be desirable to administer the agent for a defined time period each day, e.g., 10 minutes/day, 1 hr/day, etc.

The dose of the plasticity-modifying agent will be selected taking into account the particular agent, the condition being treated, the route of administration, and other relevant factors. The dose (or doses) may be, e.g., an amount effective to promote growth or sprouting of axons, promote structural reorganization of synaptic connections, increase formation of new synaptic connections, increase dendritic spine motility, inhibit structural or functional degeneration (e.g., degeneration that would otherwise be expected to take place) or any combination of the foregoing. The dose may range from about 0.001 to 100 mg/kg body weight, e.g. from about 0.01 to 25 mg/kg body weight. The dose may, for example, range between 1 µg/kg and 100 mg/kg, e.g., between 10 µg/kg and 10 mg/kg. Exemplary doses range from 0.1 to 20 mg/kg body weight, e.g., about 1 to 10 mg/kg.

The dose of the proteolysis-enhancing agent will be selected to enhance the effect of the plasticity-modifying agent. Typically the dose for each administration of the proteolysis-enhancing agent will be significantly lower than the dose that would be required to cause lysis of a significant blood clot when administered to the vascular system. Exemplary, non-limiting doses ranges for a proteolysis-enhancing agent, e.g., tPA, include one or more of the following: (i) a dose sufficient to achieve a concentration of between 10 and 100,000 IU/ml or between 100 and 10,000 IU/ml or between 100 and 1,000 IU/ml in the extracellular fluid or in a CSF-containing cavity such as a ventricle or the spinal canal; a dose between 1 µg/day and 10 mg/day; a dose between 1 µg/day and 1 mg/day; a dose 5 µg/day and 500 µg/day; a dose between 10 µg/day and 100 µg/day, etc.

Various dosing regimens may be used. For example, it may be desirable to give a relatively large "loading dose" initially and then administer smaller doses either continuously or intermittently so as to maintain an effective concentration in the region of the nervous system being treated. It will also be appreciated that, in general, the more focally directed the delivery, the lesser the total dose that may be required. Thus direct administration via a catheter to a specific brain region may require a lower total dose than delivery to a ventricle. Furthermore, the larger the area of damage and/or the greater the amount of reorganization and/or recovery required, the larger might be the dose.

If desired, the concentration of the plasticity-modifying agent (or any other agent whose administration is contemplated in the present invention) can be monitored, e.g., in the CSF of the subject. The dose can be adjusted accordingly to obtain a desired concentration.

In certain embodiments of the invention the agent(s) is/are administered, e.g., released, in a defined temporal relation to rehabilitative therapy, e.g., during, prior to, or following engagement of the subject in one or more rehabilitative activities. The agent(s) may, for example, be administered up to 5 minutes to 12 hours prior to the activity, up to 5 minutes to 12 hours after the activity, during the activity, or immediately prior to or immediately following the start of a therapy session, e.g., up to 5 minutes prior to the beginning of a therapy session or up to 5 minutes following the start of a therapy session. By "therapy session" is meant any period of time in which the subject is engaged in performing activities that have been suggested or prescribed by a health care provider for purposes of assisting the functional recovery of the subject following damage to the CNS or PNS or for improving the functioning of a subject suffering from a neurodevelopmental disorder. The health care provider need not be present during the therapy session, e.g., the subject may perform the activities independently or with the assistance of personnel other than a health care provider.

Administration of Additional Active Agent(s), Cells, and Gene Therapy

In various embodiments of the invention, one or more additional active agents is administered to the subject in conjunction with administration of the plasticity-modifying agent and, optionally, the proteolysis-enhancing agent. The additional active agents may be administered concurrently or sequentially. The additional active agent may be delivered focally but may alternatively be administered systemically using any suitable route of administration (e.g., oral, intravenous, intramuscular, subcutaneous, transdermal, pulmonary, nasal, etc.). The additional active agent may be delivered in the same solution or dosage form as the proteolysis-enhancing agent. The additional active agent may be incorporated into a polymeric matrix together with the proteolysis-enhancing agent and delivered via a polymer-based drug delivery device or delivered using a pump or any other delivery system disclosed herein.

In some embodiments of the invention an agent other than a proteolytic agent is administered, wherein the agent cleaves one or more components of the extracellular matrix at a bond other than a peptide bond. For example, the agent may cleave a polysaccharide portion of an ECM component such as a proteoglycan or glycosaminoglycan. Examples of suitable agents include chondroitinases (which cleave chondroitin sulfate and hyaluronic acid), hyaluronidases, heparinases (which cleave heparin), heparanase (which cleaves heparan sulfate), etc.

In certain embodiments of the invention, the additional active agent is a neural growth enhancing agent. A neural growth enhancing agent is any molecule or cell that promotes, enhances, increases, etc., one or more aspects of the growth or regeneration of neural tissue. For example, the molecule or cell may promote axon growth. A neural growth enhancing agent, as used herein, can be a neurally active growth factor, neurotransmitter or neurotransmitter analog, neurally active metal, modulator of a synaptic signaling molecule, or cell. It will be understood that typically "cell," as used in this context, refers to multiple cells. The term "neurally active" means that the agent exerts a biological effect on neural tissue. For example, the agent may exert an effect that enhances structural and/or functional nervous system reorganization or recovery.

The invention therefore provides compositions comprising a plasticity-modifying agent, a neural growth enhancing agent, and, optionally a proteolysis-enhancing agent. The invention provides drug delivery devices comprising the composition. The drug delivery device can be, for example, any of the drug delivery devices described herein.

The invention further provides methods for promoting recovery or reorganization in the nervous system of a subject comprising the step of: administering a plasticity-modifying agent, a neural growth enhancing agent, and, optionally a proteolysis-enhancing agent to a subject in need of enhancement of recovery or reorganization of the nervous system. The subject is typically in need of recovery or reorganization of the nervous system as a result of ischemic, hemorrhagic, neoplastic, degenerative, traumatic, and/or neurodevelopmental damage to the nervous system. The invention provides methods of treating a subject in need of enhancement of recovery or reorganization in the nervous system comprising the step of: administering a plasticity-modifying agent, a neural growth enhancing agent, and, optionally a proteolysis-enhancing agent to the subject. The subject is typically in need of enhancement of recovery or reorganization of the nervous system as a result of ischemic, hemorrhagic, neoplastic, degenerative, traumatic, and/or neurodevelopmental damage to the nervous system. Any of the agents in the aforementioned methods can be administered focally to the central or peripheral nervous system either individually or in combination using any of the methods described herein. Either or both of the agents can be administered by any alternate route of administration. Certain features of this aspect of the invention, e.g., dose ranges, adjunct therapy, etc., can be similar to those described for other aspects of the invention.

Neurally active growth factors include, but are not limited to, nerve growth factor (NGF), brain-derived neurotrophic factor (BDNF), neurotrophin-1 (NT-3), neurotrophin-4/5 (NT-4/5), ciliary neurotrophic factor (CNTF), leukemia inhibitory factor (LIF), glial cell derived growth factor (GDNF), neurturin, artemin, persephin, acidic or basic fibroblast growth factor (aFGF, bFGF), osteogenic protein-1 (OP-1), vascular endothelial growth factor (VEGF), erythropoietin (EPO), and granulocyte colony stimulating factor (G-CSF).

"Synaptic signaling molecules" refer to endogenous molecules that are activated downstream of calcium entry into cells through synaptic activation or following release of calcium from intracellular stores and that transduce electrical activity into structural changes in neurons. These include a variety of kinases such as calcium/calmodulin-dependent protein kinase II and IV, protein kinase C (PKC), protein kinase A (PKA), extracellular signal regulated kinase (ERK), cyclic AMP (cAMP) dependent kinase, along with molecules such as cyclic AMP response element binding protein (CREB), activity regulated cytoskeletal associated protein (arc), troponin C; and Rac and Rho pathways and their associated kinases. G protein coupled receptors transduce information from the extracellular space to intracellular signals (among other activities) and are also considered to be synaptic signaling molecules. Modulators (i.e., agents that activate or inhibit) of a number of these signaling molecules are known in the art and are of use in the present invention. Molecules that can bind to G protein coupled receptors importantly include those that can activate or inhibit (a) PKA and cAMP; (b) cyclic GMP, and (c) PKC. Pathways downstream of GPCR activation importantly regulate CREB, BDNF, actin, reorganization of the dendritic and axonal cytoskeleton, etc. By way of example, activators of cAMP include Sp-cAMPS (Sigma), which may to be delivered into the brain at a typical dose of 0.02-0.5 µg/kg/day, and Rolipram® (Sigma), which can be given intramuscularly at a dose of 1-100 µg/kg/day (Ramos et al., Neuron 2003). Rolipram is a phosphodiesterase inhibitor, which prevents breakdown of cAMP. Inhibition of cAMP can also, under certain conditions, have a stimulatory effect on synapses and is of use in certain embodiments of the invention. Inhibitors of cAMP include Rp-cAMPS (Sigma), which can be delivered into the brain at a typical dose of 0.02-0.5 µg/kg/day (Ramos et al., 2003).

An activator of cGMP is 8-Br-cGMP; an inhibitor is Rp-cGMPs. Both are typically delivered focally. Effective doses on neurite growth and dynamics in brain slices are about 10-100 µM (Nishiyama et al., 2003). Another inhibitor is ODQ; an effective dose for influencing axon growth is about 10 µM (Leamey et al., 2001). Activators of PKC include diacylglycerol and phosphatidylserine. An inhibitor is a drug called GF109203X (GFX). Effective doses in slices are approximately 10-100 µM (Nishiyama et al., 2003).

It is noted that doses presented here should in no way be considered limiting. In general, the invention encompasses doses at least 10 to 100 fold lower than those described here, and doses up to the maximum tolerated dose of the agent, as consistent with sound medical judgment. Furthermore, dosage routes for specific agents are mentioned here by way of example and are not intended to be limiting. In general, any suitable route of administration can be used. In particular, any of these agents may be administered using the methods for focal administration described herein.

Neurally active small molecules include a number of the modulators and neurotransmitters described above as well as diverse compounds known in the art to influence nervous system function (see, e.g., *Goodman and Gilman*, supra; and Kandel, supra).

Neurotransmitters are naturally occurring compounds that generally fall into the categories of small molecules (e.g., catecholamines) and peptides. A neurotransmitter for use in the present invention can be excitatory or inhibitory. Exemplary neurotransmitters include, but are not limited to, acetylcholine, dopamine, serotonin, glycine, glutamate, epinephrine, norepinephrine, and gamma aminobutyric acid (GABA). A neurotransmitter analog as used herein is a compound other than a naturally occurring neurotransmitter that exerts an excitatory or inhibitory effect on a neurotransmitter receptor. The analog will typically bear a structural resemblance to a naturally occurring neurotransmitter and will compete with it for binding to its receptor.

Neurally active metals include magnesium and zinc. The magnesium and/or zinc can be provided in any suitable form. Typically the metal will be provided in the form of a salt that contains a metal cation and an anion that serves as a counterion. The counterion can be an organic or inorganic substance. For example, the counterion can be phosphate, carbonate, gluconate, citrate, sulfate, acetate, maltonate, oxalate, or any other pharmaceutically acceptable ion such as those mentioned below. In some embodiments the metal cation is provided as a chelate, in which the metal cation is complexed with an organic molecule such as a heterocyclic ring.

Gene therapy methods may be used to increase expression of genes that encode products, e.g., plasticity-enhancing agents, proteolysis-enhancing agents, and/or agents that promote nervous system functional and/or structural reorganization and/or recovery. Gene therapy encompasses delivery of nucleic acids comprising templates for synthesis of a molecule of interest to a cell of interest. The nucleic acid (or a nucleic acid derived from the nucleic acid as, for example, by reverse transcription) may be incorporated into the genome of the cell or remain permanently in the cell as an episome. Gene therapy also encompasses delivery of nucleic acids that do not integrate or remain permanently in the cell to which they are delivered. Such approaches permit temporary or transient synthesis of a molecule of interest. Methods and materials for performing gene therapy are well known in the art and will not be extensively reviewed here (see, e.g., Berry, 2001; Han, 2000; and Thomas and Klibanov, 2003).

Vectors and delivery vehicles (e.g., polymeric matrices) that provide nucleic acids comprising templates for synthesis of polypeptides may be incorporated into a composition of the invention or administered separately. Typically, the nucleic acid includes a coding sequence for a gene to be expressed in a cell of interest and also includes appropriate expression signals, e.g., promoters, terminators, etc., to ensure proper expression.

In general, either viral or non-viral vectors may be used. For example, herpes virus, adenovirus, adeno-associated virus, retroviruses, or lentiviruses may be used. It may be desirable to avoid the use of intact viruses in delivering templates to cells. Thus it may be desirable to deliver DNA vectors or linear DNA molecules. These vectors may, but need not, include viral sequences such as long terminal repeats, etc. Any of a wide variety of agents useful for transfection may be used to enhance uptake of nucleic acids by cells. Vectors are taken up by cells in the nervous system, and the polypeptide of interest is expressed and, usually secreted.

In some embodiments of the invention, cells are administered to a subject. In some embodiments of the invention, cells serve as a source for a plasticity-enhancing agent. For example, the cells may secrete IGF1 into the extracellular space. In certain embodiments of the invention, cells are genetically modified prior to their administration to increase their synthesis of a plasticity-enhancing agent. For example, cells may be stably transformed with a vector that comprises a template for transcription of an RNA that encodes the agent. Cells may be sequestered in a non-biodegradable reservoir or compartment that retains them at a particular location and prevents their integration with cells at the site of administration or their wider dispersal.

In some embodiments of the invention, cells are administered to a subject who may receive a composition comprising a plasticity-modifying agent and optionally a proteolysis-enhancing agent. In some embodiments cells contribute to structural and/or functional recovery of the nervous system. Cells can be neurons, glia, or non-neural cells. Suitable cells include, but are not limited to, Schwann cells and olfactory ensheathing glia (Bunge, 2003). Cells can be of a single cell type, or combinations of different cell types can be administered. Cells may replace or supplement neural tissue that has been irreversibly damaged and/or provide supportive functions. In some embodiments, neural stem cells are administered. Multipotent neural stem cells, capable of giving rise to both neurons and glia, line the cerebral ventricles of all adult animals, including humans. Distinct populations of nominally glial progenitor cells, which also have the capacity to generate several cell types, are dispersed throughout the subcortical white matter and cortex (Goldman 2005). In some embodiments, adult or embryonic stem cells are administered. Such cells can be derived from a location outside the nervous system, e.g., the bone marrow, liver, umbilical cord, etc. Cells of any type can be used. Cells can be autologous or non-autologous. In certain embodiments, cells are from the same species as the subject.

In certain embodiments of the invention the cells are administered in a polymeric scaffold, made of certain of the materials such as those described above that provide a hospitable environment to maintain cell viability. The polymer material may be biodegradable. The matrix or scaffold may be formed prior to implantation into the nervous system of a subject or may form following administration, e.g., upon contact with physiological fluids. Encapsulation of cells in a variety of different polymeric matrices or scaffolds is well known in the art (see, e.g., U.S. Pat. Nos. 6,129,761 and 6,858,229; U.S. Patent Publication 2002/0160471; and Teng, 2002).

In addition to or instead of the various active agents described above, which are selected primarily based on their useful properties for enhancing structural or functional recovery or reorganization in the nervous system, various other substances can be administered. Such substances include, but are not limited to, antibiotics or antifungal agents to treat or reduce the risk of infection, chemotherapeutic agents to treat tumors, etc.

It is to be understood that the invention explicitly includes compositions comprising each specific combination of any of the proteolysis-enhancing agents described herein, optionally in combination with any of the proteolysis-enhancing agents described herein and/or any of the additional active agents described herein. Because it would not be practical to list each and every combination, only a few examples are provided here. For example, the invention includes a composition comprising IFNγ and tPA. The composition may further include a neurally active growth factor (e.g., BDNF). The invention also includes a composition comprising tPA and a modulator of a synaptic signaling molecule (e.g., tPA and Rolipram); a composition comprising tPA and a neurotransmitter (e.g., tPA and serotonin); a composition comprising tPA and a neurally active metal (e.g., tPA and magnesium); a composition comprising tPA and a neurally active small molecule; a composition comprising tPA and a cell (e.g., tPA and a neural stem cell), etc. Similarly, the invention includes compositions comprising (i) plasmin and (ii) a neurally active growth factor, a synaptic signaling molecule, a neurotransmitter, a neurally active metal, and/or a cell. Compositions comprising 3, 4, 5, or more of the proteolysis-enhancing agents and/or additional agents are encompassed. The invention provides a polymer-based drug delivery device comprising any of these compositions and an implantable microchip comprising any of these compositions or designed to administer the agents individually.

The invention encompasses administration of one or more of any of the proteolysis-enhancing agents described herein in conjunction with one or more of any of the additional agents described herein to a subject in need of reorganization and/or recovery of the nervous system. The subject has typically experienced ischemic, hemorrhagic, neoplastic, traumatic, degenerative, and/or neurodevelopmental damage to the central or peripheral nervous system. Agents can be administered together or separately. In some embodiments both the proteolysis-enhancing agent(s) and the additional agent(s) are administered focally. In some embodiments, the proteolysis-enhancing agent(s) are administered focally to the nervous system and the additional agent(s) are administered by an alternate route (e.g., intravenously or orally).

Therapeutic Applications and Adjunct Therapy

The compositions and methods of the invention are of use in treating subjects who have experienced events such as stroke or injury (e.g., due to accident or surgery). The compositions and methods of the invention find use for treating subjects suffering from a variety of other diseases and conditions including, but not limited to, neurodegenerative diseases such as multiple sclerosis, amyotrophic lateral sclerosis, subacute sclerosing panencephalitis, Parkinson's disease, Huntington's disease, muscular dystrophy, and conditions caused by nutrient deprivation or toxins (e.g., neurotoxins, drugs of abuse). Certain of the compositions and methods are of use for treating neurodevelopmental diseases such as autism or dyslexia, i.e., diseases in which at least a portion of the nervous system fails to develop normal structure and/or function. Certain of the compositions and methods are of use for treating neuropsychiatric diseases such as schizophrenia and bipolar disorders, i.e., diseases in which at least a portion of the nervous system fails to achieve its typical level of cognitive function. Certain of the compositions and methods are of use for providing cognitive enhancement and/or for treating cognitive decline, e.g., "benign senescent forgetfulness," "age-associated memory impairment," "age-associated cognitive decline," etc. (Petersen 2001; Burns 2002). These terms are intended to reflect the extremes associated with normal aging rather than a precursor to pathologic forms of memory impairment. Thus these conditions are distinct from Alzheimer's disease. Certain of the compositions and methods are of use for treating Alzheimer's disease. In certain embodiments of the invention, the subject does not have, e.g., has not been diagnosed with, Alzheimer's disease. In certain embodiments of the invention the subject is not suspected of having Alzheimer's disease. In certain embodiments of the invention the subject has not been identified as having an increased risk for developing Alzheimer's disease. Methods for treating or preventing Alzheimer's disease, to the extent that any such methods are described and/or enabled in PCT Publication WO 01/58476 are explicitly excluded from certain embodiments of the instant invention.

Any of a wide variety of functional impairments may be treated using the compositions and methods of the invention. In some embodiments, compositions are used to promote restoration of respiratory function after spinal cord injury (SCI). For this purpose, compositions are typically administered to the spinal cord, e.g., intrathecally. If desired, administration can be localized to the region of the spinal cord injury, e.g., the cervical region of the spinal cord. Respiratory disorders are the leading cause of morbidity and mortality after SCI, affecting nearly half of all patients with a neurological deficit after SCI. Respiratory impairments resulting from cervical SCI, the most common clinical case, frequently render survivors chronically or permanently ventilator dependent, a sequelae which can dramatically compromise quality of life. There are no drug treatments for breathing disorders associated with SCI. Studies have established that the breathing system possesses a highly dynamic system of neuroplasticity which manifests both at the developmental stage as well as at the adulthood. Work in the laboratory of one of the inventors has demonstrated that even with nearly 50% phrenic respiratory motor region loss in the adult rat spinal cord, respiratory function can recover spontaneously in 5-6 weeks after a mid-cervical spinal cord injury. While the ultimate outcome from this neuroplasticity-mediated event is encouraging, the required lengthy period imposes serious life or death challenges to SCI patients. The present invention may significantly stimulate post-SCI respiratory neural circuit reorganization, and thus may quickly restore respiratory function after incomplete spinal cord transection, which is a frequent clinical occurrence.

Surgery for various conditions can sometimes result in damage to nerves. In some embodiments of the invention, the compositions and methods are used to regenerate, repair or otherwise restore function after nerves of the PNS supplying muscles, organs, or other parts of the body, or carrying information from a part of the body, have been necessarily or accidentally disconnected or damaged during surgery. In some embodiments, the present invention is used to regenerate, repair or prevent degeneration of nerves, e.g., nerves supplied by the spinal cord to the muscles, organs, or other parts of the body, or that enter the spinal cord from sensory receptors from the body. Some embodiments include regeneration or repair of damaged or degenerated nerves in the CNS, for example the optic nerve or the auditory nerve, or prevention of degeneration of axon tracts or fiber bundles in the CNS due to diseases, disorders, and/or damage. These embodiments include, but are not limited to, the regrowth, recovery, repair or prevention of degeneration of ascending or descending fiber tracts and connections in the spinal cord, and of fiber tracts and connections in other structural and functional subdivisions of the CNS. Some embodiments include rewiring or reorganizing brain pathways so as to elicit novel functions from existing brain regions. An example of this embodiment is enhancement of brain function, particularly when coupled with practice regimens that engage specific brain regions.

In certain embodiments of the invention, the subject to whom a composition of the invention is administered is engaged in a program of rehabilitative therapy or training. Such programs typically ensue after injury or stroke, but also include programs of remediation and training in a variety of disorders of developmental or adult onset. Such programs are commonly employed in disorders such as dyslexia, autism, Asperger's Syndrome, Pervasive Developmental Disorders—Not Otherwise Specified, Tourette's Syndrome, Personality Disorders, Schizophrenia and related disorders (see, e.g., Diagnostic and Statistical Manual of Mental Disorders, 4th Ed., DSM-IV, American Psychiatric Association, 1994, *Diagnostic and Statistical Manual*, Am. Psychiatric Assoc., Washington, D.C. for discussion of these disorders). Numerous rehabilitation programs for victims of stroke, spinal cord injury, and/or other forms of nervous system damage are known to those skilled in the art, and the subject can be engaged in any such program (see, e.g., Gillen and Burkhardt, supra, for a discussion of suitable programs for victims of stroke). Similar programs may be used for victims of other forms of damage to the brain (see, e.g., Somers, supra, for a discussion of suitable programs for victims of spinal cord damage). Suitable programs for individuals suffering from damage to the PNS are also known in the art. A rehabilitation program is typically designed and recommended by a health care provider with knowledge in the area of rehabilitative therapy. Therapy sessions may involve the participation of a health care provider. However, the subject may also engage in sessions or tasks associated with the program without the assistance or supervision of the health care provider.

The subject can be engaged in the program in a defined temporal relation with respect to the administration of the agent. For example, the subject can be engaged in the program during a time period in which the agent is being administered and/or during which the agent is present in effective amounts in the nervous system. In some embodiments, a dose of the agent is administered within a defined time period prior to engagement of the subject in a particular rehabilitative session or task. For example, the agent may be administered and/or may be present in an effective amount at any time up to 24 hours, 48 hours, or up to 1 week prior to the time at which the subject will be engaged in the session or task, or the agent may be administered and/or may be present in an effective amount at any time up to 24 hours, 48 hours, or up to 1 week following completion of the session or task. Typically the subject will be engaged in the program over a period of weeks, months, or years, i.e., the subject will participate in multiple therapy sessions over a period of time. The subject's participation in such sessions can be coordinated with administration of the agent so as to achieve an optimal effect. The beneficial effects of rehabilitative therapy may at least in part be due to structural and/or functional reorganization that occurs as a result of such therapy. Without wishing to be bound by any theory, the inventors propose that the proteolysis-enhancing activities and/or synaptic plasticity activities of the agents disclosed herein may facilitate this process. Thus an at least additive and potentially synergistic effect may result.

The methods and compositions of the invention may be tested using any of a variety of animal models for injury to the nervous system. Models that may be used include, but are not limited to, rodent, rabbit, cat, dog, or primate models for thromboembolic stroke (Krueger and Busch, 2001; Gupta, 2004), models for spinal cord injury (Webb et al., 2004), etc. (see Examples 6 and 7 and references in Schmidt and Leach, 2003). The methods and compositions may also be tested in humans.

A variety of different methods, including standardized tests and scoring systems, are available for assessing recovery of motor, sensory, behavioral, and/or cognitive function in animals and humans. Any suitable method can be used. To give but one example, the American Spinal Injury Association score, which has become the principal instrument for measuring the recovery of sensory function in humans, could be used (see, e.g., Martinez-Arizala A., 2004; Thomas and Noga, 2004; Kesslak J P and Keirstead H S, 2003; for examples of various scoring systems and methods).

Desirable dose ranges for use in humans may be established by testing the agent(s) in tissue culture systems and in animal models taking into account the efficacy of the agent(s) and also any observed toxicity.

Pharmaceutical Compositions

Suitable preparations, e.g., substantially pure preparations of the proteolysis-enhancing agents, optionally together with one or more additional active agents, may be combined with pharmaceutically acceptable carriers, diluents, solvents, etc., to produce an appropriate pharmaceutical composition. In general, methods and ingredients for producing pharmaceutical compositions known to one of skill in the art are used. The description herein is for exemplary purposes and is not intended to be limiting. It is to be understood that the pharmaceutical compositions of the invention, when administered to a subject, are typically administered for a time and in an amount sufficient to treat the disease or condition for whose treatment they are administered. Suitable modes of administration and formulations are described herein.

Further provided are pharmaceutically acceptable compositions comprising a pharmaceutically acceptable derivative (e.g., a prodrug) of any of the agents of the invention, by which is meant any non-toxic salt, ester, salt of an ester or other derivative of an agent of this invention that, upon administration to a recipient, is capable of providing, either directly or indirectly, an agent of this invention or an active metabolite or residue thereof. As used herein, the term "active metabolite or residue thereof" means that a metabolite or residue thereof also possesses similar activity to the parent agent. For example, rather than administering an active polypeptide, a zymogen (i.e., an inactive or less active enzyme pre-cursor that requires a biochemical change, such as a hydrolysis reaction revealing the active site, for it to become an active enzyme) could be administered.

The term "pharmaceutically acceptable carrier, adjuvant, or vehicle" refers to a non-toxic carrier, adjuvant, or vehicle that does not destroy the pharmacological activity of the agent with which it is formulated. Furthermore, it is recognized that preparation methods for the pharmaceutical compositions are typically selected so as to not substantially reduce the activity of the agent with which they are formulated.

Pharmaceutically acceptable salts of certain of the agents of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates. Salts derived from appropriate bases include alkali metal (e.g., sodium and potassium), alkaline earth metal (e.g., magnesium), ammonium and $N+(C1-4\ alkyl)4$ salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Pharmaceutical compositions suitable for injection or infusion typically include sterile aqueous solutions (where water soluble) or dispersions and sterile powders for the extemporaneous preparation of sterile injectable solutions or dispersion. Suitable carriers include physiological saline, bacteriostatic water, water for injection, dextrose solutions, phosphate buffered saline (PBS), or Ringer's solution. Antibacterial and/or antifungal agents; chelating agents, such as ethylenediaminetetraacetic acid; buffers such as acetates, citrates, or phosphates; and agents for the adjustment of tonicity, such as sodium chloride or dextrose, can be included. pH can be adjusted with acids or bases, such as hydrochloric acid or sodium hydroxide. It may be advantageous to formulate the compositions in dosage unit form for ease of administration and uniformity of dosage. Dosage unit form as used herein refers to physically discrete units suited as unitary dosages for the subject to be treated; each unit containing a predetermined quantity of active agent(s) calculated to produce the desired therapeutic effect in association with the required pharmaceutical carrier. The preparation can, for example, be enclosed in ampoules, disposable syringes or multiple dose vials made of glass or plastic.

Sterile injectable or infusable solutions can be prepared by incorporating the active compound in the required amount in an appropriate solvent, optionally with one or a combination of ingredients enumerated above, followed by filtered sterilization. Typically solutions are free of endotoxin. Generally, dispersions are prepared by incorporating the active compound into a sterile vehicle which contains a basic dispersion medium and optionally other ingredients. In the case of sterile powders for the preparation of sterile solutions, the usual methods of preparation are vacuum drying and freeze-drying (e.g., lyophilization) which yields a powder of the active ingredient plus any additional desired ingredient from a previously sterile-filtered solution thereof.

EXAMPLES

Example 1

Identification and Analysis of Genes that are Differentially Regulated Under Visual Deprivation Paradigms Materials and Methods RNA Preparation and Microarray Analysis Studies were performed in mice (129/SvEv) at the peak of the critical period[28], postnatal day (P) 27. All animal protocols were approved by MIT's Committee on the Care and Use of Animals and followed NIH guidelines. For monocular deprivation (MD), animals were anesthetized with avertin (0.016 ml/g) and the eyelids of one eye sutured (at P11-12 for 15-16 days for microarray analyses). For dark-reared (DR) animals (aged P27-30), the procedure was the same described above, with the exception that the animals were anesthetized in darkness and not exposed to light until deeply anaesthetized; in these mice only the binocular response was evaluated and compared to that in control animals.

In a first set of experiments we extracted total RNA from V1 of normally reared P27 mice (control, n=3 samples), from V1 of P27 mice born and reared in darkness (DR, n=3 samples), and from V1 contralateral to the deprived eye of P27 mice in which monocular deprivation was started at P11-12, before eye-opening (MD, n=6 samples; three samples were done with deprivation of the right eye and 3 with deprivation of the left eye; these 6 samples were considered as a group because no significant differences were observed between right and left eye deprivation). For each sample, animals came from different litters and the tissue was derived from V1 of at least two different animals. In both groups of animals, monocular and binocular portions were included for analysis.

Mice were anesthetized with Nembutal (100 mg/kg), decapitated and the skull opened. A micro blade was used to remove a small core of tissue from the visual cortex of the appropriate hemisphere. Total RNA was extracted and purified, according to the instructions in the "Eukaryotic Target Preparation" manual available on the Affymetrix website. Fragmented, biotinylated cRNA was hybridized to the Affymetrix mouse genome U74v2 GeneChip set, which contains oligonucleotides that correspond to a total of 36,902 probes targeting genes and expressed sequence tags (ESTs) (Affymetrix). Array processing (hybridization, washing, staining and scanning) was performed by the Biopolymer Laboratory at MIT following standard Affymetrix protocols. A global scaling algorithm was used to normalize the expression level data from all samples.

In additional experiments in which the effects of short-term (4 days from P23-27) MD were investigated, as well the effects of IGF1 infusion concurrent with MD, a total of four experimental groups were analyzed: a new group of control animals (3 samples), the ipsilateral and the contralateral cortex of mice monocularly deprived for four days (3 samples for the ipsilateral and 3 samples for the contralateral cortex), the contralateral cortex of mice that were monocularly deprived for four days and were injected IP daily with IGF1 solution (3 samples). Tissue was removed and the RNA extracted as described above, and labeled RNA was hybridized to the Affymetrix mouse genome 430.2 chip, which contains oligonucleotides that correspond to a total of 42,000 probes targeting genes and ESTs.

Data Analysis

Significance Analysis of Microarrays

A method for the Significance Analysis of Microarrays to assess changes in gene expression was used[31], and the method was implemented in MATLAB (The Mathworks, Natick, Mass.). The method allows the comparison of the expression level of each gene under two conditions (e.g., MD vs. control; or DR vs. control). Under the null hypothesis that there are no changes in expression, the output is a probability of observing the given differences by chance (obtained by shuffling the data from the two conditions). Results of this analysis were compared against those obtained by setting a fixed threshold on the minimum intensity of each gene and a minimum ratio of expression between the two conditions. Correlations between replicates were calculated as correlation coefficients (c.c.) for all conditions: control (c.c.=0.99±0.002), MD 16 days (c.c.=0.9±0.05), MD 4 days contralateral (c.c.=0.99±0.001), MD 4 days ipsilateral (0.99±0.005), MD 4 days contralateral plus IGF1 (c.c.=0.99±0.004).

GO Annotations

For the first set of experiments, Gene Ontology (GO) annotations were retrieved for each of the genes (www.geneontology.org/). Mapping of each Affymetrix probe to gene names was done using the annotations from Affymetrix (www.affymetrix.com/). GO provides information about the molecular function of a given gene (e.g. nucleic acid binding, ion transporter activity, etc.), the biological processes in which is involved (e.g. cell growth, cell communication), and the cellular location (e.g. nucleus, cytoplasm, etc.). For each of these organizing principles, GO provides a list of different categories to which each gene may be assigned. FatiGO[32] was used to identify categories for biological functions that are over- or under-represented in the different protocols of visual input deprivation.

Semi-Quantitative RT-PCR

RNA was extracted as described above and cDNA was obtained with the Superscript First-Strand Synthesis System for RT-PCR (Invitrogen). PCR was performed according to the Invitrogen instruction manual. For each sample, PCR was run for the selected molecules and for Glycerol Phosphate Dehydrogenase (GPDH) as a control. PCR products were stained with ethidium bromide and run on an agarose gel. The intensity of each band was evaluated with ImageJ software (rsb.info.nih.gov/ij/) and normalized by the level of GPDH expression.

Results

Figure 1:
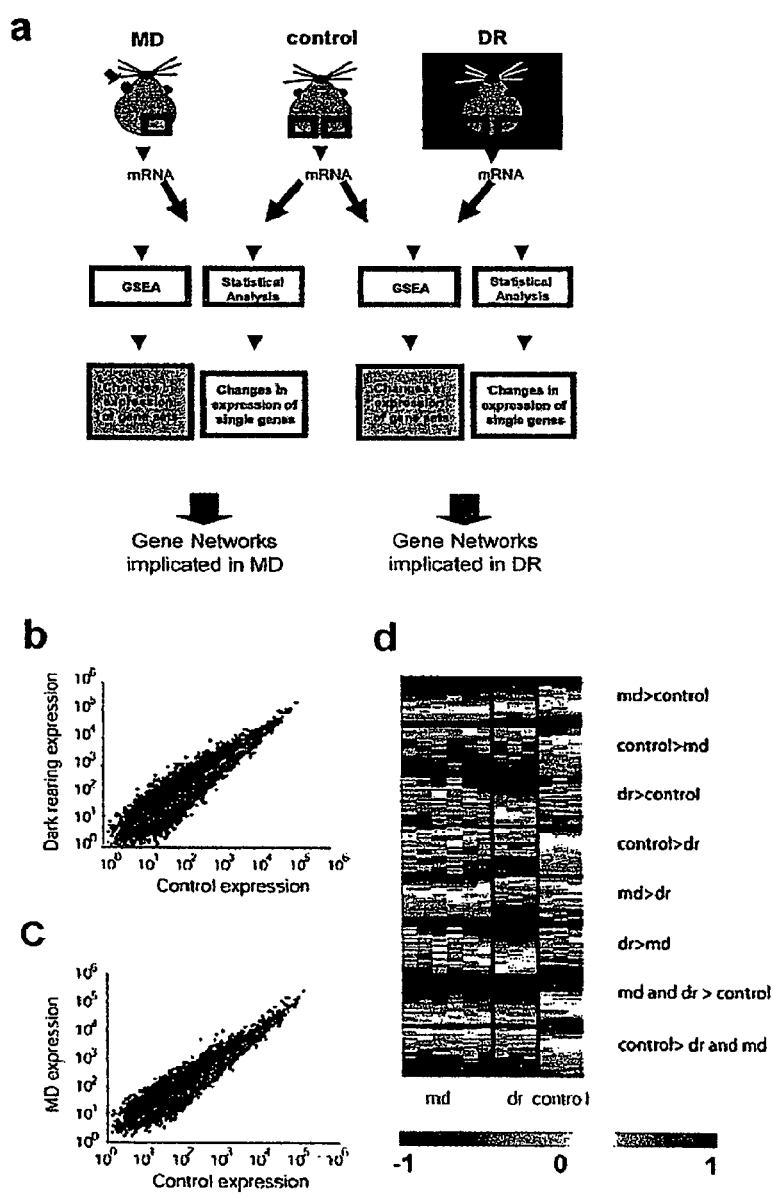
FIG. 1: Analysis and characterization of genes activated in different paradigms of visual input deprivation. (A) Three experimental groups were considered: control mice, dark-reared (DR) mice and monocularly-deprived (MD) mice. From each sample, tissue from anatomically defined primary visual cortex (V1) was taken at P27. For control and DR mice, V1 was taken from both hemispheres, while for MD mice only V1 contralateral to the deprived eye was used. For each sample, total RNA was extracted and processed for the microarray procedure. MD and DR samples were compared to the control independently, each with two different computational methods (see Example 1): the Significance Analysis of Microarrays (SAM) for analysis of single genes, and gene set enrichment analysis (GSEA). Each procedure identified single genes or gene sets that were up- or down-regulated in deprived groups versus control. This led to the identification of cellular events involved in the two models of input deprivation. (B, C) Comparison of gene expression in (B) dark-reared versus control and (C) monocularly deprived versus control animals, showing the expression levels of all probes. Genes showing significantly different expression levels ($p \leq 0.01$) are shown in red (overexpression in deprivation protocol) or in green (overexpression in control). Gene expression is shown on a logarithmic scale. The dashed white line corresponds to identity (y=x). (D) Heat map showing the levels of expression of representative genes that showed differential expression among those selected for our analysis ($p \leq 0.01$). Each column corresponds to a separate sample (n=6 for MD, n=3 for DR and n=3 for control). High levels of expression correspond to brilliant red, low levels of expression correspond to dark blue (see bottom of the figure for color scale). For each group, 25 randomly chosen genes among the significant genes are shown here. Genes within each group are sorted based on their expression values.

DNA microarrays were used to examine large scale changes in gene expression in the V1 region of the cortex following dark-rearing (DR) and monocular deprivation (MD), using quantitative analyses of single genes as well as computational analyses of gene network activation (FIG. 1A). Mice used for microarray analyses of long-term visual deprivation were: (a) DR animals reared in complete darkness from birth till P27, the peak of the critical period for ocular dominance plasticity in mice[28], (b) MD animals which had one eyelid sutured from before eye-opening (at P11-12) through P27, and (c) P27 control animals, reared in standard conditions (FIG. 1A). The time course of the deprivation protocols was chosen to ensure as comparable periods of deprivation as possible in the DR and MD conditions—that is, starting at birth and continuing till P27. V1 was identified by stereotaxic coordinates and its location confirmed with both optical imaging of intrinsic signals[29] and by retrograde labeling of cells in the lateral geniculate nucleus (LGN) from injections of Alexa-CTB made in cortex[30]. RNA was extracted from V1 and hybridized to microarrays (Affymetrix). First, the expression level of gene transcripts was compared between control and deprived animals using a procedure for the Significance Analysis of Microarrays[31] (FIGS. 1B, C). Two lists of genes were obtained for each deprivation protocol: those that were up-regulated in the deprived conditions versus control (1930 genes: 1730 genes up-regulated after DR and 200 genes up-regulated after MD), and those which were down-regulated in the deprived conditions versus control (1381 genes: 950 genes down-regulated after DR and 431 genes down-regulated after MD; FIG. 1D). The complete list of significantly (P≤0.01) up- and down-regulated genes is reported in tables for each experiment at (ramonycajal.mit.edu/kreiman/resources/v1plasticity/) and in Tables 4-9 herein (presented in the Appendix).

The Gene Ontology (GO) database[32,33] was used to group differentially expressed genes according to the biological processes in which they are involved. Of the 3311 differentially expressed genes in visually deprived groups, 1227 have known functions and have been reported in GO categories (level 3) for general biological processes. This analysis showed that some biological processes are common to both deprivation conditions, whereas others are differentially, or even exclusively, represented in one condition or the other.

For instance, genes implicated in "metabolism" and "cell communication" were upregulated in both conditions, with a stronger representation in DR cortex. At the same time, genes implicated in "cell motility" and "cell growth and maintenance" were primarily upregulated after DR. On the other hand, genes comprising "cellular physiological processes" and "organismal physiological processes" were primarily upregulated after MD. This overview suggested that while some similar mechanisms underlie the two forms of deprivation, distinct cellular processes may also be implicated in the two conditions.

To analyze the distinction further, a more detailed examination of genes encoding glutamatergic and GABA receptors was performed, including subunits of NMDA, AMPA and metabotropic glutamate receptors and subunits of GABA-A and GABA-B receptors. Table 1 shows changes in the expression of different subunits of GABA and glutamate receptors in MD and DR. "+" indicates a significant (two tailed t test P≤0.05) increase in the mRNA level in the deprived condition relative to control; "=" indicates no significant change. No gene was downregulated after deprivation relative to control.

| Receptor | MD | DR |
| --- | --- | --- |
| GluR1 | = | + |
| GluR2 | + | + |
| GluR3 | + | + |
| NMDA1 | = | + |
| NMDA2A | = | + |
| NMDA2B | = | + |
| NMDA2C | = | = |
| NMDA2D | = | = |
| mGluR3 | = | = |
| mGluR5 | = | = |
| mGluR8 | = | = |
| GABAAα1 | = | + |
| GABAAα2 | + | + |
| GABAAα3 | + | + |
| GABAAα4 | = | + |
| GABAAα6 | + | = |
| GABAAβ1 | + | + |
| GABAAβ2 | = | + |
| GABAAβ3 | + | + |
| GABAAγ1 | = | = |
| GABAAγ2 | = | + |
| GABAAγ3 | = | = |
| GABAAδ | = | = |

-continued

| Receptor | MD | DR |
|---|---|---|
| GABAAε | = | = |
| GABAB1 | = | = |
| GABACρ1 | = | = |
| GABACρ2 | = | = |

This comparison of the main forms of excitatory and inhibitory transmission in the cortex showed that a substantial set of excitatory and inhibitory receptor genes was upregulated after DR. MD also upregulated both sets, but a smaller subset than DR (FIG. 2A). None of these receptor genes was downregulated after either form of deprivation. Thus, expression of both excitatory and inhibitory receptor genes is broadly upregulated in response to visual deprivation, but the response is stronger in the case of DR, where there is complete absence of light, than in the case of MD, where there is still visual stimulation through the closed eyelid though not in patterned form[34].

Several studies have reported that DR induces a delay in the maturation of inhibition[11,35,36]. No change in GAD65 expression was observed after DR or MD, but an increase in GAD67 expression was observed after DR (FIG. 2B). More generally, a reduction was observed in expression of only one gene associated with cortical inhibitory neurons: all the probes associated with parvalbumin were downregulated after DR, whereas probes associated with other markers of inhibitory neurons[37,38], including calbindin, somatostatin, calretinin, cholecystokinin and neuropeptide Y, were either upregulated or did not change after DR (FIG. 2B). There was no change in any of these markers after MD (see also below, and FIG. 9). Thus, the functional reduction of inhibition and of inhibitory neurons after DR[36] is possibly mediated specifically by a reduction in the number of neurons expressing parvalbumin.

Next, the microarray expression levels of a subset of genes (FIG. 3A) were compared to an independent measure of gene expression using semi-quantitative RT-PCR performed on independent samples from those used for microarrays. The genes selected were significantly up-regulated (two-tailed t test $P<0.05$) in DR or MD cortex versus control, with at least a 1.5-fold greater expression after one or other form of deprivation. Furthermore, selected genes were in the top 5% in a list of probes rank-ordered by change in expression after DR or MD, based on calculation of the signal to noise ratio of each gene (from the mean microarray expression levels and standard deviations in deprived and control conditions). Analysis of representative genes that were upregulated after DR alone, after MD alone, or after both, is shown in FIGS. 3B,C. Genes upregulated after DR (but not MD) in the microarray data included molecules associated with synaptic structure and function, such as those involved in synapse formation (Neurexin1 and Synapsin 2), synaptic transmission mechanisms such as exocytosis (Synaptotagmin 1), neurotransmitter receptors (GluR1), and calcium-activated signaling (CaMKIIα and CREB). Changes observed with RT-PCR were consistent with the observations from the microarray data. That is, an increase in the expression of these molecules in the DR cortex was observed, and there was a greater increase in the DR condition compared to MD for each of them.

Fewer genes were up-regulated after MD (but not DR) compared to control, and they included molecules that are usually implicated in cellular pathology, including carcinogenesis (the DEAD-box RNA helicase DDX6[39]) and degeneration (Signal Transducers and Activators of Transcription 1, STAT1—see below), or are activated by seizure (CaMKIIδ[40]). These genes also showed greater expression in the RT-PCR analysis. Finally, genes that were upregulated after both DR and MD included molecules associated with synaptic activity (GluR3 and GABA-Aα2), as well as molecules associated with neuronal growth and reorganization of connections (Insulin-like Growth Factor Binding Protein 5, IGFBP5—see below), and aspects of brain development (Nuclear Factor IB, NfiB[41-43]). In all of these instances, relative expression levels measured with RT-PCR were consistent with the microarray expression levels. Overall, these data suggest increased activation of a wide range of synaptic and neuronal mechanisms in V1 of DR animals, and to a lesser extent in MD animals, compared to control animals. Conversely, they suggest an increased activation of neuronal growth and degeneration mechanisms in MD animals, and to a lesser extent in DR animals, compared to control animals.

While the effects of MD are pronounced in the long term, they are also significant in the short term[14-17]. To examine similarities and differences with the long (16 day) period of MD, a microarray analysis of a short (4 day) period of MD, from P23-27, was performed. Short-term MD led to changes in the expression of many more genes than long-term MD. About 50% of the genes that were up- or down-regulated after long-term MD were also altered in expression after short-term MD; the upregulated genes included DDX6, IGFBP5 and NFiB. Genes upregulated by long-term MD but not short-term MD included STAT1 and CaMKIIδ. While some genes associated with synaptic transmission (such as GluR1, GluR3 and GABA-Aα2) did not change after short-term MD, more transmission-related genes (such as Synapsin 2 and Synaptotagmin 1) were up- or down-regulated after short-term compared to long-term MD.

Example 2

Identification of Gene Sets and Pathways Enriched in Genes that are Differentially Regulated in Visual Deprivation Paradigms Materials and Methods Gene Set Enrichment Analysis (GSEA) considers even small variations in all the mRNA probes of a group of genes, thereby assessing the enrichment of the whole gene set, and is relevant for detecting modest but coordinated changes in the expression of groups of functionally related genes. Such an analysis has particular value when an increase in the activity of several genes in a set could be more important than the strong activation of a single gene in a molecular cascade. Furthermore, the genes in the set typically share some functional or structural properties. Different gene sets have different sizes (for example, the gene set "Channel-passive-transporter" has 238 probes, while the "IGF1 pathway" has 46 probes), and all the probes corresponding to a single gene are reported in each gene set. A recent description of the method[44] was followed here; a more detailed description has now appeared[85].

Let $_S\mu_i$ denote the mean expression level across samples of probe i (i=1, . . . , N where N is the total number of probes) in condition S (where S=DR, MD or control) and let $_S\sigma_i$ denote the standard deviation across samples. For a given probe i, the signal to noise ratio (SNR) of the deprivation condition is defined with respect to the control. For example, for dark rearing, the SNR was defined as $$_{DR}SNR_i = \frac{_{DR}\mu_i - _{control}\mu_i}{_{DR}\sigma_i - _{control}\sigma_i}.$$

Probes were ranked according to the SNR value yielding an ordered list $L=\{g_1, \ldots, g_N\}$.

Given a set G containing $N_G$ probes it can be assessed whether the set of probes is significantly over- or under-represented in one of the deprivation conditions with respect to the control condition (irrespective of whether the expression of the individual probes changed significantly or not). A representative example illustrating the algorithm is shown in FIG. 4A. The following two cumulative distribution functions are defined: $P_{hit}(i)$=proportion of genes in the set G that show a rank less than $$\left(P_{hit}(i) = \frac{\# \ [g_{(j \leq i)} \in G]}{N_G}\right)$$

and $P_{miss}(i)$=proportion of genes outside the set G that show a rank less than $$\left(P_{miss}(i) = \frac{\# \ [g_{(j \leq i)} \notin G]}{N - N_G}\right).$$

The running enrichment score is defined as $RES(i)=P_{hit}(i) - P_{miss}(i)$ (FIG. 4A, top) and is derived from the position or rank of the genes in the set (FIG. 4A, bottom). The enrichment score ES is the maximum deviation from 0 of RES(i). If the genes in the set are highly enriched in the deprivation condition and appear first in the ordered list L, then $P_{hit}$ will grow faster with i than $P_{miss}$ for initial values of i and this will lead to a high positive ES value. Conversely, if the genes in the set are under-expressed in the deprivation condition and do not appear at the beginning of the list L, then $P_{miss}$ will grow faster with i than $P_{hit}$ and this will lead to a high negative ES score. If the genes in the set are randomly distributed, then the ES will show a value close to 0. The statistical significance of a particular value of ES is assessed by comparing it with the null distribution obtained by randomly shuffling the condition labels (deprivation and control) for each probe (using 1,000 permutations).

The procedure just described was repeated for each gene set, obtaining an enrichment score and an enrichment probability value for each set. It is possible to define a set of genes based on several different criteria. Here, sets of genes defined by common functional or structural properties in 3 specific biological databases were studied: BioCarta (www.biocarta.com/), GenMapp (www.genmapp.org/), and GO (www.geneontology.org/). When a large number of gene sets is considered as in the present case, care should be taken because of the multiple comparisons involved and therefore the increased likelihood that one comparison will yield a significant result by chance. The multiple comparisons question was addressed here by controlling the Family Wise Error Rate[6]. To compare enrichment scores across gene sets, the enrichment scores are normalized by centering and scaling the ES using the mean and variance of each data, gene set pair. Throughout the text and in Tables 4 and 5, the normalized enrichment scores (NES) is shown for the gene sets enriched in dark rearing or monocular deprivation relative to control, or vice versa.

Results

Apart from the expression of individual genes, sets of genes that are linked together in specific functional pathways may be differentially expressed in DR and long-term MD and thereby lead to different cellular and molecular responses following the two forms of deprivation. To examine this possibility, a computational tool was used—Gene Set Enrichment Analysis (GSEA)—that considers the activation of sets of genes (such as cellular pathways, co-expressed genes, or genes in the same genomic locus) rather than the expression of a single transcript[44,45]. Thus, the extent to which a set of genes or a pathway is enriched in the deprivation paradigms was able to be measured with respect to control (or vice versa). 1374 pathways and gene sets taken from the following databases were considered: BioCarta, GenMapp, and GO. An example of the computation of the running and normalized enrichment score (NES) is shown in FIG. 4A for the ADP Ribosylation Factor (ARF) Pathway. The expression levels for the 19 probes in this pathway are shown in FIG. 4B. Qualitatively, FIG. 4B shows that most of these probes were more highly expressed after MD than in control. Quantitatively, FIG. 4A shows that many of these probes were highly ranked in the rank-ordered set of MD probes, leading to a high running enrichment score for the ARF pathway. The gene sets with the highest scores in the deprived conditions versus control are listed in Table 2, which is a representation of the top Gene Sets enriched in DR (left column) and MD (right column) versus control. The Gene Sets are ranked according to their Normalized Enrichment Score. Gene Sets that are enriched in both conditions are shown with light shading. A star indicates that at least one probe of the correspondent Gene Set has been confirmed with RT-PCR. The gene sets with the highest scores in the control versus deprived conditions (i.e., are downregulated after deprivation) are listed in Table 3. The Gene Sets are ranked according to their Normalized Enrichment Score.

TABLE 3

| | C > DR | NES | C > MD | NES |
|---|---|---|---|---|
| 1 | Neuropeptide_hormone | −17.0 | 20S_core_proteasome_complex | −5.3 |
| 2 | Gas_exchange | −14.3 | Ribosome | −4.6 |
| 3 | Scavenger_receptor | −13.1 | Circulation | −4.0 |
| 4 | Serine_type_endopeptidase | −12.8 | NADH_dehydrogenase | −4.0 |
| 5 | Enzyme_binding_activity | −12.6 | NADH_dehydrogenase_ubiquinone_activity | −3.8 |
| 6 | Spliceosomal_subunit | −10.1 | Endopeptidase_activity | −3.6 |
| 7 | chr4q21 | −9.1 | Structural_constituent_of_ribosome | −3.2 |

These pathways were all significantly enriched (permutation test, P<0.0001) within the data set, based on a statistical comparison of enrichment scores obtained with 1000 randomly permuted gene sets. The GSEA method revealed quantitatively that different gene sets were preferentially activated after DR and MD. For example, the top enriched gene sets after DR included those involved in cellular activity, encompassing both metabolism related pathways (such as "metabolism" and "growth hormone pathway"), and synaptic activity related networks (such as "channel passive transporter," "vesicle-coat-protein," and "secretory vesicles"). After MD, however, the majority of the top enriched gene sets corresponded to pathways activated by growth factors ("epidermal growth factor," "insulin-like growth factor 1," and "platelet derived growth factor") and neuronal remodeling and degeneration ("nuclear factor of activated T cells," "JAK-STAT cascade," and "embryogenesis and morphogenesis"). Several gene sets were enriched in both conditions but were ranked in a different order confirming that common processes are also shared between the two conditions.

TABLE 2

| | DR > C | NES | MD > C | NES |
|---|---|---|---|---|
| 1 | Channel_passive_transporter ★ | 27.3 | egfPathway ★ | 16.4 |
| 2 | Metabolism | 25.6 | igf1Pathway ★ | 9.7 |
| 3 | mapkPathway ★ | 22.6 | EGF_receptor_signaling_pathway | 9.5 |
| 4 | Vesicle_coat_protein | 21.6 | pdgfPathway ★ | 8.7 |
| 5 | chr14q31 | 21.0 | Embryogenesis_and_morphogenesis | 8.0 |
| 6 | ghPathway | 20.0 | Helicase_activity ★ | 7.9 |
| 7 | chr8p12 | 18.8 | tpoPathway ★ | 7.6 |
| 8 | Secretory_vesicles ★ | 18.6 | nfatPathway ★ | 7.5 |
| 9 | chr20p12 | 17.8 | Monocyte_AD_pathway | 7.0 |
| 10 | Apoptosis_regulator_activity | 17.6 | arfPathway | 6.8 |
| 11 | Protein_amino_acid_phosphorylation | 17.4 | JAK_STAT_cascade ★ | 6.7 |
| 12 | chr4q12 | 17.3 | Differentiation_in_PC12 ★ | 6.6 |
| 13 | rarrxrPathway | 17.1 | Channel_passive_transporter ★ | 6.4 |
| 14 | ATPase_activity | 17.0 | tcrPathway ★ | 6.2 |
| 15 | chr5q33 ★ | 16.8 | Transmembrane_RPTP | 6.0 |
| 16 | insulinPathway | 16.8 | ghPathway ★ | 5.8 |
| 17 | Neurotransmitter_secretion ★ | 16.6 | Inositolphosphatidylinositol_kinase_activity | 5.6 |
| 18 | edg1Pathway | 16.6 | keratinocytePathway | 5.6 |
| 19 | egfPathway | 16.5 | at1rPathway ★ | 5.6 |
| 20 | RAS_protein_signal_transduction | 16.5 | gleevecPathway ★ | 5.6 |
| 21 | Telomerase_dependent_telomere_maintenance | 16.4 | ngfPathway | 5.5 |
| 22 | Endoplasmic_reticulum ★ | 16.0 | il2rbPathway | 5.5 |
| 23 | par1Pathway | 15.6 | Cancer_related_testis ★ | 5.5 |
| 24 | ngfPathway | 15.4 | Adrenergic | 5.4 |
| 25 | at1rPathway ★ | 15.3 | il7Pathway | 5.3 |
| 26 | Cancer_related_testis | 15.3 | il2Pathway ★ | 5.3 |
| 27 | erk5Pathway ★ | 15.2 | Dag1 | 5.3 |
| 28 | JNK_MAPK_pathway | 15.1 | G_alpha_5_pathway ★ | 5.2 |
| 29 | chr15q22 | 15.0 | PTEN_pathway | 5.2 |
| 30 | Ngvm_c8 | 15.0 | cblPathway | 5.1 |
| 31 | arenrf2Pathway ★ | 14.9 | B_cell_receptor_complexes | 5.0 |
| 32 | Microtubule_binding_activity | 14.9 | p53_signalling | 5.0 |
| 33 | arfPathway | 14.7 | arenrf2Pathway ★ | 4.9 |
| 34 | Potassium_ion_transport ★ | 14.5 | chr20p12 | 4.8 |
| 35 | mtorPathway | 14.4 | pitx2Pathway | 4.8 |
| 36 | crebPathway ★ | 14.3 | igf1rPathway | 4.8 |
| 37 | gleevecPathway | 14.3 | hdacPathway ★ | 4.7 |
| 38 | Protein_amino_acid_dephosphorylation | 14.3 | ccr5Pathway ★ | 4.7 |
| 39 | myosinPathway | 14.3 | Insoluble_fraction | 4.6 |
| 40 | pdgfPathway | 14.1 | Granule_cell_survival ★ | 4.4 |
| 41 | Ngvm_c32 ★ | 14.0 | 35_cyclic_nucleotide_phosphodiesterase_activity | 4.4 |
| 42 | Microtubule associated complex | 14.0 | hivnefPathway | 4.3 |
| 43 | Neuronal_transmission ★ | 13.9 | GPI_anchored_membrane_bound_receptor | 4.2 |
| 44 | erkPathway | 13.6 | Positive_regulation_of_transcription | 4.2 |
| 45 | CD40_pathway_map ★ | 13.6 | tnfr1Pathway | 4.2 |
| 46 | Wnt_Signaling | 13.6 | Neuronal_transmission ★ | 4.2 |
| 47 | Ion_transporter_activity | 13.5 | Transmembrane_RTK_signalling | 4.1 |
| 48 | Calmodulin_binding_activity ★ | 13.3 | Synaptic_transmission ★ | 4.1 |
| 49 | GPCR_pathway | 13.1 | spryPathway | 4.1 |
| 50 | chr2p22 | 13.1 | Golgi | 4.0 |

The genes previously identified with RT-PCR as highly expressed after DR or MD were also present in specific gene sets with high NES values (corresponding gene sets are marked), indicating that highly expressed genes together enrich specific pathways or networks of activation. The distribution of positive NES values for the DR versus control comparison is shown in FIG. 4C, which also shows the running enrichment scores for two pathways containing the molecules Creb and GluR1, respectively. The NES distribution for the MD versus control comparison is shown in FIG. 4D, together with the running enrichment scores for two pathways containing the molecules STAT1 and IGFBP5/IGF1, respectively. Each of these genes appears early in the rank-ordered set of DR or MD genes (i.e., is one of the top enriched genes in the set and contributes significantly to the running enrichment score shown in FIGS. 4C, D). Indeed, individual pathways often contain a number of genes that are implicated in DR or MD. Conversely, individual genes are often included in multiple pathways enriched after DR or MD. Many genes are common between the two deprivation conditions, as expected, but several are different (cf. FIG. 3). Considering the 100 most enriched gene sets in deprivation conditions, 1928 probes are present in DR but not MD gene sets, 1590 probes are present in MD but not DR gene sets, and 2361 probes are present in both MD and DR gene sets.

Example 3

Expression of Selected Proteins Encoded by Differentially Expressed Genes

Materials and Methods
Immunohistochemistry

Mice were anesthetized and transcardially perfused with a solution of 4% paraformaldehyde. The appropriate brain hemispheres were removed and equilibrated in 30% sucrose in PBS. Coronal sections containing visual cortex were cut using a freezing microtome. Immunohistochemistry for GluR1 (1:500, Upstate), IGFBP5 (1:500, USBiological), CaMK2alpha (1:500, Sigma), PhosphoCREB (1:500, Cell Signaling), activated Stat1 (1:500, Abcam), parvalbumin (1:1000, Chemicon), calretinin (1:500, Chemicon), somatostatin (1:300, Chemicon), neuropeptideY (1:400, Chemicon), synapsin 1 (1:500, Chemicon), IGF1 (1:250, Chemicon), GAD 67 (1:400, Chemicon), IGF1R (1:500, Upstate), PI3K—catalytic subunit 110 (1:400, Upstate), phosphorylated-Akt (1:250, Cell Signaling), was carried out as described elsewhere[82,83]. For each staining, analysis was repeated in parallel for control and deprived animals. Experiments were carried out at least on two animals for each group and repeated twice. The intensity of staining in sections from control and deprived animals was evaluated with ImageJ software (rsb.info.nih.gov/ij/). Counts of parvalbumin, calretinin, somatostatin and NPY-positive cells were performed as described elsewhere[29].
Results The results described thus far represent information at the mRNA level. Given that multiple control mechanisms can exert their actions after the transcriptional stage, analysis of protein expression is can be used to confirm the functional activation of a pathway beyond RNA analyses. To further examine the regulation of the genes described above and their associated pathways, the expression of their proteins was analyzed using immunohistochemistry.

First, markers were examined for selected classes of interneurons. Since all the microarray probes for parvalbumin were downregulated after DR (FIG. 2B) while other interneuron markers remained unchanged or increased, it was determined whether a similar pattern were reflected in the number of neurons that were immuno-positive for these markers. A significant decrease (by 40%, p<0.01) in the number of parvalbumin-positive neurons in DR relative to control animals (FIG. 5A) was observed, while calretinin-positive neurons remained unaltered and the number of neurons positive for somatostatin and neuropeptide Y increased (P<0.05). For all the antibodies examined, there was no effect of MD on the number of stained neurons. Thus, the reported effect of DR as delaying inhibition is likely due to a delay in the development of neurons that express parvalbumin.

Following up the highly enriched gene sets after DR, the expression of GluR1 (FIG. 5B) phospho-CREB (FIG. 5C), and CaMKIIα were examined, present in the "CREB pathway" gene set. Each of these molecules was over-expressed in V1 of DR animals compared to control, consistent with previous reports of the involvement of CaMKIIα in DR[46], of GluR1 as a substrate for CaMKIIα expression[47], and of CREB-mediated gene expression as related to the maturation of the visual cortex[48]. Similarly, following MD, two novel proteins were examined, activated STAT1 and IGFBP5, which are constituents of highly enriched gene sets, though neither has been previously implicated in the cortical effects of MD or any form of visual deprivation. STAT proteins are phosphorylated by Janus Kinases (JAK); the JAK-STAT cascade is usually activated in response to cytokine signaling, but is also upregulated in response to nerve injury and ischemia[49-51]. Immunostaining for the phosphorylated form of STAT1, indicating activation of the JAK-STAT cascade, showed that the molecule was significantly upregulated in V1 after MD (FIG. 5D). IGFBP5 is widely expressed in the brain[52] and binds IGF1, a peptide that is genetically related to insulin[53,54,55]. IGFBP5 expression was significantly upregulated in V1 after long-term MD (FIG. 5E).

Example 4

Administration of IGF1 Counteracts Effects of Monocular Deprivation

Materials and Methods
Monocular Deprivation

For monocular deprivation, animals were anesthetized with avertin (0.016 ml/g) and the eyelids of one eye were sutured (at P20-22 for 7 days for imaging experiments). Before imaging, the suture was removed and the deprived eye re-opened. Only animals in which the deprivation sutures were intact and the condition of the deprived eye appeared healthy were used for the imaging session. For DR animals (aged P27-30), the procedure was the same described above, with the exception that the animals were anesthetized in darkness and not exposed to light until deeply anaesthetized; in these mice only the binocular response was evaluated and compared to that in control animals.

Optical Imaging of V1

Mice (129/SvEv and C57B1/6) aged P26-30 were anesthetized with urethane (1.5 g/Kg) and chlorprothixene (0.2 mg), as described[84]. Skin was excised and the skull exposed over V1. A custom-made attachment was used to fix the head and minimize movements. The cortex was covered with agarose solution (1.5%) and a glass cover slip. During the imaging session the animal's body temperature was kept constant with a heating blanket and the EKG monitored constantly. Eyes were periodically treated with silicone oil and the animal allowed to breathe pure oxygen. Red light (630 nm) was used to illuminate the cortical surface, and the change of luminance was captured by a CCD camera (Cascade 512B, Roper Scientific) during the presentation of visual stimuli (STIM, Optical Imaging). Custom software was developed to control the image acquisition and synchronization between the camera and stimuli. An elongated horizontal or vertical white bar (9°×72°) over a uniformly gray background was drifted continuously through the up-down or peripheral-central dimension of the visual field. After moving to the last position, the bar would jump back to the initial position and start another cycle of movement—thus, the chosen region of visual space (72°×72°) was stimulated in periodic fashion (9 sec/cycle). Images of visual cortex were continuously captured at the rate of 15 frames/sec during each stimulus session of 25 minutes. Four sets of stimuli (upward, downward, leftward, rightward) were randomly presented to either eye monocularly or both eyes simultaneously.

A temporal high pass filter (135 frames) was employed to remove slow noise components, after which the temporal Fast Fourier Transform (FFT) component at the stimulus frequency (9 sec$^{-1}$) was calculated pixel by pixel from the whole set of images. No spatial averaging was done. The amplitude of the FFT component was used to measure the strength of visually driven response for each eye, and the ocular dominance index was derived from each eye's response (R) at each pixel as ODI=(Rcontra−Ripsi)/(Rcontra+Ripsi). The binocular zone was defined as the region with equivalent driving from both eyes.

IGF1 Treatment

For IGF1 treatment, a solution containing GPE, the functional peptide of IGF1, was prepared as described[56]: 300 μg of GPE was injected intra-peritoneally daily for the entire period of deprivation. This peptide is referred to as "IGF1" in the Results below.

Results

IGFBP5 is one of the most upregulated genes after MD, with one of the highest mRNA expression levels after RT-PCR, and the highest differential level of protein expression after MD or DR. Furthermore, the IGF1 pathway is one of the top enriched pathways after MD in the GSEA, and both IGFBP5 and IGF1 are constituents of several highly enriched pathways after MD. The present invention encompasses the recognition that the upregulation of IGFBP5 following MD could imply a competitive role for IGF1 in mediating ocular dominance plasticity after MD, and that exogenous application of IGF1 could then prevent the effect of MD (see, for example, ref. 56). The possible functional involvement of the IGF1/IGFBP5 system in experience-dependent plasticity in visual or any cortex has not been examined to date. Thus, the physiological effects of IGF1 administration on ocular dominance plasticity in V1 were determined in vivo (FIG. 6).

IGF1 is able to cross the blood brain barrier[56], thus, intraperitoneal administration of IGF1 prevents the effects of ischemia in the CNS[57]. Optical imaging of intrinsic signals was used to evaluate the strength of signals from each eye in the physiologically identified binocular portion of V1 (FIG. 6A). Imaging was performed on three age-matched groups of mice during the critical period: control animals (n=3), animals monocularly deprived for 7 days (n=4), and MD animals with IGF1 delivered intraperitoneally during the period of deprivation (n=3). FIG. 6B shows the ocular dominance distribution of pixels within the binocular zone in individual control, MD and MD+IGF1 animals. The pixel distribution in control mice favored the contralateral eye, as described previously with single unit recordings[28] and visual evoked potentials[58]. Suturing the contralateral eye caused the ocular dominance distribution to shift towards the open, ipsilateral, eye. Simultaneous administration of IGF1 prevented the ocular dominance shift towards the open eye. A comparison of the mean ocular dominance index across the population of animals (FIG. 6C) showed that deprivation of the contralateral eye shifted the index significantly relative to control animals (P<0.05, treating each animal as a single datum), whereas MD combined with administration of IGF1 prevented the shift (P>0.2).

The mechanisms of IGF1/IGFBP5 action were investigated by asking if specific cell types and proteins were associated with the pathway. To clarify whether IGFBP5 is expressed in excitatory or inhibitory neurons, a double immunostaining for IGFBP5 and GAD67 was performed, and IGFBP5 was shown to be expressed in a range of neurons—not exclusively in inhibitory interneurons (FIG. 7A). Next the expression in V1 of several molecules involved in IGF1 signaling[53,59] was assayed by immunostaining after MD alone and after MD with concurrent delivery of IGF1 (FIG. 7B). IGFBP5 immunostaining showed a significant increase after short-term MD, and no change from normal levels in short-term MD animals that also received IGF1 during the deprivation period (MD+IGF1). Expression of the IGF1 receptor (IGF1R), on the other hand, was significantly down-regulated after MD, and expression was partially restored in MD+IGF1 animals. Phosphatidylinositol 3-Kinase (PI3K), which is activated by IGF1, was significantly diminished in expression after MD but was fully restored after MD+IGF1 treatment (P<0.05 for both comparisons; FIG. 7B).

Expression of one of the substrates of PI3K, phosphorylated-Akt, was significantly reduced by MD and restored by addition of IGF1. Because IGF1 and PI3K signaling have been related to neuronal transmission[60-62], changes in synaptic activity were screened for by immunostaining for synapsin 1. The level of synapsin expression did not change significantly in MD animals versus control, but MD+IGF1 animals showed a significant increase (P<0.05). Finally, a microarray analysis of MD+IGF1 animals was performed for comparison with MD animals, to examine genes that might be differentially regulated by IGF1 and hence be associated specifically with IGF1 mechanisms. Expression of only a small fraction of genes was significantly altered in MD+IGF1 animals compared to MD animals (see Tables 10 and 11). Adding IGF1 significantly downregulated IGFBP5 and upregulated PI3K compared to MD alone (P<0.01). Thus, PI3K appears to be an important signal downstream of IGF1 in mediating ocular dominance plasticity.

Example 5

Release of a Plasticity-Modifying Agent from Hydrogel Discs

In order to demonstrate the release of a plasticity-modifying agent over time from a hydrogel matrix suitable for drug delivery, hydrogel discs containing various amounts of IGF1 are fabricated and subjected to incubation in a PBS solution, during which release of IGF1 is measured over time.

The hydrogel consists of a poly(ethylene glycol) (PEG) core with poly(lactic acid) (PLA) linkages (i.e., it contains hPLA-b-PEG-PLA macromers) and has been previously described (Sawhney, et al., 1993; and Burdick, et al., 2002). In order to fabricate discs, the hydrogel macromer is combined with IFNγ and the photoinitiator 2-hydroxy-1-[4-(hydroxyethoxy)phenyl]-2-methyl-1-propanone, (Ciba-Geigy) in a PBS solution. The solution (50 μl) is placed into a mold of the desired dimensions and then crosslinked under UV light for 10 minutes to cause polymerization, thereby resulting in discs of hydrogel with dimensions of approximately 5 mm by 1 mm.

The hydrogel discs are placed in 0.5 ml of PBS solution and release is monitored over 14 days using an ELISA kit according to the manufacturer's directions. Three hydrogel discs are tested for each of the conditions (2 different loading doses each for single-chain and two-chain tPA), and the amount of tPA released was averaged at each time point. Data are analyzed to determine the relationship between IGF1 release and the amount of IGF1 present in the disc. The relationship allows for the control of the amount of IGF1 released by changing the amount of IGF1 initially loaded into the gel. The total amount of IGF1 released can be calculated from the concentrations and the fact that the discs are incubated in 0.5 ml PBS solution. This information can be used to determine the amount of IGF1 and the amount of hydrogel needed to deliver a desired dose over time.

Example 6

Effect of IGF1 on Recovery from Spinal Cord Injury

Materials and Methods

In a first set of experiments, 6 female Sprague-Dawley rats were anesthetized and spinal cord injury (SCI) was induced at T10 by using the New York University impactor with a 10 gm weight and a 12.5 mm weight drop. Behavioral tests were conducted on the first post-operative day and then weekly. The BBB (Basso, Beattie, Bresnahan) behavioral test was used to examine hind limb reflexes as well as coordinated use of the hind limbs (Basso et al., 1995; and Basso, et al., 1996). This "BBB" scale has been adopted by the Multicenter Animal Spinal Cord Injury Study and by other workers in the field. Therefore, use of the BBB as an outcome measure after experimental SCI supports easier interlaboratory comparison of results.

A second operation is conducted three days post-operatively at T8-T9 for a bolus micro-injection of 10 μg of IGF1 or GPE and, in some experiments, also 10 μg of tPA (human two-chain tissue plasminogen activator; American Diagnostica, Inc.) reconstituted from lyophilized powder to 10 μg/10 μL) into three of the six rats. Following the bolus injection, an osmotic minipump (Alzet Model 2002: 14 day pump; Durect Corp., Cupertino, Calif.) loaded with IGF1 or GPE and, in some experiments, also tPA (200 μL total volume, delivering 0.5 μl/hour, 10 μg IGF1 or GPE, and, in some experiments, 10 μg tPA/day) is implanted at the side of injury and delivered tPA for 10 consecutive days. At the $6^{th}$ post-operative week, BDA and Fluorogold injections are made in cortex to assess the extent of corticospinal tract regrowth and reconnection, and at the $10^{th}$ post-operative week, animals are perfused and their spinal cords were removed for histological analysis. Implanted minipumps are saved for analysis of IFG1 activity (and in some experiments tPA activity) in the remaining solution.

A second set of experiments is performed on a larger group of animals using the same techniques as the first except that Alzet Model 1007B:7 day pumps holding a total volume of 90 μl, infusing 0.5 μl/hour are used, and delivery continues for 7 days rather than 10.

In a third set of experiments, GPE is administered intraperitoneally at a range of different doses (10 μg-1 mg) daily.

In a fourth set of experiments, GPE is administered intraperitoneally at a range of different doses (10 μg-1 mg) daily and a pump delivering tPA is implanted as described above.

In all experiments, the extent of corticospinal tract regrowth and reconnection is evaluated and histology is performed. Anatomical analysis with hematoxylin and eosin staining is performed to evaluate the contusion site. Sections are stained with solvent blue [SB]/hematoxylin and eosin as described in Teng and Wrathall, 1997. The integrity of the residual white matter is assessed. For example, high quality myelin stain in the spared white matter demonstrates existence of myelinated axons.

Functional parameters are assessed. Pre-operatively, animals performance on the BBB test is expected to have a baseline value of 21. On the first post-operative day, all animals are expected to be significantly impaired on the BBB test, and their scores reduced to 0. After 10 weeks of recovery, control animals typically achieve a final score of about 2.5 on the BBB test while treated animals are expected to achieve a higher score, e.g., a final score close to 9, which is considered significant improvement.

Example 7

Effect of IGF1 with or without tPA in an Animal Model of Stroke

Thirty rats are trained on a battery of behavioral tasks until they achieved an asymptotic level of competence. Rats then receive occlusion of the middle cerebral artery (MCAO) according to standard procedures. After recovery from surgery, the rats are significantly impaired on all of the behavioral tasks. At the time of MCAO surgery, 20 of the 30 rats are also implanted with an osmotic mini-pump (Alzet model 2001: 7 day pump with 90 μl total volume and 1.0 μl/hour infusion) for intraventricular infusion contralateral to the site of the MCAO. For 10 of the 20 rats, the mini-pumps are filled with IGF1 at 10 μg/day. For the other 10 rats the mini-pumps are filled with IGF1 at 10 μg/day and human two-chain tissue plasminogen activator (tPA; American Diagnostica, Inc.) at 10 μg/day. The other 10 rats receive daily intraperitoneal injections of GPE at a dose ranging from 10 μg to 10 mg, e.g., 300 μg.

Treatment is initiated 2 days following MCAO and maintained for 7 days. Control and treated rats are subsequently tested weekly for behavioral recovery.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., plasticity-modifying condition, any plasticity-modifying agent, any proteolysis-enhancing agent, any active agent, any drug delivery system, any mode of administration, any dosage regimen, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

REFERENCES

1. Katz, L. C. & Shatz, C. J. Synaptic activity and the construction of cortical circuits. *Science* 274, 1133-8 (1996).
2. Sur, M. & Leamey, C. A. Development and plasticity of cortical areas and networks. *Nat Rev Neurosci* 2, 251-62 (2001).
3. Berardi, N., Pizzorusso, T., Ratto, G. M. & Maffei, L. Molecular basis of plasticity in the visual cortex. *Trends Neurosci* 26, 369-78 (2003).
4. Hensch, T. K. Critical period regulation. *Annu Rev Neurosci* 27, 549-79 (2004).
5. Desai, N. S., Cudmore, R. H., Nelson, S. B. & Turrigiano, G. G. Critical periods for experience-dependent synaptic scaling in visual cortex. *Nat Neurosci* 5, 783-9 (2002).
6. Wallace, W. & Bear, M. F. A morphological correlate of synaptic scaling in visual cortex. *J Neurosci* 24, 6928-38 (2004).
7. Kirkwood, A., Rioult, M. C. & Bear, M. F. Experience-dependent modification of synaptic plasticity in visual cortex. *Nature* 381, 526-8 (1996).
8. Philpot, B. D., Espinosa, J. S. & Bear, M. F. Evidence for altered NMDA receptor function as a basis for metaplasticity in visual cortex. *J Neurosci* 23, 5583-8 (2003).
9. Fagiolini, M., Pizzorusso, T., Berardi, N., Domenici, L. & Maffei, L. Functional postnatal development of the rat primary visual cortex and the role of visual experience: dark rearing and monocular deprivation. *Vision Res* 34, 709-20 (1994).
10. Morales, B., Choi, S. Y. & Kirkwood, A. Dark rearing alters the development of GABAergic transmission in visual cortex. *J Neurosci* 22, 8084-90 (2002).
11. Iwai, Y., Fagiolini, M., Obata, K. & Hensch, T. K. Rapid critical period induction by tonic inhibition in visual cortex. *J Neurosci* 23, 6695-702 (2003).
12. Turrigiano, G. G. & Nelson, S. B. Homeostatic plasticity in the developing nervous system. *Nat Rev Neurosci* 5, 97-107 (2004).
13. Wiesel, T. N. & Hubel, D. H. Single-Cell Responses in Striate Cortex of Kittens Deprived of Vision in One Eye. *J Neurophysiol* 26, 1003-17 (1963).
14. Trachtenberg, J. T., Trepel, C. & Stryker, M. P. Rapid extragranular plasticity in the absence of thalamocortical plasticity in the developing primary visual cortex. *Science* 287, 2029-32 (2000).
15. Trachtenberg, J. T. & Stryker, M. P. Rapid anatomical plasticity of horizontal connections in the developing visual cortex. *J Neurosci* 21, 3476-82 (2001).
16. Oray, S., Majewska, A. & Sur, M. Dendritic spine dynamics are regulated by monocular deprivation and extracellular matrix degradation. *Neuron* 44, 1021-30 (2004).
17. Mataga, N., Mizuguchi, Y. & Hensch, T. K. Experience-dependent pruning of dendritic spines in visual cortex by tissue plasminogen activator. *Neuron* 44, 1031-41 (2004).
18. Shatz, C. J. & Stryker, M. P. Ocular dominance in layer IV of the cat's visual cortex and the effects of monocular deprivation. *J Physiol* 281, 267-83 (1978).
19. Antonini, A. & Stryker, M. P. Rapid remodeling of axonal arbors in the visual cortex. *Science* 260, 1819-21 (1993).
20. Crowley, J. C. & Katz, L. C. Development of ocular dominance columns in the absence of retinal input. *Nat Neurosci* 2, 1125-30 (1999).
21. Crowley, J. C. & Katz, L. C. Early development of ocular dominance columns. *Science* 290, 1321-4 (2000).
22. Crair, M. C., Gillespie, D. C. & Stryker, M. P. The role of visual experience in the development of columns in cat visual cortex. *Science* 279, 566-70 (1998).
23. Tagawa, Y., Kanold, P. O., Majdan, M. & Shatz, C. J. Multiple periods of functional ocular dominance plasticity in mouse visual cortex. *Nat Neurosci* 8, 380-8 (2005).

24. Yang, C. B., Zheng, Y. T., Li, G. Y. & Mower, G. D. Identification of Munc 13-3 as a candidate gene for critical-period neuroplasticity in visual cortex. *J Neurosci* 22, 8614-8 (2002).
25. Prasad, S. S. et al. Gene expression patterns during enhanced periods of visual cortex plasticity. *Neuroscience* 111, 35-45 (2002).
26. Ossipow, V., Pellissier, F., Schaad, O. & Ballivet, M. Gene expression analysis of the critical period in the visual cortex. *Mol Cell Neurosci* 27, 70-83 (2004).
27. Lachance, P. E. & Chaudhuri, A. Microarray analysis of developmental plasticity in monkey primary visual cortex. *J Neurochem* 88, 1455-69 (2004).
28. Gordon, J. A. & Stryker, M. P. Experience-dependent plasticity of binocular responses in the primary visual cortex of the mouse. *J Neurosci* 16, 3274-86 (1996).
29. Newton, J. R., Ellsworth, C., Miyakawa, T., Tonegawa, S. & Sur, M. Acceleration of visually cued conditioned fear through the auditory pathway. *Nat Neurosci* 7, 968-73 (2004).
30. Majewska, A. & Sur, M. Motility of dendritic spines in visual cortex in vivo: changes during the critical period and effects of visual deprivation. *Proc Natl Acad Sci USA* 100, 16024-9 (2003).
31. Tusher, V. G., Tibshirani, R. & Chu, G. Significance analysis of microarrays applied to the ionizing radiation response. *Proc Natl Acad Sci USA* 98, 5116-21 (2001).
32. Al-Shahrour, F., Diaz-Uriarte, R. & Dopazo, J. FatiGO: a web tool for finding significant associations of Gene Ontology terms with groups of genes. *Bioinformatics* 20, 578-80 (2004).
33. Ashburner, M. & Lewis, S. On ontologies for biologists: the Gene Ontology—untangling the web. *Novartis Found Symp* 247, 66-80; discussion 80-3, 84-90, 244-52 (2002).
34. Akerman, C. J., Smyth, D. & Thompson, I. D. Visual experience before eye-opening and the development of the retinogeniculate pathway. *Neuron* 36, 869-79 (2002).
35. Papadopoulos, G. C., Cavanagh, M. E., Antonopoulos, J., Michaloudi, H. & Parnavelas, J. G. Postnatal development of somatostatin-containing neurons in the visual cortex of normal and dark-reared rats. *Exp Brain Res* 92, 473-8 (1993).
36. Benevento, L. A., Bakkum, B. W. & Cohen, R. S. gamma-Aminobutyric acid and somatostatin immunoreactivity in the visual cortex of normal and dark-reared rats. *Brain Res* 689, 172-82 (1995).
37. Lund, J. S. & Lewis, D. A. Local circuit neurons of developing and mature macaque prefrontal cortex: Golgi and immunocytochemical characteristics. *J Comp Neurol* 328, 282-312 (1993).
38. Flames, N. & Marin, O. Developmental mechanisms underlying the generation of cortical interneuron diversity. *Neuron* 46, 377-81 (2005).
39. Abdelhaleem, M. Do human RNA helicases have a role in cancer? *Biochim Biophys Acta* 1704, 37-46 (2004).
40. Murray, K. D., Isackson, P. J. & Jones, E. G. N-methyl-D-aspartate receptor dependent transcriptional regulation of two calcium/calmodulin-dependent protein kinase type II isoforms in rodent cerebral cortex. *Neuroscience* 122, 407-20 (2003).
41. das Neves, L. et al. Disruption of the murine nuclear factor I-A gene (Nfia) results in perinatal lethality, hydrocephalus, and agenesis of the corpus callosum. *Proc Natl Acad Sci USA* 96, 11946-51 (1999).
42. Shu, T., Butz, K. G., Plachez, C., Gronostajski, R. M. & Richards, L. J. Abnormal development of forebrain midline glia and commissural projections in Nfia knock-out mice. *J Neurosci* 23, 203-12 (2003).
43. Steele-Perkins, G. et al. The transcription factor gene Nfib is essential for both lung maturation and brain development. *Mol Cell Biol* 25, 685-98 (2005).
44. Mootha, V. K. et al. PGC-1alpha-responsive genes involved in oxidative phosphorylation are coordinately downregulated in human diabetes. *Nat Genet.* 34, 267-73 (2003).
45. Sweet-Cordero, A. et al. An oncogenic KRAS2 expression signature identified by cross-species gene-expression analysis. *Nat Genet.* 37, 48-55 (2005).
46. Neve, R. L. & Bear, M. F. Visual experience regulates gene expression in the developing striate cortex. *Proc Natl Acad Sci USA* 86, 4781-4 (1989).
47. Xue, J., Li, G., Laabich, A. & Cooper, N. G. Visual-mediated regulation of retinal CaMKII and its GluR1 substrate is age-dependent. *Brain Res Mol Brain Res* 93, 95-104 (2001).
48. Pham, T. A., Impey, S., Storm, D. R. & Stryker, M. P. CRE-mediated gene transcription in neocortical neuronal plasticity during the developmental critical period. *Neuron* 22, 63-72 (1999).
49. Yao, G. L., Kato, H., Khalil, M., Kiryu, S. & Kiyama, H. Selective upregulation of cytokine receptor subchain and their intracellular signalling molecules after peripheral nerve injury. *Eur J Neurosci* 9, 1047-54 (1997).
50. Schwaiger, F. W. et al. Peripheral but not central axotomy induces changes in Janus kinases (JAK) and signal transducers and activators of transcription (STAT). *Eur J Neurosci* 12, 1165-76 (2000).
51. Justicia, C., Gabriel, C. & Planas, A. M. Activation of the JAK/STAT pathway following transient focal cerebral ischemia: signaling through Jak1 and Stat3 in astrocytes. *Glia* 30, 253-70 (2000).
52. Iwadate, H., Sugisaki, T., Kudo, M. & Kizuki, K. Actions of insulin-like growth factor binding protein-5 (IGFBP-5) are potentially regulated by tissue kallikrein in rat brains. *Life Sci* 73, 3149-58 (2003).
53. Bondy, C. A. & Cheng, C. M. Signaling by insulin-like growth factor 1 in brain. *Eur J Pharmacol* 490, 25-31 (2004).
54. Zheng, W. H. & Quirion, R. Comparative signaling pathways of insulin-like growth factor-1 and brain-derived neurotrophic factor in hippocampal neurons and the role of the PI3 kinase pathway in cell survival. *J Neurochem* 89, 844-52 (2004).
55. Obata, S., Obata, J., Das, A. & Gilbert, C. D. Molecular correlates of topographic reorganization in primary visual cortex following retinal lesions. *Cereb Cortex* 9, 238-48 (1999).
56. Sizonenko, S. V., Sirimanne, E. S., Williams, C. E. & Gluckman, P. D. Neuroprotective effects of the N-terminal tripeptide of IGF1, glycine-proline-glutamate, in the immature rat brain after hypoxic-ischemic injury. *Brain Res* 922, 42-50 (2001).
57. Guan, J., Bennet, L., Gluckman, P. D. & Gunn, A. J. Insulin-like growth factor-1 and post-ischemic brain injury. *Prog Neurobiol* 70, 443-62 (2003).
58. Porciatti, V., Pizzorusso, T. & Maffei, L. The visual physiology of the wild type mouse determined with pattern VEPs. *Vision Res* 39, 3071-81 (1999).
59. Laurino, L. et al. PI3K activation by IGF1 is essential for the regulation of membrane expansion at the nerve growth cone. *J Cell Sci* 118, 3653-62 (2005).

60. Liou, J. C., Tsai, F. Z. & Ho, S. Y. Potentiation of quantal secretion by insulin-like growth factor-1 at developing motoneurons in Xenopus cell culture. *J Physiol* 553, 719-28 (2003).
61. Seto, D. et al. Insulin-like growth factor-I inhibits endogenous acetylcholine release from the rat hippocampal formation: possible involvement of GABA in mediating the effects. *Neuroscience* 115, 603-12 (2002).
62. Blair, L. A. & Marshall, J. IGF1 modulates N and L calcium channels in a PI 3-kinase-dependent manner. *Neuron* 19, 421-9 (1997).
63. Lodovichi, C., Berardi, N., Pizzorusso, T. & Maffei, L. Effects of neurotrophins on cortical plasticity: same or different? *J Neurosci* 20, 2155-65 (2000).
64. Bear, M. F., Kleinschmidt, A., Gu, Q. A. & Singer, W. Disruption of experience-dependent synaptic modifications in striate cortex by infusion of an NMDA receptor antagonist. *J Neurosci* 10, 909-25 (1990).
65. Roberts, E. B., Meredith, M. A. & Ramoa, A. S. Suppression of NMDA receptor function using antisense DNA block ocular dominance plasticity while preserving visual responses. *J Neurophysiol* 80, 1021-32 (1998).
66. Hensch, T. K. et al. Local GABA circuit control of experience-dependent plasticity in developing visual cortex. *Science* 282, 1504-8 (1998).
67. Hensch, T. K. & Stryker, M. P. Columnar architecture sculpted by GABA circuits in developing cat visual cortex. *Science* 303, 1678-81 (2004).
68. Pizzorusso, T. et al. Reactivation of ocular dominance plasticity in the adult visual cortex. *Science* 298, 1248-51 (2002).
69. Mataga, N., Nagai, N. & Hensch, T. K. Permissive proteolytic activity for visual cortical plasticity. *Proc Natl Acad Sci USA* 99, 7717-21 (2002).
70. Huang, Z. J. et al. BDNF regulates the maturation of inhibition and the critical period of plasticity in mouse visual cortex. *Cell* 98, 739-55 (1999).
71. Fagiolini, M. et al. Specific GABAA circuits for visual cortical plasticity. *Science* 303, 1681-3 (2004).
72. White, L. E., Coppola, D. M. & Fitzpatrick, D. The contribution of sensory experience to the maturation of orientation selectivity in ferret visual cortex. *Nature* 411, 1049-52 (2001).
73. Corriveau, R. A., Huh, G. S. & Shatz, C. J. Regulation of class I MHC gene expression in the developing and mature CNS by neural activity. *Neuron* 21, 505-20 (1998).
74. Xu, W., Nair, J. S., Malhotra, A. & Zhang, J. J. B cell antigen receptor signaling enhances IFN-gamma-induced Stat1 target gene expression through calcium mobilization and activation of multiple serine kinase pathways. *J Interferon Cytokine Res* 25, 113-24 (2005).
75. Tonner, E. et al. Insulin-like growth factor binding protein-5 (IGFBP-5) potentially regulates programmed cell death and plasminogen activation in the mammary gland. *Adv Exp Med Biol* 480, 45-53 (2000).
76. McGee, A. W., Yang, Y., Fischer, Q. S., Daw, N. W. & Strittmatter, S. M. Experience-driven plasticity of visual cortex limited by myelin and Nogo receptor. *Science* 309, 2222-6 (2005).
77. Wang, W. F., Kiyosawa, M., Ishiwata, K. & Mochizuki, M. Glucose metabolism in the visual structures of rat monocularly deprived by eyelid suture after postnatal eye opening. *Jpn J Opthalmol* 49, 6-11 (2005).
78. Bondy, C. A. & Cheng, C. M. Insulin-like growth factor-1 promotes neuronal glucose utilization during brain development and repair processes. *Int Rev Neurobiol* 51, 189-217 (2002).
79. Maffei, L., Berardi, N., Domenici, L., Parisi, V. & Pizzorusso, T. Nerve growth factor (NGF) prevents the shift in ocular dominance distribution of visual cortical neurons in monocularly deprived rats. *J Neurosci* 12, 4651-62 (1992).
80. Polleux, F., Whitford, K. L., Dijkhuizen, P. A., Vitalis, T. & Ghosh, A. Control of cortical interneuron migration by neurotrophins and PI3-kinase signaling. *Development* 129, 3147-60 (2002).
81. Righi, M., Tongiorgi, E. & Cattaneo, A. Brain-derived neurotrophic factor (BDNF) induces dendritic targeting of BDNF and tyrosine kinase B mRNAs in hippocampal neurons through a phosphatidylinositol-3 kinase-dependent pathway. *J Neurosci* 20, 3165-74 (2000).
82. Tropea, D., Capsoni, S., Covaceuszach, S., Domenici, L. & Cattaneo, A. Rat visual cortical neurones express TrkA NGF receptor. *Neuroreport* 13, 1369-73 (2002).
83. Tropea, D., Caleo, M. & Maffei, L. Synergistic effects of brain-derived neurotrophic factor and chondroitinase ABC on retinal fiber sprouting after denervation of the superior colliculus in adult rats. *J Neurosci* 23, 7034-44 (2003).
84. Kalatsky, V. A. & Stryker, M. P. New paradigm for optical imaging: temporally encoded maps of intrinsic signal. *Neuron* 38, 529-45 (2003).
85. Subramanian, A. et al. Gene set enrichment analysis: a knowledge-based approach for interpreting genome-wide expression profiles. *Proc Natl Acad Sci USA* 102, 15545-50 (2005).
86. Storey, J. D. & Tibshirani, R. Statistical significance for genomewide studies. *Proc Natl Acad Sci USA* 100, 9440-5 (2003).
87. Al-Anazi A, Bernstein M (2000). Modified stereotactic insertion of the Ommaya reservoir. J Neurosurg, 92:1050-1052.
88. Antonini, A., Fagiolini, M., and Stryker, M. P. (1999). Anatomical correlates of functional plasticity in mouse visual cortex. Journal of Neuroscience 19, 4388-4406.
89. Antonini, A., and Stryker, M. P. (1993). Rapid remodeling of axonal arbors in the visual cortex. Science 260, 1819-1821.
90. Russo, V. C., et al., Endocrine Rev., 26(7): 916-943 (2005).
91. Foster, F., et al., J. Cell Sci. 116:3037-3040 (2003).
92. Paez, J. and Sellers, W., Cancer Treat Res. 115:145-67 (2003).
93. Kinney, J., et al., *J. Neurosci.*, 26(5): 1604 (2006).
94. Asselbergs, et al., (1995) J. Biotechnol., 42(3):221-233.
95. Baranes, D., Lederfein, D., Huang, Y. Y., Chen, M., Bailey, C. H., and Kandel, E. R. (1998). Tissue plasminogen activator contributes to the late phase of LTP and to synaptic growth in the hippocampal mossy fiber pathway. Neuron 21, 813-825.
96. Basso, D M, et al., (1995). A sensitive and reliable locomotor rating scale for open field testing in rats. J. Neurotrauma, 12(1):1-21.
97. Basso, D M., et al. (1996). Graded histological and locomotor outcomes after spinal cord contusion using the NYU weight-drop device versus transection. Exp. Neurol., 139 (2): 244-256.
98. Benita et al. (1984) J. Pharm. Sci. 73:1721-1724.
99. Berry, M., et al., (2001) Gene therapy for central nervous system repair, Curr. Opin. Mol. Ther. 3: 338-49.
100. Biernaskie, J. and Corbett J. (2001) Enriched Rehabilitative Training Promotes Improved Forelimb Motor Function and Enhanced Dendritic Growth after Focal Ischemic Injury, The Journal of Neuroscience, 21(14):5272-5280.

101. Bizik, J., et al. (1990) Cell Regul.; 1(12): 895-905.
102. Blue, M. E., and Parnavelas, J. G. (1983). The formation and maturation of synapses in the visual cortex of the rat. II. Quantitative analysis. J Neurocytol 12, 697-712.
103. Bonhoeffer, T., and Yuste, R. (2002). Spine Motility: Phenomenology, Mechanisms, and Function. Neuron 35, 1019-1027.
104. Brody E N, Gold L. (2000) J. Biotechnol., 74(1):5-13.
105. Brummelkamp, T. R., et al. (2002) A system for stable expression of short interfering RNAs in mammalian cells. Science 296:550-553.
106. Bunge, M B and Pearse, D D (2003) J Rehabil Res Dev. 40(4 Suppl 1):55-62. Burns, A. & Zaudig, M (2002). Mild cognitive impairment in older people. The Lancet 360, 1963-1965.
107. Callaway, E. M., and Katz, L. C. (1990). Emergence and refinement of clustered horizontal connections in cat striate cortex. J Neurosci 10, 1134-1153.
108. Callaway, E. M., and Katz, L. C. (1991). Effects of binocular deprivation on the development of clustered horizontal connections in cat striate cortex. Proc Natl Acad Sci USA 88, 745-749.
109. Chen, R., et al. (2002) Neuroscience, "Nervous System Reorganization Following Injury", 111(4): 761-773.
110. Cho, I H, et al., (2004) Purification and characterization of six fibrinolytic serine-proteases from earthworm Lumbricus rubellus. J Biochem Mol. Biol. 2004 Mar. 31; 37(2): 199-205.
111. Cotten and Birnstiel, (1989) EMBO J. 8:3861-3866.
112. Cramer, S., et al. (1997) A functional MRI study of subjects recovered from hemiparetic stroke, Stroke, 28: 2518-2527.
113. Dang W, Daviau T, Brem H (1996). Morphological characterization of polyanhydride biodegradable implant gliadel during in vitro and in vivo erosion using scanning electron microscopy. Pharm Res, 13:683:91.
114. De Felipe, J., Marco, P., Fairen, A., and Jones, E. G. (1997). Inhibitory synaptogenesis in mouse somatosensory cortex. Cereb Cortex 7, 619-634.
115. DeVivo, M. J., Epidemiology of traumatic spinal cord injury, in Kischblum, S., Campagnolo, D. I., DeLlisa, J. A. (eds.) Spinal Cord Medicine, 2002. Lippincott Williams & Wilkins, Philadelphia, pp. 69-81.
116. Dityatev, A., and Schachner, M. (2003). Extracellular matrix molecules and synaptic plasticity. Nat Rev Neurosci 4, 456-468.
117. Dunaevsky, A., Tashiro, A., Majewska, A., Mason, C., and Yuste, R. (1999). Developmental regulation of spine motility in the mammalian central nervous system. Proc Natl Acad Sci USA 96, 13438-13443.
118. Elbashir, S M, et al., (2001) Duplexes of 21-nucleotide RNAs mediate RNA interference in cultured mammalian cells. Nature. 24; 411(6836):494-8.
119. Elokdah H, et al. (2004) Tiplaxtinin, a novel, orally efficacious inhibitor of plasminogen activator inhibitor-1: design, synthesis, and preclinical characterization. J Med Chem. 47(14):3491-4.
120. Emptage, N., Bliss, T. V., and Fine, A. (1999). Single synaptic events evoke NMDA receptor-mediated release of calcium from internal stores in hippocampal dendritic spines. Neuron 22, 115-124.
121. Engert, F., and Bonhoeffer, T. (1999). Dendritic spine changes associated with hippocampal long-term synaptic plasticity. Nature 399, 66-70.
122. Fagiolini, M., Fritschy, J. M., Low, K., Mohler, H., Rudolph, U., and Hensch, T. K. (2004). Specific GABAA circuits for visual cortical plasticity. Science 303, 1681-1683.
123. Fagiolini, M., and Hensch, T. K. (2000). Inhibitory threshold for critical-period activation in primary visual cortex. Nature 404, 183-186.
124. Fawcett, J W and Asher, R A (1999) The glial scar and central nervous system repair. Brain Res Bull. 49(6):377-91.
125. Feng, G., Mellor, R. H., Bernstein, M., Keller-Peck, C., Nguyen, Q. T., Wallace, M., Nerbonne, J. M., Lichtman, J. W., and Sanes, J. R. (2000). Imaging neuronal subsets in transgenic mice expressing multiple spectral variants of GFP. Neuron 28, 41-51.
126. Fischer, M., Kaech, S., Knutti, D., and Matus, A. (1998). Rapid actin-based plasticity in dendritic spines. Neuron 20, 847-854.
127. Fischer, M., Kaech, S., Wagner, U., Brinkhaus, H., and Matus, A. (2000). Glutamate receptors regulate actin-based plasticity in dendritic spines. Nat Neurosci 3, 887-894.
128. Fiumelli, H., Jabaudon, D., Magistretti, P. J., and Martin, J. L. (1999). BDNF stimulates expression, activity and release of tissue-type plasminogen activator in mouse cortical neurons. Eur J Neurosci 11, 1639-1646.
129. Fleming A B, Saltzman W M (2002). Pharmacokinetics of the carmustine implant. Clin Pharmackinet, 41:403-19.
130. Fukazawa, Y., Saitoh, Y., Ozawa, F., Ohta, Y., Mizuno, K., and Inokuchi, K. (2003). Hippocampal LTP Is Accompanied by Enhanced F-Actin Content within the Dendritic Spine that Is Essential for Late LTP Maintenance In Vivo. Neuron 38, 447-460.
131. Furlan, M., et al., (1996) Spontaneous neurological recovery after stroke and the fate of the ischemic penumbra", Ann. Neurol., 40:216-226.
132. Gale K, Kerasidis H, Wrathall J R (1985) Spinal cord contusion in the rat: behavioral analysis of functional neurological impairment. Exp. Neurol 88:123-134.
133. Galicich J H, Guido L J (1974). Ommaya device in carcinomatous and leukemic meningitis. Surgical experience in 45 cases. Surg Clin North Am 54:915-922.
134. Ge, T., et al., (2005) Cloning of thrombolytic enzyme (lumbrokinase) from earthworm and its expression in the yeast Pichia pastoris. Protein Expr Purif. 2005 July; 42(1): 20-8.
135. Gils, A., et al. (2002) Characterization and comparative evaluation of a novel PAI-1 inhibitor. Thromb Haemost. 88(1):137-43.
136. Goldman S. (2005) Stem and progenitor cell-based therapy of the human central nervous system. Nat Biotechnol. 23(7): 862-71.
137. Gordon, J. A., and Stryker, M. P. (1996). Experience-dependent plasticity of binocular responses in the primary visual cortex of the mouse. Journal of Neuroscience 16, 3274-3286.
138. Gray, E. (1959). Electron microscopy of synaptic contacts on dendritic spines of the cerebral cortex. Nature 183, 1592-1593.
139. Gualandris, A., Jones, T. E., Strickland, S., and Tsirka, S. E. (1996). Membrane depolarization induces calcium-dependent secretion of tissue plasminogen activator. J Neurosci 16, 2220-2225.
140. Guo, J T, et al., Nucleic Acids Res. 32 (Web Server issue):W522-5, Jul. 1, 2004).

141. Gupta, Y K and Briyal, S., (2004) Animal models of cerebral ischemia for evaluation of drugs. Indian J Physiol Pharmacol. 48(4):379-94.
142. Hall, A. (1998). Rho GTPases and the actin cytoskeleton. Science 279, 509-514.
143. Han, S.-O., R. I. Mahato, Y. K. Sung, and S. W. Kim. (2000) Development of Biomaterials for gene therapy. Mol. Therapy 2:302-317.
144. Harenberg, (1998), Med. Res. Rev., 18:1-20.
145. Heinemann U., et al., (2001); *Curr Opin Biotechnol.* 12(4):348-54.
146. Hennan J K (2005) Evaluation of PAI-039 [{1-Benzyl-5-[4-(trifluoromethoxy)phenyl]-1H-indol-3-yl}(oxo)acetic Acid], a Novel Plasminogen Activator Inhibitor-1 Inhibitor, in a Canine Model of Coronary Artery Thrombosis. Pharmacol Exp Ther. 314(2):710-6.
147. Hensch, T. K., Fagiolini, M., Mataga, N., Stryker, M. P., Baekkeskov, S., and Kash, S. F. (1998). Local GABA circuit control of experience-dependent plasticity in developing visual cortex. Science 282, 1504-1508.
148. Hering, H., and Sheng, M. (2001). Dendritic spines: structure, dynamics and regulation. Nat Rev Neurosci 2, 880-888.
149. Heynen, A. J., Yoon, B. J., Liu, C. H., Chung, H. J., Huganir, R. L., and Bear, M. F. (2003). Molecular mechanism for loss of visual cortical responsiveness following brief monocular deprivation. Nat Neurosci 6, 854-862.
150. Higgins D L and Bennett W F, (1990) Tissue Plasminogen Activator: The Biochemistry and Pharmacology of Variants Produced by Mutagenesis. Annual Review of Pharmacology and Toxicology Vol. 30: 91-121.
151. Huang, Z. J., Kirkwood, A., Pizzorusso, T., Porciatti, V., Morales, B., Bear, M. F., Maffei, L., and Tonegawa, S. (1999). BDNF regulates the maturation of inhibition and the critical period of plasticity in mouse visual cortex. Cell 98, 739-755.
152. Hubel, D. H., and Wiesel, T. N. (1970). The period of susceptibility to the physiological effects of unilateral eye closure in kittens. J Physiol 206, 419-436.
153. Johannson, B. (2000) "Brain Plasticity and Stroke Rehabilitation", Stroke, 31:223-230.
Kanematsu, A., et al. (2004) Collagenous matrices as release carriers of exogenous growth factors. Biomaterials. 25(18):4513-20.
154. Kesslak J P, Keirstead H S. (2003) Assessment of behavior in animal models of spinal cord injury. J Spinal Cord Med. 26(4):323-8.
155. Koester, H. J., and Sakmann, B. (1998). Calcium dynamics in single spines during coincident pre- and postsynaptic activity depend on relative timing of back-propagating action potentials and subthreshold excitatory postsynaptic potentials. Proc Natl Acad Sci USA 95, 9596-9601.
156. Krueger K, Busch E. Protocol of a thromboembolic stroke model in the rat: review of the experimental procedure and comparison of models. Invest Radiol. 2002. 37(11):600-8.
157. Krystosek, A., and Seeds, N. W. (1981). Plasminogen activator release at the neuronal growth cone. Science 213, 1532-1534.
158. Lamer T J (1994). Treatment of cancer-related pain: when orally administered medications fail. Mayo Clin Proc, 69:473-80.
159. Laske, D W, et al., 1997 Nat. Med. Tumor regression with regional distribution of the targeted toxin TF-CRM107 in patients with malignant brain tumors. 3(12):1362-8.
160. Leamey C A, et al., (2001) Disruption of retinogeniculate pattern formation by inhibition of soluble guanylyl cyclase. J Neurosci. 21(11):3871-80.
161. Lendvai, B., Stern, E. A., Chen, B., and Svoboda, K. (2000). Experience-dependent plasticity of dendritic spines in the developing rat barrel cortex in vivo. Nature 404, 876-881.
162. Liang, A., et al., (2005) Characterization of a small molecule PAI-1 inhibitor, ZK4044. Thromb Res. 115(4):341-50. Epub 2004 Nov. 13.
163. Liberatore G T, et al., Vampire bat salivary plasminogen activator (desmoteplase): a unique fibrinolytic enzyme that does not promote neurodegeneration. Stroke. 2003 February; 34(2):537-43.
164. Liepert, J., et al. (2000) Treatment-Induced Cortical Reorganization After Stroke in Humans, Stroke, 31:1210-1216.
165. Machado M, Salcman M, Kaplan R S, Montgomery E (1985). Expanded role of the cerebrospinal fluid reservoir in neuroongocology: indications, causes of revision, and complications. Neurosurgery 17:600-603.
166. Majewska, A., Brown, E., Ross, J., and Yuste, R. (2000a). Mechanisms of calcium decay kinetics in hippocampal spines: role of spine calcium pumps and calcium diffusion through the spine neck in biochemical compartmentalization. J Neurosci 20, 1722-1734.
167. Majewska, A., and Sur, M. (2003). Motility of dendritic spines in visual cortex in vivo: Changes during the critical period and effects of visual deprivation. Proc Natl Acad Sci USA 100, 16024-16029.
168. Majewska, A., Tashiro, A., and Yuste, R. (2000b). Regulation of spine calcium dynamics by rapid spine motility. J Neurosci 20, 8262-8268.
169. Maletic-Savatic, M., Malinow, R., and Svoboda, K. (1999). Rapid dendritic morphogenesis in CA1 hippocampal dendrites induced by synaptic activity. Science 283, 1923-1927.
170. Martinez-Arizala A. (2003) Methods to measure sensory function in humans versus animals. J Rehabil Res Dev. 40(4 Suppl 1):35-9.
171. Mataga N, Mizuguchi Y, Hensch T K (2004) Experience-dependent pruning of dendritic spines in visual cortex by tissue plasminogen activator. Neuron 44:1031-1041.
172. Mataga, N., Nagai, N., and Hensch, T. K. (2002). Permissive proteolytic activity for visual cortical plasticity. Proc Natl Acad Sci USA 99, 7717-7721.
173. Matus, A., Ackermann, M., Pehling, G., Byers, H. R., and Fujiwara, K. (1982). High actin concentrations in brain dendritic spines and postsynaptic densities. Proc Natl Acad Sci USA 79, 7590-7594.
174. Mathiowitz and Langer (1987) J. Controlled Release 5:13-22.
175. Mathiowitz et al. (1987) Reactive Polymers 6:275-283.
176. Mathiowitz et al. (1988) J. Appl. Polymer Sci. 35:755-774.
177. Mathiowitz et al. (1990) Scanning Microscopy 4:329-340;
178. Mathiowitz et al. (1992) J. Appl. Polymer Sci., 45:125-134.
179. McKinney, R. A., Capogna, M., Dürr, R., and Gähwiler, B. H. (1999). Miniature synaptic events maintain dendritic spines via AMPA receptor activation. Nature Neuroscience 2, 44-49.
180. McManus, M. T., and P. A. Sharp. (2002) Gene silencing in mammals by short interfering RNAs. Nature Rev. Genetics. 3:737-747.

181. Milwidsky, et al. (1991), Thrombo. Haemostat., 65:389-393.
182. Muller, C. M., and Griesinger, C. B. (1998). Tissue plasminogen activator mediates reverse occlusion plasticity in visual: cortex. Nat Neurosci 1, 47-53.
183. Nelles, G., et al. (1999) "Reorganization of sensory and motor systems in hemiplegic stroke patients. A positron emission study.", Stroke 30:1510-1516.
184. Nishiyama M, et al., (2003) Cyclic AMP/GMP-dependent modulation of Ca2+ channels sets the polarity of nerve growth-cone turning. Nature. 423(6943):990-5.
185. Noble L J, Wrathall J R (1985) Spinal cord contusion in the rat: morphometric analyses of alterations in the spinal cord. Exp Neurol 88:135-149.
186. Noble L J, Wrathall J R (1989a) Correlative analysis of lesion development and functional status after graded spinal cord contusive injuries in the rat. Exp Neurol 103:34-40.
187. Noble L J, Wrathall J R (1989b) Distribution and time course of protein extravasation in the spinal cord after contusive injury. Brain Res 482:57-66.
188. Obbens E A M T, Leavents M E, Beal J W, Lee Y Y (1985). Ommaya reservoirs in 387 cancer patients: a 15-year experience. Neurology 35:1274-1278.
189. Ohtani A, Inhibitory effect of a new butadiene derivative on the production of plasminogen activator inhibitor-1 in cultured bovine endothelial cells. J Biochem (Tokyo). 1996 December; 120(6):1203-8. Related Articles, Links
190. Olson, C. R., and Freeman, R. D. (1975). Progressive changes in kitten striate cortex during monocular vision. J Neurophysiol 38, 26-32.
191. Ommaya A K, Punjab M B (1963). Subcutaneous reservoir and pump for sterile access to ventricular cerebrospinal fluid. Lancet, 2:983-984.
192. Oray S, Majewska A, Sur M (in press) Effects of synaptic activity on dendritic spine motility of developing cortical layer 5 pyramidal neurons. Cerebral Cortex.
193. Paice J A, Penn R D, Shott S (1996). Intraspinal morphine for chronic pain: a retrospective, multicenter study. J Pain Symptom Manage, 11:71-80.
194. Panjabi M, Wrathall J R (1988) Biomechanical analysis of spinal cord injury and functional loss. Spine 13:1365-1370.
195. Parkinnen (1993), J. Biol. Chem. 268: 19726-19738.
196. Petersen, R. C., et al., (2001). Current Concepts in Mild Cognitive Impairment. *Arch. Neurol.* 58, 1985-1992.
197. Pizzorusso, T., Medini, P., Berardi, N., Chierzi, S., W. Fawcett, J., and Maffei, L. (2002). Reactivation of ocular dominance plasticity in the adult visual cortex. Science 298, 1248-1251.
198. Qian, Z., Gilbert, M. E., Colicos, M. A., Kandel, E. R., and Kuhl, D. (1993). Tissue-plasminogen activator is induced as an immediate-early gene during seizure, kindling and long-term potentiation. Nature 361, 453-457.
199. Raines A, Dr etc. hen K L, Marx K, Wrathall J R (1988) Spinal cord contusion in the rat: somatosensory evoked potentials as a function of graded injury. J Neurotrauma 5:151-160.
200. Ramos B P, et al., Dysregulation of protein kinase a signaling in the aged prefrontal cortex: new strategy for treating age-related cognitive decline. Neuron, 40(4):835-45.
201. Rijken, D. C. and Collen, D. (1981) Purification and characterization of the plasminogen activator secreted by human melanoma cells in culture. J. Biol. Chem., 256, 7035-7042.
202. Roberts L J, Finch P M, Goucke C R, Price L M (2001). Outcome of intrathecal opioids in chronic non-cancer pain. Eur J Pain, 5:353-61.
203. Sakata, et al. (1999), Am. Heart J., 137:1094-1099.
204. Sali, A. and Blundell, T L, (1993) J. Mol. Biol., 234, 779-815.
205. Santini, J T, et al. (2000) Microchips as Controlled Drug-delivery Devices Angewandte Chemie, International Edition, Vol. 39, pp. 2396-2407.
206. Sawtell, N. B., Frenkel, M. Y., Philpot, B. D., Nakazawa, K., Tonegawa, S., and Bear, M. F. (2003). NMDA Receptor-Dependent Ocular Dominance Plasticity in Adult Visual Cortex. Neuron 38, 977-985.
207. Schlaug, G., et al. (1999) The ischemic penumbra: operationally defined by diffusion and perfusion MRI. Neurology. 53(7):1528-37.
208. Schlott, et al. (1997), J. Biol. Chem. 272: 6067-6072.
Schmidt, C. E. and Leach, J. B., Neural tissue engineering: strategies for repair and regeneration. Annu. Rev. Biomed. Eng., 2003.5: 293-347.
209. Shatz, C. J., and Stryker, M. P. (1978). Ocular dominance in layer IV of the cat's visual cortex and the effects of monocular deprivation. J Physiol 281, 267-283.
210. Siconolfi, L. B., and Seeds, N. W. (2001). Induction of the plasminogen activator system accompanies peripheral nerve regeneration after sciatic nerve crush. J Neurosci 21, 4336-4347.
211. Sprengers, E. D. and Kluft, C. (1987). Plasminogen activator inhibitors. Blood 69, 381-387.
212. Star, E. N., Kwiatkowski, D. J., and Murthy, V. N. (2002). Rapid turnover of actin in dendritic spines and its regulation by activity. Nat Neurosci 5, 239-246.
213. Sun, et al., (2000) Pharmacol. Rev., 52:325.
214. Takenaga, M., et al., (2004) Optimum formulation for sustained-release insulin. Int J Pharm. 271(1-2):85-94.
215. Teng Y D, Wrathall J R (1996) Evaluation of cardiorespiratory parameters in rats after spinal cord trauma and treatment with NBQX, an antagonist of excitatory amino acid receptors. Neurosci Lett 209:5-8.
216. Teng, Y D and Wrathall, J R (1997) J. Neuroscience, 17 (11), pp. 4359-4366.
217. Teng, Y. D., et al. (2002) Functional recovery following traumatic spinal cord injury mediated by a unique polymer scaffold seeded with neural stem cells. Proc Natl Acad Sci USA, 99(5): p. 3024-9.
218. Teng, Y. D., et al. (2004). Proc. Natl. Acad. Sci. 101(9), pp. 3071-3076.
219. Thomas C K, Noga B R. (2003) Physiological methods to measure motor function in humans and animals with spinal cord injury. J Rehabil Res Dev. 40(4 Suppl 1):25-33.
220. Thomas, N., and Klibanov, A. M. (2003) Non-viral gene therapy: polycation-mediated DNA delivery. Appl. Microbiol. Biotechnol. 62:27-34.
221. Toombs C F. (2001) Alfimeprase: pharmacology of a novel fibrinolytic metalloproteinase for thrombolysis. Haemostasis. 31(3-6): 141-7.
222. Trachtenberg, J. T., and Stryker, M. P. (2001). Rapid anatomical plasticity of horizontal connections in the developing visual cortex. J Neurosci 21, 3476-3482.
223. Trachtenberg, J. T., Trepel, C., and Stryker, M. P. (2000). Rapid extragranular plasticity in the absence of thalamo-cortical plasticity in the developing primary visual cortex. Science 287, 2029-2032.
224. Tutak U, Doleys D M (1996). Intrathecal infusion systems for treatment of chronic low back and leg pain of noncancer origin. South Med J, 89:295-300.

225. Usman, et al., (1996) Curr. Opin. Struct. Biol., 1:527.
226. Webb, A A, et al. (2004) Behavioural analysis of the efficacy of treatments for injuries to the spinal cord in animals. Vet Rec. 155(8):225-30.
227. Werb, Z. (1997). ECM and cell surface proteolysis: regulating cellular ecology. Cell 91, 439-442.
228. Westphal M, Hild D C, Bortey E, Delavault P, Olivares R, Warnke P C, Whittle I R, Jaaskelainen J, Ram Z (2003). A phase 3 trial of local chemotherapy with biodegradable carmustine (BCNU) wafers (Gliadel wafers) in patients with primary malignant glioma. Neuro-oncol 5:79-88.
229. White (1998), J. Am. Coll. Cardiol., 31: 487-496.
230. Wiesel, T. N., and Hubel, D. H. (1963). Single-Cell Responses in Striate Cortex of Kittens Deprived of Vision in One Eye. J Neurophysiol 26, 1003-1017.
231. Winkemuller M, Winkemuller W (1996). Long-term effects of continuous intrathecal opioid treatment in chronic pain of nonmalignant etiology. J Neurosurg, 85:458-467.
232. Wishart D., (2005) Curr Pharm Biotechnol., 6(2):105-20.
233. Wrathall J R, Pettegrew R, Harvey F (1985) Spinal cord contusion in the rat: production of graded, reproducible injury groups. Exp Neurol 88:108-122.
234. Wu M P, Tamada J A, Brem H, Langer R (1994). In vivo versus in vitro degradation of controlled release polymers for intracranial surgical therapy. J Biomed Mater Res, 28:387-95.
235. Xerri, C. et al. (1998) Plasticity of primary somatosensory motor cortex paralleling sensorimotor skill recovery from stroke in adult monkeys, J. Neurophysiol., 79:2119-2148.
236. Ye, B., et al., (2004) Synthesis and biological evaluation of piperazine-based derivatives as inhibitors of plasminogen activator inhibitor-1 (PAI-1). Bioorg Med Chem. Lett. 14(3):761-5.
237. Yelverton, E., et al., (1983) Cloning and expression of human tissue-type plasminogen activator cDNA in *E. coli.*, Nature, 301(5897):214-21
238. Yuste, R., and Denk, W. (1995). Dendritic spines as basic functional units of neuronal integration. Nature 375, 682-684.
239. Zavalova, L., (1996) Genes from the medicinal leech (Hirudo medicinalis) coding for unusual enzymes that specifically cleave endo-epsilon (gamma-Glu)-Lys isopeptide bonds and help to dissolve blood clots. Mol Gen Genet. 253(1-2):20-5.
240. Zavalova L, et al., (2002) Fibrinogen-fibrin system regulators from bloodsuckers. Biochemistry (Mosc). 67(1):135-42.

Lengthy table referenced here

US08969295-20150303-T00001

Please refer to the end of the specification for access instructions.

Lengthy table referenced here

US08969295-20150303-T00002

Please refer to the end of the specification for access instructions.

Lengthy table referenced here

US08969295-20150303-T00003

Please refer to the end of the specification for access instructions.

Lengthy table referenced here

US08969295-20150303-T00004

Please refer to the end of the specification for access instructions.

Lengthy table referenced here

US08969295-20150303-T00005

Please refer to the end of the specification for access instructions.

Lengthy table referenced here

US08969295-20150303-T00006

Please refer to the end of the specification for access instructions.

Lengthy table referenced here

US08969295-20150303-T00007

Please refer to the end of the specification for access instructions.

Lengthy table referenced here

US08969295-20150303-T00008

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08969295B2). An electronic copy of the table will also be available from the USPTO upon request and payment of the fee set forth in 37 CFR 1.19(b)(3).

We claim:

1. A method for promoting recovery or reorganization in the nervous system of a subject suffering from a neurodevelopmental disorder, the method comprising administering to the subject a tissue plasminogen activator (tPA) and an insulin like growth factor-1 (IGF 1), wherein the neurodevelopmental disorder is selected from the group consisting of: autism, dyslexia, Asperger's syndrome, pervasive developmental disorders—not otherwise specified, Tourette's syndrome, and personality disorders.

2. The method of claim 1, wherein the tissue plasminogen activator (tPA) and insulin-like growth factor-1 (IGF-1) are administered following diagnosis of the neurodevelopmental disorder.

3. The method of claim 1 or claim 2, wherein the tissue plasminogen activator (tPA) and insulin-like growth factor-1 (IGF-1) are administered together or separately following diagnosis of the specific neurodevelopmental disorder.

4. The method of claim 1, wherein the neurodevelopmental disorder is autism.

5. A method for promoting recovery or reorganization in the nervous system of a subject suffering from a neuropsychiatric disorder, comprising administering to the subject a tissue plasminogen activator (tPA) and an insulin like growth factor-1 (IGF 1).

6. The method of claim 5, wherein the tissue plasminogen activator (tPA) and insulin-like growth factor-1 (IGF-1) are administered following diagnosis of the neuropsychiatric disorder.

7. The method of claim 5 or claim 6, wherein the tissue plasminogen activator (tPA) and insulin-like growth factor-1 (IGF-1) are administered together or separately following diagnosis of the specific neuropsychiatric disorder.

8. The method of claim 5, wherein the neuropsychiatric disorder is selected from the group consisting of: schizophrenia and bipolar disorders.

9. The method of claim 5, wherein the neuropsychiatric disorder is schizophrenia.

* * * * *